(12) United States Patent
Mikamiyama et al.

(10) Patent No.: US 8,324,249 B2
(45) Date of Patent: Dec. 4, 2012

(54) TETRAHYDROPYRIDINYL AND DIHYDROPYRROLYL COMPOUNDS AND THE USE THEREOF

(75) Inventors: Hidenori Mikamiyama, Osaka (JP); Chiyou Ni, Belle Mead, NJ (US); Bin Shao, Richboro, PA (US); Laykea Tafesse, Robbinsville, NJ (US)

(73) Assignees: Purdue Pharma L.P., Stamford, CT (US); Shionogi & Co., Ltd., Osaka (JP)

( * ) Notice: Subject to any disclaimer, the term of this patent is extended or adjusted under 35 U.S.C. 154(b) by 0 days.

(21) Appl. No.: 13/056,839

(22) PCT Filed: Aug. 3, 2009

(86) PCT No.: PCT/US2009/004437
§ 371 (c)(1),
(2), (4) Date: Jan. 31, 2011

(87) PCT Pub. No.: WO2010/014257
PCT Pub. Date: Feb. 4, 2010

(65) Prior Publication Data
US 2011/0136833 A1   Jun. 9, 2011

Related U.S. Application Data

(60) Provisional application No. 61/129,956, filed on Aug. 1, 2008.

(51) Int. Cl.
*A01N 43/40*   (2006.01)
*A61K 31/445*   (2006.01)

(52) U.S. Cl. ........ 514/318; 514/326; 544/192; 544/193; 544/208; 544/209; 544/210; 544/211

(58) Field of Classification Search .................. 514/318, 514/326; 544/192, 193, 208, 209, 210, 211
See application file for complete search history.

(56) References Cited

U.S. PATENT DOCUMENTS

| | | | |
|---|---|---|---|
| 6,136,839 A | 10/2000 | Isakson et al. | |
| 7,384,982 B2 | 6/2008 | Bay et al. | |
| 2005/0222410 A1 | 10/2005 | Stokes et al. | |
| 2006/0035884 A1 | 2/2006 | Neitzel et al. | |
| 2007/0093528 A1 | 4/2007 | Kuwabara et al. | |
| 2009/0105248 A1* | 4/2009 | Ho et al. | 514/235.2 |
| 2009/0105249 A1 | 4/2009 | Benjamin et al. | |
| 2009/0239910 A1 | 9/2009 | Chen et al. | |
| 2009/0306136 A1 | 12/2009 | Matsumura et al. | |
| 2010/0022595 A1 | 1/2010 | Chen et al. | |
| 2010/0063030 A1 | 3/2010 | Kyle et al. | |
| 2010/0311792 A1 | 12/2010 | Shao et al. | |
| 2011/0059893 A1* | 3/2011 | Sun et al. | 514/13.5 |
| 2011/0070189 A1* | 3/2011 | Li et al. | 424/85.2 |
| 2011/0288129 A1* | 11/2011 | Vasudevan et al. | 514/334 |

FOREIGN PATENT DOCUMENTS

| | | |
|---|---|---|
| EP | 0 280 873 A1 | 9/1988 |
| EP | 1 180 514 A1 | 2/2002 |
| EP | 1 657 240 A1 | 5/2006 |
| WO | WO 98/54181 A1 | 12/1998 |
| WO | WO 98/54182 A1 | 12/1998 |
| WO | WO 99/43658 A1 | 9/1999 |
| WO | WO 03/092686 A1 | 11/2003 |
| WO | WO 2005/068448 A1 | 7/2005 |
| WO | WO 2005092863 A1 * | 10/2005 |
| WO | WO 2005/113542 A2 | 12/2005 |
| WO | WO 2006/040181 A2 | 4/2006 |
| WO | WO 2007/014290 A2 | 2/2007 |
| WO | WO 2007/053436 A1 | 5/2007 |
| WO | WO 2007/062318 A2 | 5/2007 |
| WO | WO 2008/013622 A2 | 1/2008 |
| WO | WO 2008/150447 A1 | 12/2008 |
| WO | WO 2009/151152 A1 | 12/2009 |
| WO | WO 2010/114181 A1 | 10/2010 |

OTHER PUBLICATIONS

Bingham, A.L., et al., "Over one hundred solvates of sulfathiazole," *Chem. Commun.* 2001:603-604, The Royal Society of Chemistry, England (2001).
Brower, V., "New paths to pain relief: A better understanding of the mechanisms by which pain signals are relayed in the nervous system is paving the way for novel treatments," *Nat. Biotechnol. 18*:387-391, Nature America Inc., United States (2000).
Bundgaard, H., "Formation of Prodrugs of Amines, Amides, Ureides, and Imides," *Methods Enzymol. 112*:347-359, Academic Press, Inc., United States (1985).
Bundgaard, H., "Design and Application of Prodrugs," in *A Textbook of Drug Design and Development*, p. 113-191, Krogsgaard-Larsen, P. and Bundgaard, H., eds., Harwood Academic Publishers GmbH, England (1991).
Bundgaard, H., "(C) Means to Enhance Penetration: (1) Prodrugs as a means to improve the delivery of peptide drugs," *Adv. Drug Deliv. Rev. 8*:1-38, Elsevier Science Publishers B.V., Netherlands (1992).

(Continued)

*Primary Examiner* — James O Wilson
*Assistant Examiner* — Alexander R Pagano
(74) *Attorney, Agent, or Firm* — Sterne, Kessler, Goldstein & Fox P.L.L.C.

(57) ABSTRACT

The invention relates to tetrahydropyridinyl and dihydropyrrolyl compounds of Formula (I): and pharmaceutically acceptable salts, prodrugs, or solvates thereof, wherein X, Y, Z, $R^1$, $R^2$, m, and n are defined as set forth in the specification. The invention is also directed to the use of compounds of Formula (I) to treat a disorder responsive to the blockade of calcium channels, and particularly N-type calcium channels. Compounds of the present invention are especially useful for treating pain.

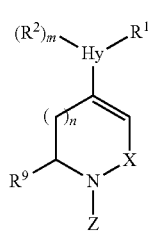

64 Claims, No Drawings

OTHER PUBLICATIONS

Caira, M.R., et al., "Preparation and Crystal Characterization of a Polymorph, a Monohydrate, and an Ethyl Acetate Solvate of the Antifungal Fluconazole," *J. Pharmaceut. Sci.* 93:601-611, Wiley-Liss, Inc. and the American Pharmacists Association, United States (2004).

Castellano, A., et al. "Cloning and Expression of a Neuronal Calcium Channel β Subunit," *J. Biol. Chem.* 268:12359-12366, The American Society for Biochemistry and Molecular Biology, Inc., United States (1993).

Dubel, S.J., et al., "Molecular cloning of the α-1 subunit of an ω-conotoxin-sensitive calcium channel," *Proc. Natl. Acad Sci. USA* 89:5058-5062, National Academy of Sciences, United States (1992).

Filer, C.N., "The Preparation and Characterization of Tritiated Neurochemicals," in *Isotopes in the Physical and Biomedical Sciences: vol. 1: Labeled Compounds (Part A)*, p. 156-192, Buncel, E. and Jones, J.R., eds., Elsevier Science Publishers B.V., Netherlands (1987).

Gould R.J., et al., "Antischizophrenic drugs of the diphenylbutylpiperidine type act as calcium channel antagonists," *Proc. Natl. Acad. Sci. USA* 80:5122-5125, National Academy of Sciences, United States (1983).

Hamill, O.P., et al., "Improved Patch-Clamp Techniques for High-Resolution Current Recording from Cells and Cell-Free Membrane Patches," *Pflüegers Arch.* 391:85-100, Springer-Verlag, Germany (1981).

Han, H.-K., "Targeted Prodrug Design to Optimize Drug Delivery," *AAPS Pharmsci.* 2:article 6 (http://www.pharmsci.org/), American Association of Pharmaceutical Scientists, United States (2000).

Hanson, G.R., "Analgesic, Antipyretic and Anti-inflammatory Drugs," in *Remington: The Science and Practice of Pharmacy. vol. II*, 19th Edition, pp. 1196-1221, Gennaro, A., ed., Lippincott Williams & Wilkins, United States (1995).

Hu, L.-Y., et al., "The Discovery of [1-(4-Dimethylamino-benzyl)-piperidin-4-yl]-[4-(3,3-dimethylbutyl)-phenyl]-(3-methyl-but-2-enyl)-Amine, an N-type $Ca^{+2}$ Channel Blocker with Oral Activity for Analgesia," *Bioorg. Med. Chem.* 8:1203-1212, Elsevier Science Ltd., England (2000).

Hu, L.-Y., et al., "Structure-Activity Relationship of *N*-Methyl-*N*-Aralkyl-Peptidylamines As Novel N-Type Calcium Channel Blockers," *Bioorg. Med. Chem. Lett.* 9:2151-2156, Elsevier Science Ltd., England (1999).

Hu, L.-Y, et al., "Synthesis of a Series of 4-Benzyloxyaniline Analogues as Neuronal N-Type Calcium Channel Blockers with Improved Anticonvulsant and Analgesic Properties," *J. Med. Chem.* 42:4239-4249, American Chemical Society, United States (1999).

Hunskaar, S., et al., "Formalin test in mice, a useful technique for evaluating mild analgesics," *J. Neurosci. Methods* 14:69-76, Elsevier Science Publishers B.V., Netherlands (1985).

Insel, P.A., "Analgesic-Antipyretic and Antiinflammatory Agents and Drugs Employed in the Treatment of Gout," in *Goodman & Gilman's The Pharmacological Basis of Therapeutics, 9th Edition*, p. 617-657, The McGraw-Hill Companies, United States (1996).

Ito, M., "Long-Term Depression," *Annu. Rev. Neurosci.* 12:85-102, Annual Reviews, Inc., United States (1989).

Janis, R.A. and Triggle, D.J., "Drugs Acting on Calcium Channels," in *Calcium Channels: Their Properties, Functions, Regulation and Clinical Relevance*, p. 195-249, Hurwitz, L. et al., eds., CRC Press, Inc., United States (1991).

Kakeya N., et al., "Studies on Prodrugs of Cephalosporins. I.[1)] Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephyem-4-carboxylic Acid," *Chem. Pharm. Bull.* 32:692-698, Pharmaceutical Society of Japan, Japan (1984).

Kim H.-L., et al., "Rat brain expresses an alternatively spliced form of the dihydropyridine-sensitive L-type calcium channel α2 subunit," *Proc. Natl. Acad. Sci. USA* 89:3251-3255, National Academy of Sciences, United States (1992).

Kim, S.H. and Chung, J.M., "An experimental model for peripheral neuropathy produced by segmental spinal nerve ligation in the rat," *Pain* 50:355-363, Elsevier Science Publishers B.V., Netherlands (1992).

Koch, W.J., et al., "cDNA Cloning of a Dihydropyridine-sensitive Calcium Channel from Rat Aorta," *J. Biol. Chem.* 265:17786-17791, The American Society for Biochemistry and Molecular Biology, Inc., United States (1990).

Lee, J.S., et al., "Synthesis and In Vitro Activity of Novel Isoxazolyl Tetrahydropyridinyl Oxazolidinone Antibacterial Agents," *Bioorg. Med. Chem. Lett.* 13:4117-4120, Elsevier Ltd., England (2003).

Levine, J. and Taiwo, Y., "Inflammatory pain," in *Textbook of Pain*, p. 45-56, Wall, P.D. and Melzack, R., eds., Churchill Livingstone, Inc., United States (1994).

Li, W.-R., et al., "Efficient Total Synthesis of Pulchellalactam, a CD45 Protein Tyrosine Phosphatase Inhibitor," *J. Org. Chem.* 67:4702-4706, American Chemical Society, United States (2002).

Lin, Z., et al., "Identification of Functionally Distinct Isoforms of the N-Type $Ca^{2+}$ Channel in Rat Sympathetic Ganglia and Brain," *Neuron* 18:153-166, Cell Press, United States (1997).

Lukyanetz, E.A., et al., "Selective Blockade of N-Type Calcium Channels by Levetiracetam," *Epilepsia* 43:9-18, International League Against Epilepsy, United States (2002).

Moreno Davila, H., "Molecular and Functional Diversity of Voltage-Gated Calcium Channels," *Ann. N. Y. Acad. Sci.* 868:102-117, New York Academy of Sciences, United States (1999).

Nielsen, N.M. and Bundgaard, H., "Glycolamide Esters as Biolabile Prodrugs of Carboxylic Acid Agents: Synthesis, Stability, Bioconversion, and Physicochemical Properties," *J. Pharm. Sci.* 77:285-298, American Pharmaceutical Association, United States (1988).

Nuglisch J., et al., "Protective Effect of Nimodipine Against Ischemic Neuronal Damage in Rat Hippocampus Without Changing Postischemic Cerebral Blood Flow," *J. Cereb. Blood Flow Metab.* 10:654-659, Raven Press, Ltd., United States (1990).

Pragnell, M., et al. "Cloning and tissue-specific expression of the brain calcium channel β-subunit," *FEBS Lett.* 291:253-258, Federation of European Biochemical Societies, Netherlands (1991).

Schwartz, A., et al., "Receptors for Calcium Antagonists," *Am. J. Cardiol.* 62:3G-6G, Excerpta Medica, United States (1988).

Song, Y., et al., "(S)-4-Metyl-2-(methylamino)pentanoic Acid [4,4-Bis(4-fluorophenyl)butyl]amide Hydrochloride, a Novel Calcium Channel Antagonist, Is Efficacious in Several Animal Models of Pain," *J. Med. Chem.* 43:3474-3477, American Chemical Society, United States (2000).

Stein, C., et al., "Unilateral Inflammation of the Hindpaw in Rats as a Model of Prolonged Noxious Simulation: Alterations in Behavior and Nociceptive Thresholds," *Pharmacol. Biochem. Behavior* 31:445-451, Pergamon Press plc, United States (1988).

van Tonder, E.C., et al., "Preparation and Physicochemical Characterization of 5 Niclosamide Solvates and 1 Hemisolvate," *AAPS PharmSciTech* 5:Article 12, http://www.aapspharmscitech.org) Springer, United States (2004).

Vanegas, H. and Schaible H.-G., "Effects of antagonists to high-threshold calcium channels upon spinal mechanisms of pain, hyperalgesia and allodynia," *Pain* 85:9-18, Elsevier Science B.V., Netherlands (2000).

Wallace, M.S., "Calcium and Sodium Channel Antagonists for the Treatment of Pain," *Clin. J. Pain* 16:S80-S85, Lippincott Williams & Wilkins, Inc., United States (2000).

English language Abstract of European Patent Publication No. EP 0 280 873 A1, European Patent Office, espacenet database—Worldwide, (2001).

International Search Report for International Application No. PCT/US2009/004437, European Patent Office, Rijswijk, Netherlands, mailed Apr. 21, 2010.

Written Opinion of the International Searching Authority for International Application No. PCT/US2009/004437, European Patent Office, Munich, Germany, Completed Apr. 21, 2010.

* cited by examiner

TETRAHYDROPYRIDINYL AND DIHYDROPYRROLYL COMPOUNDS AND THE USE THEREOF

This application is a National Stage of International Application No. PCT/US2009/004437, filed Aug. 3, 2009, which claims the benefit of U.S. Provisional Application No. 61/129,956, filed Aug. 1, 2008.

REFERENCE TO SEQUENCE LISTING SUBMITTED ELECTRONICALLY

The content of the electronically submitted substitute sequence listing, file name 1861_2480001_SequenceListing_ascii.txt, size 2,709 bytes; and date of creation Aug. 30, 2012, filed herewith, is incorporated herein by reference in its entirety.

BACKGROUND OF THE INVENTION

1. Field of the Invention

This invention is in the field of medicinal chemistry. The invention relates to novel tetrahydropyridinyl and dihydropyrrolyl compounds and the use of these compounds as blockers of calcium ($Ca^{2+}$) channels.

2. Background Art

Calcium ions play fundamental roles in the regulation of many cellular processes. It is therefore essential that their intracellular levels be maintained under strict, yet dynamic control (Davila, H. M., *Annals of the New York Academy of Sciences*, pp. 102-117 (1999)). Voltage-gated calcium channels (VGCC) serve as one of the important mechanisms for fast calcium influx into the cell. Calcium channels are hetero-oligomeric proteins consisting of a pore-forming subunit ($\alpha 1$), which is able to form functional channels on its own in heterologous expression systems, and a set of auxiliary or regulatory subunits. Calcium channels have been classified based on their pharmacological and/or electrophysiological properties. The classification of voltage-gated calcium channels divides them into three groups: (i) high voltage-activated (HVA) channels, which include L-, N-, P-, and Q-types; (ii) intermediate (IVA) voltage-activated R-type channels; and (iii) low voltage-activated (LVA) T-type channels (Davila, supra). Voltage-gated calcium channels (VGCC) are also known as voltage-dependent calcium channels (VDCC) or voltage-sensitive calcium channels (VSCC).

Voltage-sensitive calcium channels (VSCC) regulate intracellular calcium concentration, which affects various important neuronal functions such as cellular excitability, neurotransmitter release, hormone secretion, intracellular metabolism, neurosecretory activity and gene expression (Hu et al., *Bioorganic & Medicinal Chemistry* 8:1203-1212 (2000)). N-type channels are found mainly in central and peripheral neurons, being primarily located on presynaptic nerve terminals. These channels regulate the calcium flux required for depolarization-evoked release of a transmitter from synaptic endings. The transmission of pain signals from the periphery to the central nervous system (CNS) is mediated by N-type calcium channels located in the spinal cord (Song et al., *J. Med. Chem.* 43:3474-3477 (2000)).

The six types of calcium channels (i.e., L, N, P, Q, R, and T) are expressed throughout the nervous system (Wallace, M. S., *The Clinical Journal of Pain* 16:580-585 (2000)). Voltage-sensitive calcium channels of the N-type exist in the superficial laminae of the dorsal horn and are thought to modulate nociceptive processing by a central mechanism. Blockade of the N-type calcium channel in the superficial dorsal horn modulates membrane excitability and inhibits neurotransmitter release, resulting in pain relief. Wallace (supra) suggests that based on animal models, N-type calcium channel antagonists have a greater analgesic potency than sodium channel antagonists.

N-type calcium channel blockers have usefulness for neuroprotection and analgesia. Ziconotide, which is a selective N-type calcium channel blocker, has been found to have analgesic activity in animal models and neuroprotective activity in focal and global ischemia models (Song et al., supra). Examples of known calcium channel blockers include flunarizine, fluspirilene, cilnipide, PD 157767, SB-201823, SB-206284, NNC09-0026, and PD 151307 (Hu et al., supra).

Blockade of N-type channels can prevent and/or attenuate subjective pain as well as primary and/or secondary hyperalgesia and allodynia in a variety of experimental and clinical conditions (Vanegas, H. et al., *Pain* 85:9-18 (2000)). N-type voltage-gated calcium channels (VGCC) play a major role in the release of synaptic mediators such as glutamate, acetylcholine, dopamine, norepinephrine, gamma-aminobutyric acid (GABA) and calcitonin gene-related peptide (CGRP).

Inhibition of voltage-gated L-type calcium channels has been shown to be beneficial for neuroprotection (Song et al., supra). However, inhibition of cardiac L-type calcium channels can lead to hypotension. It is believed that a rapid and profound lowering of arterial pressure tends to counteract the neuroprotective effects of L-type calcium channel blockers. A need exists for antagonists that are selective for N-type calcium channels over L-type calcium channels to avoid potential hypotensive effects.

BRIEF SUMMARY OF THE INVENTION

The present invention is related to the use of tetrahydropyridinyl and dihydropyrrolyl compounds represented by Formula I, below, and the pharmaceutically acceptable salts, prodrugs and solvates thereof, as blockers of calcium ($Ca^{2+}$) channels. Compounds of Formula I show selectivity as N-type calcium channel blockers.

The invention is also related to treating a disorder responsive to the blockade of calcium channels in a mammal suffering from excess activity of said channels by administering an effective amount of a compound of Formula I, or a pharmaceutically acceptable salt, prodrug or solvate thereof, as described herein. Specifically, the invention is related to treating a disorder responsive to the blockade of N-type calcium channels in a mammal suffering from excess activity of said channels by administering an effective amount of a compound of Formula I, or a pharmaceutically acceptable salt, prodrug or solvate thereof, as described herein.

Compounds useful in the present invention have not been heretofore reported. Thus, one aspect of the present invention is directed to novel compounds of Formula I, as well as their pharmaceutically acceptable salts, prodrugs and solvates.

Another aspect of the present invention is directed to the use of the novel compounds of Formula I, and their pharmaceutically acceptable salts, prodrugs and solvates, as blockers of N-type calcium channels.

A further aspect of the present invention is to provide a method for treating pain (e.g., acute pain, chronic pain, which includes but is not limited to, neuropathic pain and inflammatory pain, or surgical pain) by administering an effective amount of a compound of Formula I, or a pharmaceutically acceptable salt, prodrug or solvate thereof, to a mammal in need of such treatment. Specifically, the present invention provides a method for preemptive or palliative treatment of pain by administering an effective amount of a compound of Formula I, or a pharmaceutically acceptable salt, prodrug or solvate thereof, to a mammal in need of such treatment.

A further aspect of the present invention is to provide a method for treating stroke, neuronal damage resulting from head trauma, epilepsy, migraine, a mood disorder, schizophrenia, a neurodegenerative disorder (e.g., Alzheimer's disease, amyotrophic lateral sclerosis (ALS), or Parkinson's disease), depression, anxiety, a psychosis, hypertension, or cardiac arrhythmia, by administering an effective amount of a compound of Formula I, or a pharmaceutically acceptable salt, prodrug or solvate thereof, to a mammal in need of such treatment.

A further aspect of the present invention is to provide a pharmaceutical composition useful for treating a disorder responsive to the blockade of calcium ion channels, especially N-type calcium ion channels, said pharmaceutical composition containing an effective amount of a compound of Formula I, or a pharmaceutically acceptable salt, prodrug or solvate thereof, in a mixture with one or more pharmaceutically acceptable carriers.

Also, an aspect of the invention is to provide a method of modulating calcium channels, especially N-type calcium channels, in a mammal, wherein said method comprises administering to the mammal an effective amount of at least one compound of Formula I, or a pharmaceutically acceptable salt, prodrug or solvate thereof.

A further aspect of the present invention is to provide radiolabeled compounds of Formula I and the use of such compounds, or their pharmaceutically acceptable salts, prodrugs or solvates, as radioligands for their binding site on the calcium channel.

A further aspect of the invention is to provide a method for screening a candidate compound for the ability to bind to a binding site on a protein using a radiolabeled compound of Formula I, which includes but is not limited to, a $^3$H, $^{11}$C, and $^{14}$C radiolabeled compound of Formula I, or a pharmaceutically acceptable salt, prodrug or solvate thereof. This method comprises a) introducing a fixed concentration of the radiolabeled compound to a soluble or membrane-associated protein or fragment thereof to form a mixture; b) titrating the mixture with a candidate compound; and c) determining the binding of the candidate compound to said binding site.

A further aspect of the invention is to provide the use of a compound of Formula I, or a pharmaceutically acceptable salt, prodrug or solvate thereof, in the manufacture of a medicament for treating pain in a mammal. In one embodiment, the invention provides the use of a compound of Formula I, or a pharmaceutically acceptable salt, prodrug or solvate thereof, in the manufacture of a medicament for palliative or preemptive treatment of pain, such as acute pain, chronic pain, or surgical pain.

A further aspect of the invention is to provide the use of a compound of Formula I, or a pharmaceutically acceptable salt, prodrug or solvate thereof, in the manufacture of a medicament for treating stroke, neuronal damage resulting from head trauma, epilepsy, migraine, a mood disorder, schizophrenia, a neurodegenerative disorder, depression, anxiety, a psychosis, hypertension, or cardiac arrhythmia in a mammal.

Additional embodiments and advantages of the invention will be set forth in part in the description that follows, and will flow from the description, or may be learned by practice of the invention. The embodiments and advantages of the invention will be realized and attained by means of the elements and combinations particularly pointed out in the appended claims.

It is to be understood that both the foregoing summary and the following detailed description are exemplary and explanatory only and are not restrictive of the invention, as claimed.

DETAILED DESCRIPTION OF THE INVENTION

One aspect of the present invention is based on the use of compounds of Formula I, and the pharmaceutically acceptable salts, prodrugs and solvates thereof, as blockers of $Ca^{2+}$ channels. In view of this property, compounds of Formula I, and the pharmaceutically acceptable salts, prodrugs and solvates thereof, are useful for treating disorders responsive to the blockade of calcium ion channels. In one aspect, compounds of Formula I, and the pharmaceutically acceptable salts, prodrugs and solvates thereof, selectively block N-type calcium ion channels and, thus, are useful for treating disorders responsive to the selective blockade of N-type calcium ion channels.

The compounds useful in this aspect of the invention are compounds represented by Formula I:

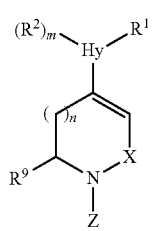

and pharmaceutically acceptable salts, prodrugs and solvates thereof, wherein:

Hy is a 6-membered heteroaromatic ring, a 5-membered heteroaromatic ring, or a 5-membered heterocyclic ring, wherein said Hy has at least one nitrogen atom, and wherein said Hy is attached to the tetrahydropyridinyl or dihydropyrrolyl ring by a carbon atom;

$R^1$ is attached to a carbon atom of said Hy ring and is selected from the group consisting of
 a) —C(=W)NR$^3$R$^4$;
 b) —C(=O)OR$^5$;
 c) —NR$^6$—C(=O)R$^7$;
 d) cyano;
 e) hydroxyalkyl; and
 f) a 5-membered, N-containing heteroaryl or a 5-membered, partially unsaturated, N-containing heterocyclo each of which is optionally substituted with one or two substituents each independently selected from the group consisting of alkyl, alkoxy, halogen, haloalkyl, haloalkoxy, hydroxy, hydroxyalkyl, cyano, amino, aminoalkyl, alkylamino, and dialkylamino; wherein
 W is O or NR$^{14}$, wherein
 R$^{14}$ is hydrogen or alkyl;
 R$^3$, R$^4$, and R$^7$ are each independently selected from the group consisting of hydrogen, alkyl, alkenyl, alkynyl, haloalkyl, hydroxyalkyl, cycloalkyl, (cycloalkyl)alkyl, cycloalkenyl, (cycloalkenyl)alkyl, heterocyclo, heterocycloalkyl, aryl, arylalkyl, heteroaryl, and heteroarylalkyl, wherein the cycloalkyl, cycloalkenyl, heterocyclo, aryl and heteroaryl portions thereof are optionally substituted with one or more substituents each independently selected from the group consisting of alkyl, alkoxy, halogen, haloalkyl, haloalkoxy, hydroxy, hydroxyalkyl, cyano, amino, aminoalkyl, alkylamino, dialkylamino, and hydroxyalkylamino; and $R^5$ and $R^6$ are hydrogen or alkyl;

$R^2$ is selected from the group consisting of alkyl, alkenyl, alkynyl, halogen, hydroxyalkyl, hydroxy, alkoxy, alkoxyalkyl, haloalkyl, haloalkoxy, haloalkoxyalkyl, nitro, cyano, amino, alkylamino, and dialkylamino;

m is 0, 1, 2, or 3;

n is 0 or 1;

X is —CHR$^8$— or —C(=O)—;

$R^8$ and $R^9$ are both hydrogen or together form a bridge —(CH$_2$)$_p$—, wherein p is 2, 3, or 4;

Z is $Z^1$ or $Z^2$, wherein $Z^1$ is —SO$_2$—R$^{10}$, wherein $R^{10}$ is selected from the group consisting of C$_{3-12}$ alkyl, halo(C$_{3-12}$)alkyl, C$_{5-12}$ cycloalkyl, (C$_{3-12}$ cycloalkyl)alkyl, C$_{5-12}$ cycloalkenyl, (C$_{3-12}$ cycloalkenyl)alkyl, heterocyclo, heterocycloalkyl, aryl, arylalkyl, heteroaryl, heteroarylalkyl, arylamino, and aryl(alkyl)amino, wherein the cycloalkyl, cycloalkenyl, heterocyclo, aryl and heteroaryl portions thereof are optionally substituted with one or more substituents each independently selected from the group consisting of alkyl, alkoxy, halogen, haloalkyl, haloalkoxy, hydroxy, hydroxyalkyl, cyano, amino, aminoalkyl, alkylamino, dialkylamino, and hydroxyalkylamino; and $Z^2$ is —C(R$^{11}$R$^{12}$)R$^{13}$, wherein $R^{11}$ and $R^{12}$ are each independently selected from the group consisting of hydrogen, alkyl, haloalkyl, hydroxyalkyl, halogen, hydroxy, alkoxy, alkoxyalkyl, haloalkoxy, haloalkoxyalkyl, cyano, amino, aminoalkyl, alkylaminoalkyl, and dialkylaminoalkyl; and $R^{13}$ is selected from the group consisting of aryl, arylalkyl, heteroaryl, and heteroarylalkyl, wherein the aryl and heteroaryl portions thereof are optionally substituted with one or more substituents each independently selected from the group consisting of alkyl, alkoxy, halogen, haloalkyl, haloalkoxy, hydroxy, hydroxyalkyl, cyano, amino, aminoalkyl, alkylamino, dialkylamino, and hydroxyalkylamino.

The carbon of $Z^2$ attached to the tetrahydropyridinyl and dihydropyrrolyl ring can be a chiral center. Accordingly, the configuration at those carbon atoms can be (R) or (S).

One group of compounds useful in this aspect of the present invention includes compounds of Formula I as defined above, with the following provisos when X is —CHR$^8$— and R$^8$ is hydrogen:

1) when $R^{11}$ and $R^{12}$ are both hydrogen and $R^{13}$ is aryl or arylalkyl, then the aryl portion of $R^{13}$ is substituted with at least one of haloalkyl or haloalkoxy; or 2) when Hy is a pyridin-2-yl ring, then $R^1$ is other than optionally substituted 2-aminophenylaminocarbonyl or 2-hydroxyphenylaminocarbonyl.

In one embodiment, compounds useful in the present invention are compounds of Formula I, where n is 1 (tetrahydropyridinyl).

In one embodiment, compounds useful in the present invention are compounds of Formula I, where n is 0 (dihydropyrrolyl).

In one embodiment, tetrahydropyridinyl compounds useful in the present invention are compounds of Formula I, where n is 1, X is —CHR$^8$—, and $R^8$ and $R^9$ are both hydrogen, having the Formula II:

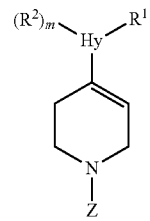

and pharmaceutically acceptable salts, prodrugs, and solvates thereof, wherein Hy, $R^1$, $R^2$, Z, and m are as defined above.

In one embodiment, tetrahydropyridinyl compounds useful in the present invention are compounds of Formula I, where n is 1, X is —CHR$^8$—, and $R^8$ and $R^9$ together form a bridge —(CH$_2$)$_p$—, having the Formula III:

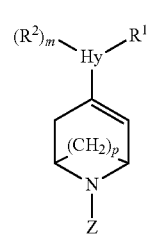

and pharmaceutically acceptable salts, prodrugs, and solvates thereof, wherein Hy, $R^1$, $R^2$, Z, m and p are as defined above.

In one embodiment, compounds useful in the present invention are compounds of Formula III, where p is 2, having the Formula IV:

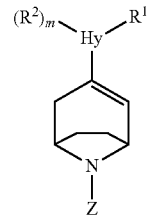

and pharmaceutically acceptable salts, prodrugs, and solvates thereof.

In another embodiment, compounds useful in the present invention are compounds of Formula III, where p is 3.

In a further embodiment, compounds useful in the present invention are compounds of Formula III, where p is 4.

In one embodiment, tetrahydropyridinyl compounds useful in the present invention are compounds of Formula I, where n is 1, X is —C(=O)—, and $R^9$ is hydrogen, having the Formula V:

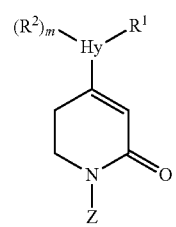

and pharmaceutically acceptable salts, prodrugs, and solvates thereof, wherein Hy, $R^1$, $R^2$, Z, and m are as defined above.

In one embodiment, dihydropyrrolyl compounds useful in the present invention are compounds of Formula I, where n is 0, X is —$CHR^8$—, and $R^8$ and $R^9$ are both hydrogen, having the Formula VI:

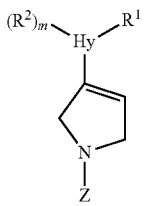

VI and pharmaceutically acceptable salts, prodrugs, and solvates thereof, wherein Hy, $R^1$, $R^2$, Z, and m are as defined above.

In one embodiment, dihydropyrrolyl compounds useful in the present invention are compounds of Formula I, where n is 0, X is —$CHR^8$—, and $R^8$ and $R^9$ together form a bridge —$(CH_2)_p$—, having the Formula VII:

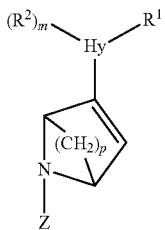

VII and pharmaceutically acceptable salts, prodrugs, and solvates thereof, wherein Hy, $R^1$, $R^2$, Z, m and p are as defined above.

In one embodiment, compounds useful in the present invention are compounds of Formula VII, where p is 2, having the Formula VIII:

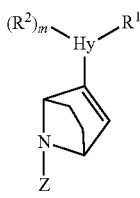

VIII and pharmaceutically acceptable salts, prodrugs, and solvates thereof.

In another embodiment, compounds useful in the present invention are compounds of Formula VII, where p is 3.

In a further embodiment, compounds useful in the present invention are compounds of Formula VII, where p is 4.

In one embodiment, dihydropyrrolyl compounds useful in the present invention are compounds of Formula I, where n is 0, X is —C(=O)—, and $R^9$ is hydrogen, having the Formula IX:

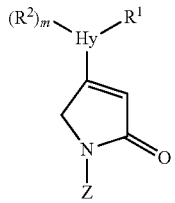

IX and pharmaceutically acceptable salts, prodrugs, and solvates thereof, wherein Hy, $R^1$, $R^2$, Z, and m are as defined above.

In one embodiment, compounds useful in the present invention are compounds of any of Formulae I-IX, where Hy is a 6-membered heteroaromatic ring having at least one nitrogen atom. In another embodiment, compounds useful in the present invention are compounds of any of Formulae I-IX, where Hy is a 5-membered heteroaromatic ring or a 5-membered heterocyclic ring having at least one nitrogen atom. Useful compounds include those where Hy is selected from the group consisting of pyridyl, pyrimidinyl, pyrazinyl, pyrrolyl, imidazolyl, triazolyl, thiazolyl, oxazolyl, isoxazolyl, and 1,2,4-oxadiazolyl. Preferably, Hy is selected from the group consisting of pyridin-2-yl, pyridin-3-yl, pyrimidin-2-yl, pyrimidin-4-yl, pyrazin-2-yl, imidazol-2-yl, imidazol-4-yl, and oxazol-2-yl. More preferably, Hy is pyridin-2-yl, pyridin-3-yl, pyrimidin-2-yl, or oxazol-2-yl.

The group $R^1$ takes the place of a hydrogen atom that would otherwise be present in any carbon atom in the Hy ring to which $R^1$ group is attached. Preferably, $R^1$ is attached to a carbon atom adjacent to a nitrogen atom in the Hy ring.

The group $R^2$ takes the place of a hydrogen atom that would otherwise be present in any carbon atom in the Hy ring to which $R^2$ group is attached. $R^1$ and $R^2$ can be attached to the same or different carbon atoms in the Hy ring.

In one embodiment, compounds useful in the present invention are compounds of any of Formulae I-IX, wherein $R^1$ is attached to a carbon atom adjacent to a nitrogen atom of the Hy ring. In one embodiment, compounds useful in this aspect of the invention include tetrahydropyridinyl compounds having the Formula X:

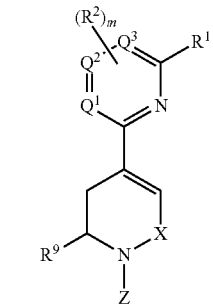

X and pharmaceutically acceptable salts, prodrugs, and solvates thereof, wherein
one of $Q^1$, $Q^2$, or $Q^3$ is N and the remaining two are each CH; or
$Q^1$, $Q^2$, and $Q^3$ are each CH; and
X, Z, $R^1$, $R^2$, $R^9$ and m are as defined above for Formula I.
In one embodiment, useful compounds of Formula X include those where one of $Q^1$, $Q^2$, or $Q^3$ is N and the remaining two are CH. In another embodiment, useful compounds of Formula X include those where $Q^1$, $Q^2$, or $Q^3$ are each CH, having the Formula XI:

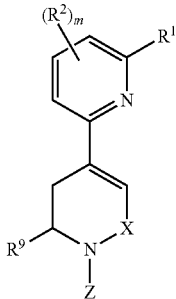

XI and pharmaceutically acceptable salts, prodrugs, and solvates thereof, wherein X, Z, $R^1$, $R^2$, $R^9$ and m are as defined above for Formula I.

In one embodiment, compounds useful in the present invention, where $R^1$ is attached to a carbon atom adjacent to a nitrogen atom of the Hy ring are compounds of Formula XII:

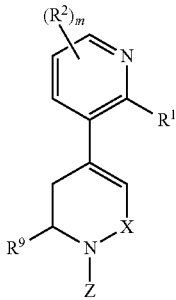

XII and pharmaceutically acceptable salts, prodrugs, and solvates thereof, wherein X, Z, $R^1$, $R^2$, $R^9$ and m are as defined above for Formula I.

In one embodiment, compounds useful in the present invention are compounds of any one of Formulae X-XII, where X is —$CHR^8$— and $R^8$ and $R^9$ both are hydrogen.

In one embodiment, compounds useful in the present invention are compounds of any one of Formulae X-XII, where X is —$CHR^8$— and $R^8$ and $R^9$ together form a bridge —$(CH_2)_p$— and p is 2, 3, or 4. Preferably, p is 2.

In one embodiment, compounds useful in the present invention are compounds of any one of Formulae X-XII, where X is —C(=O)— and $R^9$ is hydrogen.

In one embodiment, compounds useful in the present invention are compounds of any of Formulae I-XII where $R^1$ is —C(=W)$NR^3R^4$, wherein W, $R^3$, and $R^4$ are as defined above for Formula I. In one embodiment, compounds useful in the present invention are compounds of any of Formulae I-XII, wherein W is O and $R^3$ and $R^4$ are as defined above for Formula I. In another embodiment, compounds useful in the present invention are compounds of any of Formulae I-XII, wherein W is $NR^{14}$ and $R^3$, $R^4$, and $R^{14}$ are as defined above for Formula I. Preferably, $R^{14}$ is hydrogen or $C_{1-4}$ alkyl. Useful compounds include those where $R^{14}$ is hydrogen.

In one embodiment, compounds useful in the present invention are compounds of any of Formulae I-XII where $R^1$ is —C(=W)$NR^3R^4$ and $R^3$ is hydrogen or alkyl, preferably hydrogen or $C_{1-6}$ alkyl, and $R^4$ is as defined above for Formula I.

In one embodiment, compounds useful in the present invention are compounds of any of Formulae I-XII where $R^1$ is —C(=W)$NR^3R^4$ and $R^3$ is hydrogen and $R^4$ is as defined above for Formula I.

Useful compounds include those where $R^4$ is selected from the group consisting of alkyl, alkenyl, alkynyl, haloalkyl, hydroxyalkyl, cycloalkyl, (cycloalkyl)alkyl, cycloalkenyl, (cycloalkenyl)alkyl, heterocyclo, heterocycloalkyl, aryl, arylalkyl, heteroaryl, and heteroarylalkyl, wherein the cycloalkyl, cycloalkenyl, heterocyclo, aryl and heteroaryl portions are optionally substituted with one or more substituents each independently selected from the group consisting of alkyl, alkoxy, halogen, haloalkyl, haloalkoxy, hydroxy, hydroxyalkyl, cyano, amino, aminoalkyl, alkylamino, dialkylamino, and hydroxyalkylamino; and wherein $R^4$ is preferably selected from the group consisting of $C_{1-6}$ alkyl, $C_{2-6}$ alkenyl, $C_{2-6}$ alkynyl, halo($C_{1-6}$)alkyl, hydroxy($C_{1-6}$)alkyl, $C_{3-7}$ cycloalkyl, $C_{3-7}$ (cycloalkyl)($C_{1-4}$)alkyl, $C_{3-7}$ cycloalkenyl, $C_{3-7}$ (cycloalkenyl)($C_{1-4}$)alkyl, 5- or 6-membered heterocyclo, 5- or 6-membered heterocyclo($C_{1-4}$)alkyl, aryl, aryl($C_{1-4}$)alkyl, 5- or 6-membered heteroaryl, and 5- or 6-membered heteroaryl($C_{1-4}$)alkyl, wherein the cycloalkyl, cycloalkenyl, heterocyclo, aryl and heteroaryl portions thereof are optionally substituted with one or more substituents each independently selected from the group consisting of alkyl, alkoxy, halogen, haloalkyl, haloalkoxy, hydroxy, hydroxyalkyl, cyano, amino, aminoalkyl, alkylamino, dialkylamino, and hydroxyalkylamino.

More preferably, $R^4$ is selected from the group consisting of $C_{1-6}$ alkyl, $C_{2-6}$ alkenyl, halo($C_{1-6}$)alkyl, monohydroxy ($C_{1-6}$)alkyl, dihydroxy($C_{1-6}$)alkyl, $C_{3-7}$cycloalkyl, $C_{3-7}$ cycloalkyl($C_{1-4}$)alkyl, $C_{3-7}$ cycloalkenyl, $C_{3-7}$ cycloalkenyl ($C_4$alkyl, phenyl, and benzyl, wherein said phenyl or phenyl portion of said benzyl is optionally substituted with 1, 2, or 3 substituents each independently selected from the group consisting of $C_{1-6}$ alkyl, $C_{1-6}$ alkoxy, halogen, halo($C_{1-6}$)alkyl, halo($C_{1-6}$)alkoxy, hydroxy, hydroxy($C_{1-6}$)alkyl, cyano, amino, amino($C_{1-6}$)alkyl, $C_{1-6}$ alkylamino, di($C_{1-6}$)alkylamino, and hydroxy($C_{1-6}$)alkylamino. Advantageously, $R^4$ is selected from the group consisting of methyl; ethyl; propyl; isopropyl; butyl; tert-butyl; trifluoromethyl; 2,2,2-trifluoroethyl; 3,3,3-trifluoropropyl; 4,4,4-trifluorobutyl; hydroxymethyl; 2-hydroxyethyl; 3-hydroxypropyl; 1,3-dihydroxyprop-2-yl; cyclopropyl; cyclopentyl; cyclohexyl; cyclopropylmethyl; phenyl optionally substituted with 1 or 2 substituents each independently selected from the group consisting of $C_{1-6}$ alkyl, $C_{1-6}$ alkoxy, halogen, halo($C_{1-6}$)alkyl, halo($C_{1-6}$)alkoxy, hydroxy, hydroxy($C_{1-6}$)alkyl, cyano, amino, amino($C_{1-6}$)alkyl, $C_{1-6}$ alkylamino, di($C_{1-6}$)alkylamino, and hydroxy($C_{1-6}$)alkylamino; and benzyl optionally substituted with 1 or 2 substituents each independently selected from the group consisting of $C_{1-6}$ alkyl, $C_{1-6}$ alkoxy, halogen, halo($C_{1-6}$)alkyl, halo($C_{1-6}$)alkoxy, hydroxy, hydroxy($C_{1-6}$)alkyl, cyano, amino, amino($C_{1-6}$)alkyl, $C_{1-6}$ alkylamino, di($C_{1-6}$)alkylamino, and hydroxy($C_{1-6}$)alkylamino.

In one embodiment, compounds useful in the present invention are compounds of any of Formulae I-XII where $R^1$ is —C(=O)$OR^5$, wherein $R^5$ is hydrogen or alkyl, preferably $C_{1-6}$ alkyl, and more preferably $C_{1-4}$ alkyl.

In one embodiment, compounds useful in the present invention are compounds of any of Formulae I-XII where $R^1$ is —$NR^6$—C(=O)$R^7$, wherein $R^6$ and $R^7$ are as defined above for Formula I. Useful compounds include those where $R^6$ is hydrogen or $C_{1-6}$ alkyl, preferably hydrogen or $C_{1-4}$ alkyl, and more preferably hydrogen, and $R^7$ is as defined above for Formula I. Useful compounds include those where $R^7$ is selected from the group consisting of alkyl, alkenyl, alkynyl, haloalkyl, hydroxyalkyl, cycloalkyl, (cycloalkyl)alkyl, cycloalkenyl, (cycloalkenyl)alkyl, heterocyclo, heterocycloalkyl, aryl, arylalkyl, heteroaryl, and heteroarylalkyl, wherein the cycloalkyl, cycloalkenyl, heterocyclo, aryl and heteroaryl portions are optionally substituted with one or more substituents each independently selected from the group consisting of alkyl, alkoxy, halogen, haloalkyl, haloalkoxy, hydroxy, hydroxyalkyl, cyano, amino, aminoalkyl, alkylamino, dialkylamino, and hydroxyalkylamino; preferably selected from the group consisting of $C_{1-6}$ alkyl, $C_{2-6}$ alkenyl, $C_{2-6}$ alkynyl, halo($C_{1-6}$)alkyl, hydroxy($C_{1-6}$) alkyl, $C_{3-7}$ cycloalkyl, $C_{3-7}$ (cycloalkyl)($C_{1-4}$)alkyl, $C_{3-7}$ cycloalkenyl, $C_{3-7}$ (cycloalkenyl)($C_{1-4}$)alkyl, 5- or 6-membered heterocyclo, 5- or 6-membered heterocyclo($C_{1-4}$)alkyl, aryl, aryl($C_{1-4}$alkyl, 5- or 6-membered heteroaryl, and 5- or 6-membered heteroaryl($C_{1-4}$alkyl, wherein the cycloalkyl, cycloalkenyl, heterocyclo, aryl and heteroaryl portions thereof are optionally substituted with one or more substituents each independently selected from the group consisting of alkyl, alkoxy, halogen, haloalkyl, haloalkoxy, hydroxy, hydroxyalkyl, cyano, amino, aminoalkyl, alkylamino, dialkylamino, and hydroxyalkylamino.

More preferably, $R^7$ is selected from the group consisting of $C_{1-6}$ alkyl, $C_{2-6}$ alkenyl, halo($C_{1-6}$)alkyl, monohydroxy ($C_{1-6}$)alkyl, dihydroxy($C_{1-6}$)alkyl, $C_{3-7}$ cycloalkyl, $C_{3-7}$ cycloalkyl($C_{1-4}$)alkyl, $C_{3-7}$ cycloalkenyl, $C_{3-7}$ cycloalkenyl ($C_{1-4}$)alkyl, phenyl, and benzyl, wherein said phenyl or phenyl portion of said benzyl is optionally substituted with 1, 2, or 3 substituents each independently selected from the group consisting of $C_{1-6}$ alkyl, $C_{1-6}$ alkoxy, halogen, halo($C_{1-6}$) alkyl, halo($C_{1-6}$)alkoxy, hydroxy, hydroxy($C_{1-6}$)alkyl, cyano, amino, amino($C_{1-6}$)alkyl, $C_{1-6}$ alkylamino, di($C_{1-6}$)alkylamino, and hydroxy($C_{1-6}$)alkylamino. Advantageously, $R^7$ is selected from the group consisting of methyl; ethyl; propyl; isopropyl; butyl; tert-butyl; trifluoromethyl; 2,2,2-trifluoroethyl; 3,3,3-trifluoropropyl; 4,4,4-trifluorobutyl; hydroxymethyl; 2-hydroxyethyl; 3-hydroxypropyl; 1,3-dihydroxyprop-2-yl; cyclopropyl; cyclopentyl; cyclohexyl; cyclopropylmethyl; phenyl optionally substituted with 1 or 2 substituents each independently selected from the group consisting of $C_{1-6}$ alkyl, $C_{1-6}$ alkoxy, halogen, halo($C_{1-6}$)alkyl, halo($C_{1-6}$)alkoxy, hydroxy, hydroxy($C_{1-6}$)alkyl, cyano, amino, amino($C_{1-6}$)alkyl, $C_{1-6}$ alkylamino, di($C_{1-6}$)alkylamino, and hydroxy($C_{1-6}$)alkylamino; and benzyl optionally substituted with 1 or 2 substituents each independently selected from the group consisting of $C_{1-6}$ alkyl, $C_{1-6}$ alkoxy, halogen, halo($C_{1-6}$)alkyl, halo($C_{1-6}$)alkoxy, hydroxy, hydroxy($C_{1-6}$)alkyl, cyano, amino, amino($C_{1-6}$)alkyl, $C_{1-6}$ alkylamino, di($C_{1-6}$)alkylamino, and hydroxy($C_{1-6}$)alkylamino.

In one embodiment, compounds useful in the present invention are compounds of any of Formulae I-XII where $R^1$ is cyano.

In one embodiment, compounds useful in the present invention are compounds of any of Formulae I-XII where $R^1$ is hydroxyalkyl. Useful compounds include those where $R^1$ is monohydroxy($C_{1-6}$)alkyl or dihydroxy($C_{1-6}$)alkyl, such as hydroxymethyl, hydroxyethyl, 1-hydroxypropyl, and 1,3-dihydroxyprop-2-yl.

In one embodiment, compounds useful in the present invention are compounds of any of Formulae I-XII where $R^1$ is a 5-membered, N-containing heteroaryl or a 5-membered, partially unsaturated, N-containing heterocyclo each of which is optionally substituted with one or two substituents each independently selected from the group consisting of alkyl, alkoxy, halogen, haloalkyl, haloalkoxy, hydroxy, hydroxyalkyl, cyano, amino, aminoalkyl, alkylamino, and dialkylamino. Useful compounds are compounds of any of Formulae I-XII where $R^1$ is selected from the group consisting of oxazolyl; 1,2,4-oxadiazolyl; 1,3,4-oxadiazolyl, and thiazolyl, any of which is optionally substituted with one or two substituents independently selected from the group consisting of alkyl, alkoxy, halogen, haloalkyl, haloalkoxy, hydroxy, hydroxyalkyl, cyano, amino, aminoalkyl, alkylamino, and dialkylamino; preferably independently selected from the group consisting of $C_{1-6}$ alkyl, $C_{1-6}$ alkoxy, halogen, halo($C_{1-6}$)alkyl, halo($C_{1-6}$)alkoxy, hydroxy, hydroxy($C_{1-6}$) alkyl, cyano, amino, amino($C_{1-6}$)alkyl, $C_{1-6}$ alkylamino, and di($C_{1-6}$)alkylamino; more preferably independently selected from the group consisting of $C_{1-4}$ alkyl, $C_{1-4}$ alkoxy, halogen, halo($C_{1-4}$)alkyl, halo($C_{1-6}$)alkoxy, hydroxy, hydroxy($C_{1-4}$) alkyl, cyano, amino, amino($C_{1-4}$)alkyl, $C_{1-2}$ alkylamino; and di($C_{1-2}$)alkylamino.

In one embodiment, compounds useful in the present invention are compounds of any of Formulae I-XII, wherein $R^1$ is selected from the group consisting of

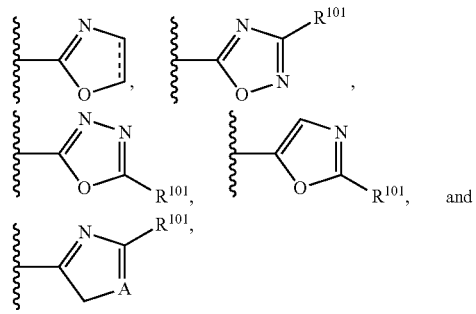

wherein $R^{101}$ is selected from the group consisting of alkyl, alkoxy, halogen, haloalkyl, haloalkoxy, hydroxy, hydroxyalkyl, cyano, amino, aminoalkyl, alkylamino, and dialkylamino; preferably selected from the group consisting of $C_{1-6}$ alkyl, $C_{1-6}$ alkoxy, halogen, halo($C_{1-6}$)alkyl, hydroxy, hydroxy($C_{1-6}$)alkyl, cyano, amino, amino($C_{1-6}$)alkyl, $C_{1-6}$ alkylamino, and di($C_{1-6}$)alkylamino; more preferably selected from the group consisting of $C_{1-4}$ alkyl, $C_{1-4}$ alkoxy, halogen, halo($C_{1-4}$alkyl, hydroxy, hydroxy($C_{1-4}$)alkyl, cyano, amino, amino($C_{1-4}$alkyl, $C_{1-2}$ alkylamino, and di ($C_{1-2}$)alkylamino; A is O or S; and ---- is an optional bond forming a double bond.

In one embodiment, compounds useful in the present invention are compounds of any of Formulae I-XII where m is 0, 1, or 2, and preferably m is 0 or 1. Useful compounds include those where $R^2$ is selected from the group consisting of $C_{1-4}$ alkyl, halo($C_{1-4}$)alkyl, halogen, hydroxy($C_{1-4}$)alkyl, hydroxy, $C_{1-4}$ alkoxy, $C_{1-4}$ alkoxy($C_{1-4}$)alkyl, halo($C_{1-4}$) alkoxy, halo($C_{1-4}$)alkoxy($C_{1-4}$)alkyl, nitro, cyano, amino, $C_{1-4}$ alkylamino, and di($C_{1-4}$)alkylamino. Advantageously, $R^2$ is selected from the group consisting of $C_{1-4}$ alkyl, halo ($C_{1-4}$)alkyl, halogen, hydroxy($C_{1-4}$)alkyl, hydroxy, $C_{1-4}$ alkoxy, halo($C_{1-4}$)alkoxy, halo($C_{1-4}$)alkoxy($C_{1-4}$)alkyl, nitro, cyano, and amino; preferably selected from the group consisting of $C_{1-4}$ alkyl, monohalo($C_{1-4}$)alkyl, trihalo($C_{1-4}$)alkyl, halogen, monohydroxy($C_{1-4}$)alkyl, dihydroxy($C_{1-4}$)alkyl, hydroxy, $C_{1-4}$alkoxy, trihalo($C_{1-4}$)alkoxy, trihalo($C_{1-4}$) alkoxy($C_{1-4}$)alkyl, nitro, cyano, and amino; and more preferably selected from the group consisting of methyl, ethyl, propyl, iso-propyl, butyl, tert-butyl, fluoromethyl, trifluoromethyl, 2,2,2-trifluoroethyl, 3,3,3-trifluoropropyl, fluoro, chloro, bromo, hydroxymethyl, 2-hydroxyethyl, 1,3-dihydroxyprop-2-yl, hydroxy, trifluoromethoxy, 2,2,2-trifluoroethoxy, trifluoromethoxymethyl, nitro, cyano, and amino.

In one embodiment, compounds useful in the present invention are compounds of any of Formulae I-XII where Z is $Z^1$, that is —$SO_2$—$R^{10}$. Useful compounds include those where $R^{10}$ is selected from the group consisting of $C_{4-8}$ alkyl, halo($C_{3-6}$)alkyl, $C_{5-12}$ cycloalkyl, ($C_{3-12}$ cycloalkyl)alkyl, $C_{5-12}$ cycloalkenyl, ($C_{3-12}$ cycloalkenyl)alkyl, heterocyclo, heterocycloalkyl, aryl, arylalkyl, heteroaryl, heteroarylalkyl, arylamino, and aryl(alkyl)amino, wherein the cycloalkyl, cycloalkenyl, heterocyclo, aryl and heteroaryl portions thereof are optionally substituted with one or more substituents each independently selected from the group consisting of alkyl, alkoxy, halogen, haloalkyl, haloalkoxy, hydroxy, hydroxyalkyl, cyano, amino, aminoalkyl, alkylamino, dialkylamino, and hydroxyalkylamino. Preferably, $R^{10}$ is selected from the group consisting of $C_{4-6}$ alkyl, monohalo($C_{3-6}$)alkyl, dihalo($C_{3-6}$)alkyl, trihalo($C_{3-6}$)alkyl, $C_{5-8}$ cycloalkyl, $C_{3-8}$ cycloalkyl($C_{1-2}$)alkyl, $C_{5-8}$ cycloalkenyl, $C_{3-8}$ cycloalkenyl($C_{1-2}$)alkyl, 5- or 6-membered heterocyclo, 5- or 6-membered heterocyclo($C_{1-2}$)alkyl, $C_{6-14}$ aryl, $C_{6-14}$ aryl($C_{1-2}$)alkyl, 5- or 6-membered heteroaryl, and 5- or 6-membered heteroaryl ($C_{1-2}$)alkyl, wherein the cycloalkyl, cycloalkenyl, heterocyclo, aryl and heteroaryl portions are optionally substituted with 1, 2, or 3 substituents each independently selected from the group consisting of $C_{1-4}$ alkyl, $C_{1-4}$ alkoxy, halogen, halo ($C_{1-4}$)alkyl, halo($C_{1-4}$)alkoxy, hydroxy, hydroxy($C_{1-4}$)alkyl, cyano, amino, amino($C_{1-4}$)alkyl, $C_{1-4}$ alkylamino, di($C_{1-4}$) alkylamino, and hydroxy($C_{1-4}$)alkylamino.

Useful compounds include those where $R^{10}$ is selected from the group consisting of $C_{4-6}$ alkyl; trifluoro($C_{3-6}$)alkyl; $C_{5-8}$ cycloalkyl; $C_{3-8}$ cycloalkyl($C_{1-2}$)alkyl; $C_{5-8}$ cycloalkenyl; $C_{3-8}$ cycloalkenyl($C_{1-2}$)alkyl; heterocyclo selected from the group consisting of pyrrolidinyl, piperidinyl, hexahydropyrimidinyl, oxazolidinyl, and tetrahydrothienyl; heterocyclo($C_{1-2}$)alkyl selected from the group consisting of pyrrolidinyl($C_{1-2}$)alkyl, piperidinyl($C_{1-2}$)alkyl, hexahydropyrimidinyl($C_{1-2}$)alkyl, oxazolidinyl($C_{1-2}$)alkyl, and tetrahydrothienyl($C_{1-2}$)alkyl; $C_{6-10}$ aryl; $C_{6-10}$ aryl($C_{1-2}$) alkyl; heteroaryl selected from the group consisting of pyrrolyl, pyridyl, pyrimidyl, isoxazolyl, oxazolyl, and thienyl; and heteroaryl($C_{1-2}$)alkyl selected from the group consisting of pyrrolyl($C_{1-2}$)alkyl, pyridyl($C_{1-2}$)alkyl, pyrimidyl($C_{1-2}$) alkyl, isoxazolyl($C_{1-2}$)alkyl, oxazolyl($C_{1-2}$)alkyl, and thienyl ($C_{1-2}$)alkyl; wherein the cycloalkyl, cycloalkenyl, heterocyclo, aryl and heteroaryl portions thereof are optionally substituted with 1, 2, or 3 substituents each independently selected from the group consisting of $C_{1-4}$ alkyl, $C_{1-4}$ alkoxy, halogen, halo($C_{1-4}$)alkyl, halo($C_{1-4}$)alkoxy, hydroxy, hydroxy(C cyano, amino, amino($C_{1-4}$)alkyl, $C_{1-4}$ alkylamino, di($C_{1-4}$)alkylamino, and hydroxy($C_{1-4}$)alkylamino.

Advantageously, $R^{10}$ is selected from the group consisting of a) cyclohexyl;
b) cycloheptyl;
c) cyclohexylmethyl;
d) cycloheptylmethyl;
e) phenyl, unsubstituted or substituted with 1, 2 or 3 substituents each independently selected from the group consisting of $C_{1-4}$ alkyl, $C_{1-4}$ alkoxy, halogen, halo($C_{1-4}$)alkyl, halo ($C_4$alkoxy, hydroxy, hydroxy($C_{1-4}$)alkyl, cyano, amino, amino($C_{1-4}$)alkyl, $C_{1-4}$ alkylamino, di($C_{1-4}$)alkylamino, and hydroxy($C_{1-4}$)alkylamino, and preferably substituted with 1, 2 or 3 substituents each independently selected from the group consisting of halogen, halo($C_{1-4}$)alkyl, halo($C_{1-4}$) alkoxy, and cyano;

f) benzyl, unsubstituted or substituted with 1, 2 or 3 substituents each independently selected from the group consisting of $C_{1-4}$ alkyl, $C_{1-4}$ alkoxy, halogen, halo($C_{1-4}$)alkyl, halo ($C_{1-4}$)alkoxy, hydroxy, hydroxy($C_{1-4}$)alkyl, cyano, amino, amino($C_{1-4}$)alkyl, $C_{1-4}$ alkylamino, di($C_{1-4}$)alkylamino, and hydroxy($C_{1-4}$)alkylamino, and preferably substituted with 1, 2 or 3 substituents each independently selected from the group consisting of halogen, halo($C_{1-4}$)alkyl, halo($C_{1-4}$) alkoxy, and cyano;

g) phenylethyl, unsubstituted or substituted with 1, 2 or 3 substituents each independently selected from the group consisting of $C_{1-4}$ alkyl, $C_{1-4}$ alkoxy, halogen, halo($C_{1-4}$)alkyl, halo($C_{1-4}$)alkoxy, hydroxy, hydroxyl($C_{1-4}$)alkyl, cyano, amino, amino($C_{1-4}$)alkyl, $C_{1-4}$ alkylamino, di($C_{1-4}$)alkylamino, and hydroxy($C_{1-4}$)alkylamino, and preferably substituted with 1, 2 or 3 substituents each independently selected from the group consisting of halogen, halo($C_{1-4}$)alkyl, halo ($C_{1-4}$)alkoxy, and cyano;

h) pyridin-1-yl, pyridin-2-yl, or pyridin-3-yl, unsubstituted or substituted with 1 or 2 substituents each independently selected from the group consisting of halogen, halo($C_{1-4}$) alkyl, halo($C_{1-4}$)alkoxy, and cyano;

i) thiophen-2-yl or thiophen-3-yl, unsubstituted or substituted with 1 or 2 substituents each independently selected from the group consisting of halogen, halo($C_{1-4}$)alkyl, halo ($C_{1-4}$)alkoxy, and cyano;

j) isoxazol-3-yl, isoxazol-4-yl, or isoxazol-5-yl, unsubstituted or substituted with 1 or 2 substituents each independently selected from the group consisting of halogen, halo ($C_{1-4}$)alkyl, halo($C_{1-4}$)alkoxy, and cyano;

k) oxazol-2-yl, oxazol-4-yl, or oxazol-5-yl, unsubstituted or substituted with 1 or 2 substituents each independently selected from the group consisting of halogen, halo($C_{1-4}$) alkyl, halo($C_{1-4}$)alkoxy, and cyano; and l) isoxazol-3-ylmethyl, isoxazol-4-ylmethyl, or isoxazol-5-ylmethyl, unsubstituted or substituted with 1 or 2 substituents each independently selected from the group consisting of halogen, halo($C_{1-4}$)alkyl, halo($C_{1-4}$)alkoxy, and cyano.

In one embodiment, $R^{10}$ is a substituted phenyl, benzyl, or phenylethyl, preferably phenyl, and the substituent is at the 2-position of the phenyl portion. Preferably, the substituent is halogen, trifluoromethyl, trifluoromethoxy, or cyano.

In one embodiment, $R^{10}$ is a substituted phenyl, benzyl, or phenylethyl, preferably phenyl, and the substituent is at the 3-position of the phenyl portion. Preferably, the substituent is halogen, trifluoromethyl, trifluoromethoxy, cyano.

In one embodiment, $R^{10}$ is a substituted phenyl, benzyl, or phenylethyl, preferably phenyl, and the substituent is at the 4-position of the phenyl portion. Preferably, the substituent is halogen, trifluoromethyl, trifluoromethoxy, or cyano.

Advantageously, when $R^{10}$ is a substituted phenyl, benzyl, or phenylethyl, the substituent is at the 3-position of the phenyl portion.

In one embodiment, compounds useful in the present invention are compounds of any of Formulae I-XII where Z is $Z^2$, that is, —$C(R^{11}R^{12})R^{13}$. In one embodiment, compounds useful in the present invention are compounds of any of Formulae I-XII, wherein $R^{11}$ and $R^{12}$ are both hydrogen and $R^{13}$ is as defined above for Formula I. In this aspect of the invention, when X is —$CHR^8$— and $R^8$ is hydrogen and $R^{13}$ is aryl or arylalkyl, then the aryl portion thereof is substituted by at least one of haloalkyl or haloalkoxy, and especially trifluoromethyl or trifluoromethoxy. In one aspect of the present invention, when X is —$CHR^8$— and $R^8$ and $R^9$ form a bridge $(CH_2)_p$ with p=2 or 3, Z is $Z^2$, $R^{11}$ and $R^{12}$ are both hydrogen, and $R^{13}$ is aryl or arylalkyl, then $R^1$ is not cyano or a 5-membered, N-containing heteroaryl. In one aspect of the present invention, when Hy is a 6-membered heteroaromatic ring, $R^1$ is —C(=W)$NR^3R^4$, Z=$Z^2$, and $R^{11}$ and $R^{12}$ are both hydrogen, then $R^{13}$ is an aryl, arylalkyl, heteroaryl or heteroarylalkyl, wherein the aryl portion is not fluorenyl and consists of a monocyclic or bicyclic ring structure that is optionally substituted with one or more substituents each independently selected from the group consisting of alkyl, alkoxy, halogen, haloalkyl, haloalkoxy, hydroxy, hydroxyalkyl, cyano, amino, aminoalkyl, alkylamino, dialkylamino, and hydroxyalkylamino.

In one embodiment, compounds useful in the present invention are compounds of any of Formulae I-XII, wherein $R^{11}$ is hydrogen, $R^{12}$ is selected from the group consisting of alkyl, haloalkyl, hydroxyalkyl, halogen, hydroxy, alkoxy, alkoxyalkyl, haloalkoxy, haloalkoxyalkyl, cyano, amino, aminoalkyl, alkylaminoalkyl, and dialkylaminoalkyl, and $R^{13}$ is as defined above for Formula I.

In one embodiment, compounds useful in the present invention are compounds of any of Formulae I-XII, wherein $R^{11}$ and $R^{12}$ are each independently selected from the group consisting of alkyl, haloalkyl, hydroxyalkyl, halogen, hydroxy, alkoxy, alkoxyalkyl, haloalkoxy, haloalkoxyalkyl, cyano, amino, aminoalkyl, alkylaminoalkyl, and dialkylaminoalkyl, and $R^{13}$ is as defined above for Formula I.

Useful compounds include those where $R^{11}$ and $R^{12}$, when other than hydrogen, are each independently selected from the group consisting of $C_{1-4}$ alkyl, halo($C_{1-4}$)alkyl, hydroxy($C_{1-4}$)alkyl, halogen, hydroxy, $C_{1-4}$ alkoxy, $C_{1-4}$ alkoxy($C_{1-4}$)alkyl, halo($C_{1-4}$)alkoxy, halo($C_{1-4}$)alkoxy($C_{1-4}$)alkyl, cyano, amino, amino($C_{1-4}$)alkyl, $C_{1-4}$ alkylamino($C_{1-4}$)alkyl, and di($C_{1-4}$)alkylamino($C_{1-4}$)alkyl; preferably each independently selected from the group consisting of $C_{1-4}$ alkyl, halo($C_{1-4}$)alkyl, hydroxy($C_{1-4}$)alkyl, halogen, hydroxy, halo($C_{1-4}$)alkoxy, and halo($C_{1-4}$)alkoxy($C_{1-4}$)alkyl; more preferably each independently selected from the group consisting of methyl, ethyl, propyl, iso-propyl, butyl, tert-butyl, trifluoromethyl, 2,2,2-trifluoroethyl, 3,3,3-trifluoropropyl, hydroxymethyl, 2-hydroxyethyl, 1,3-dihydroxyprop-2-yl, fluoro, chloro, bromo, trifluoromethoxy, 2-trifluoroethoxy, and trifluoromethoxymethyl.

Useful compounds include those where $R^{13}$ is selected from the group consisting of $C_{6-10}$ aryl, $C_{6-10}$ aryl($C_{1-2}$)alkyl, 5- or 6-membered heteroaryl, and 5- or 6-membered heteroaryl($C_{1-2}$)alkyl, wherein the aryl and heteroaryl portions thereof are optionally substituted with one or more substituents each independently selected from the group consisting of alkyl, alkoxy, halogen, haloalkyl, haloalkoxy, hydroxy, hydroxyalkyl, cyano, amino, aminoalkyl, alkylamino, dialkylamino, and hydroxyalkylamino; and preferably optionally substituted with 1, 2, or 3 substituents each independently selected from the group consisting of $C_{1-4}$ alkyl, $C_{1-4}$ alkoxy, halogen, halo($C_{1-4}$)alkyl, halo($C_{1-4}$)alkoxy, hydroxy, hydroxy($C_{1-4}$)alkyl, cyano, amino, amino($C_{1-4}$)alkyl, $C_{1-4}$ alkylamino, di($C_{1-4}$)alkylamino, and hydroxy($C_{1-4}$)alkylamino. Preferably, $R^{13}$ is phenyl, benzyl, phenylethyl, pyrrolyl, pyridyl, pyrimidyl, isoxazolyl, oxazolyl, thienyl, pyrrolyl($C_{1-2}$)alkyl, pyridyl($C_{1-2}$)alkyl, pyrimidyl($C_{1-2}$)alkyl, isoxazolyl($C_{1-2}$)alkyl, oxazolyl($C_{1-2}$)alkyl, or thienyl($C_{1-2}$)alkyl, wherein the aryl and heteroaryl portions thereof are optionally substituted with 1, 2, or 3 substituents each independently selected from the group consisting of $C_{1-4}$ alkyl, $C_{1-4}$ alkoxy, halogen, halo($C_{1-4}$)alkyl, halo($C_{1-4}$)alkoxy, hydroxy, hydroxy($C_{1-4}$)alkyl, cyano, amino, amino($C_{1-4}$) alkyl, $C_{1-4}$ alkylamino, di($C_{1-4}$alkylamino, and hydroxy ($C_{1-4}$)alkylamino.

Advantageously, $R^{13}$ is selected from the group consisting of a) phenyl, unsubstituted or substituted with 1, 2 or 3 substituents each independently selected from the group consisting of $C_{1-4}$ alkyl, $C_{1-4}$ alkoxy, halogen, halo($C_{1-4}$)alkyl, halo ($C_{1-4}$)alkoxy, hydroxy, hydroxy($C_{1-4}$)alkyl, cyano, amino, amino($C_{1-4}$)alkyl, $C_{1-4}$ alkylamino, di($C_{1-4}$)alkylamino, and hydroxy($C_{1-4}$)alkylamino, and preferably substituted with 1, 2 or 3 substituents each independently selected from the group consisting of halogen, halo($C_{1-4}$alkyl, halo($C_{1-4}$) alkoxy, and cyano;

b) benzyl, unsubstituted or substituted with 1, 2 or 3 substituents each independently selected from the group consisting of $C_{1-4}$ alkyl, $C_{1-4}$ alkoxy, halogen, halo($C_{1-4}$)alkyl, halo ($C_{1-4}$alkoxy, hydroxy, hydroxy($C_{1-4}$)alkyl, cyano, amino, amino($C_{1-4}$)alkyl, $C_{1-4}$ alkylamino, di($C_{1-4}$)alkylamino, and hydroxy($C_{1-4}$)alkylamino, and preferably substituted with 1, 2 or 3 substituents each independently selected from the group consisting of halogen, halo($C_{1-4}$alkyl, halo($C_{1-4}$) alkoxy, and cyano;

c) phenylethyl, unsubstituted or substituted with 1, 2 or 3 substituents each independently selected from the group consisting of $C_{1-4}$ alkyl, $C_{1-4}$ alkoxy, halogen, halo($C_{1-4}$)alkyl, halo($C_{1-4}$)alkoxy, hydroxy, hydroxy($C_{1-4}$)alkyl, cyano, amino, amino($C_{1-4}$)alkyl, $C_{1-4}$ alkylamino, di($C_{1-4}$)alkylamino, and hydroxy($C_{1-4}$)alkylamino, and preferably substituted with 1, 2 or 3 substituents each independently selected from the group consisting of halogen, halo($C_{1-4}$)alkyl, halo ($C_{1-4}$)alkoxy, and cyano;

d) pyridin-1-yl, pyridin-2-yl, or pyridin-3-yl, unsubstituted or substituted with 1 or 2 substituents each independently selected from the group consisting of halogen, halo($C_{1-4}$) alkyl, halo($C_{1-4}$)alkoxy, and cyano;

e) thiophen-2-yl or thiophen-3-yl, unsubstituted or substituted with 1 or 2 substituents each independently selected from the group consisting of halogen, halo($C_{1-4}$)alkyl, halo ($C_{1-4}$)alkoxy, and cyano;

f) isoxazol-3-yl, isoxazol-4-yl, or isoxazol-5-yl, unsubstituted or substituted with 1 or 2 substituents each independently selected from the group consisting of halogen, halo ($C_{1-4}$)alkyl, halo($C_{1-4}$)alkoxy, and cyano;

g) oxazol-2-yl, oxazol-4-yl, or oxazol-5-yl, unsubstituted or substituted with 1 or 2 substituents each independently selected from the group consisting of halogen, halo($C_{1-4}$) alkyl, halo($C_{1-4}$)alkoxy, and cyano; and h) isoxazol-3-ylmethyl, isoxazol-4-ylmethyl, or isoxazol-5-ylmethyl, unsubstituted or substituted with 1 or 2 substituents each independently selected from the group consisting of halogen, halo($C_{1-4}$)alkyl, halo($C_{1-4}$)alkoxy, and cyano.

In one embodiment, $R^{13}$ is a substituted phenyl, benzyl, or phenylethyl, preferably phenyl, and the substituent is at the 4-position of the phenyl portion. Preferably, the substituent is halogen, trifluoromethyl, trifluoromethoxy, or cyano.

In one embodiment, compounds useful in the present invention are compounds of Formula XI or XII, wherein Z is $Z^1$, and X, $R^1$, $R^2$, $R^9$, m, and $R^{19}$ are as defined for Formula I. Preferably, in these compounds, $R^{19}$ is phenyl substituted with 1, 2 or 3 substituents each independently selected from the group consisting of $C_{1-4}$ alkyl, $C_{1-4}$ alkoxy, halogen, halo ($C_{1-4}$)alkyl, halo($C_{1-4}$)alkoxy, hydroxy, hydroxy($C_{1-4}$)alkyl, cyano, amino, amino($C_{1-4}$)alkyl, $C_{1-4}$ alkylamino, di($C_{1-4}$) alkylamino, and hydroxy($C_{1-4}$)alkylamino; and preferably substituted with 1, 2 or 3 substituents each independently selected from the group consisting of halogen, halo($C_{1-4}$)

alkyl, halo($C_{1-4}$)alkoxy, and cyano; more preferably substituted with 1, 2, or 3 substituents each independently selected from the group consisting of fluoro, chloro, trifluoromethyl, trifluoromethoxy, and cyano. Useful compounds include those where m is 0 or 1, and $R^2$ is selected from the group consisting of chloro, fluoro and bromo. Advantageously, in these compounds, $R^1$ is —C(=W)$NR^3R^4$, wherein W, $R^3$ and $R^4$ are as defined above for Formula I.

In one embodiment, compounds useful in the present invention are compounds of Formula XI or XII, wherein
$R^1$ is —C(=W)$NR^3R^4$, wherein
W is O;
$R^3$ is hydrogen; and
$R^4$ is $C_{1-6}$ alkyl, $C_{2-6}$ alkenyl, halo($C_{1-6}$)alkyl, monohydroxy($C_{1-6}$)alkyl, dihydroxy($C_{1-6}$)alkyl, $C_{3-7}$ cycloalkyl, $C_{3-7}$ cycloalkyl($C_{1-4}$)alkyl, $C_{3-7}$ cycloalkenyl, $C_{3-7}$ cycloalkenyl($C_{1-4}$)alkyl, phenyl, or benzyl, wherein the cycloalkyl, cycloalkenyl, and phenyl portions thereof are optionally substituted with 1, 2, or 3 substituents each independently selected from the group consisting of alkyl, alkoxy, halogen, haloalkyl, haloalkoxy, hydroxy, hydroxyalkyl, cyano, amino, aminoalkyl, alkylamino, dialkylamino, and hydroxyalkylamino;
$R^2$ is fluoro, chloro or bromo;
m is 0 or 1;
X is —$CHR^8$—;
$R^8$ and $R^9$ are both hydrogen or together form a bridge —$(CH_2)_p$—, wherein
p is 2, 3, or 4; and
Z is $Z^1$; and $R^{10}$ is phenyl substituted with 1, 2 or 3 substituents each independently selected from the group consisting of $C_{1-4}$ alkyl, $C_{1-4}$ alkoxy, halogen, halo($C_{1-4}$)alkyl, halo ($C_{1-4}$alkoxy, hydroxy, hydroxy($C_{1-4}$)alkyl, cyano, amino, amino($C_{1-4}$)alkyl, $C_{1-4}$ alkylamino, di($C_{1-4}$)alkylamino, and hydroxy($C_{1-4}$)alkylamino. In one embodiment, $R^8$ and $R^9$ are both hydrogen. In another embodiment, $R^8$ and $R^9$ together form a bridge —$(CH_2)_p$—.

In one embodiment, compounds useful in the present invention are compounds of Formula XI or XII, wherein
$R^1$ is —C(=W)$NR^3R^4$, wherein
W is O;
$R^3$ is hydrogen; and
$R^4$ is $C_{1-6}$ alkyl, $C_{2-6}$ alkenyl, halo($C_{1-6}$)alkyl, monohydroxy($C_{1-6}$)alkyl, dihydroxy($C_{1-6}$)alkyl, $C_{3-7}$ cycloalkyl, $C_{3-7}$ cycloalkyl($C_{1-4}$)alkyl, $C_{3-7}$ cycloalkenyl, $C_{3-7}$ cycloalkenyl($C_{1-4}$)alkyl, phenyl, or benzyl, wherein the cycloalkyl, cycloalkenyl, and phenyl portions thereof are optionally substituted with 1, 2, or 3 substituents each independently selected from the group consisting of alkyl, alkoxy, halogen, haloalkyl, haloalkoxy, hydroxy, hydroxyalkyl, cyano, amino, aminoalkyl, alkylamino, dialkylamino, and hydroxyalkylamino;
$R^2$ is fluoro, chloro or bromo;
m is 0 or 1;
X is —C(=O)—;
$R^9$ is hydrogen; and
Z is $Z^1$; and $R^{10}$ is phenyl substituted with 1, 2 or 3 substituents each independently selected from the group consisting of $C_{1-4}$ alkyl, $C_{1-4}$ alkoxy, halogen, halo($C_{1-4}$)alkyl, halo ($C_{1-4}$)alkoxy, hydroxy, hydroxy($C_{1-4}$alkyl, cyano, amino, amino($C_{1-4}$)alkyl, $C_{1-4}$ alkylamino, di($C_{1-4}$)alkylamino, and hydroxy($C_{1-4}$)alkylamino.

Optional substituents attached to aryl, phenyl, and heteroaryl rings each take the place of a hydrogen atom that would otherwise be present in any position on the aryl, phenyl or heteroaryl rings.

Exemplary preferred compounds useful in the present invention include:
1'-(3-trifluoromethylbenzenesulfonyl)-1',2',3',6'-tetrahydro-[2,4']bipyridinyl-6-carboxylic acid cyclopropylamide;
1'-(4-trifluoromethoxybenzenesulfonyl)-1',2',3',6'-tetrahydro-[2,4']bipyridinyl-6-carboxylic acid cyclopropylamide;
1'-(3-chlorobenzenesulfonyl)-1',2',3',6'-tetrahydro-[2,4']bipyridinyl-6-carboxylic acid cyclopropylamide;
1'-(2-trifluoromethylbenzenesulfonyl)-1',2',3',6'-tetrahydro-[2,4']bipyridinyl-6-carboxylic acid cyclopropylamide;
1'-(4-trifluoromethylbenzenesulfonyl)-1',2',3',6'-tetrahydro-[2,4']bipyridinyl-6-carboxylic acid cyclopropylamide;
1'-(4-fluorobenzenesulfonyl)-1',2',3',6'-tetrahydro-[2,4']bipyridinyl-6-carboxylic acid cyclopropylamide;
1'-(3-cyanobenzenesulfonyl)-1',2',3',6'-tetrahydro-[2,4']bipyridinyl-6-carboxylic acid cyclopropylamide;
1'-dimethylsulfamoyl-1',2',3',6'-tetrahydro-[2,4']bipyridinyl-6-carboxylic acid cyclopropylamide;
1'-(3,3,3-trifluoropropylsulfonyl)-1',2',3',6'-tetrahydro-[2,4']bipyridinyl-6-carboxylic acid cyclopropylamide;
1'-cyclohexylsulfonyl-1',2',3',6'-tetrahydro-[2,4']bipyridinyl-6-carboxylic acid cyclopropylamide;
1'-(2,4-dichlorobenzenesulfonyl)-1',2',3',6'-tetrahydro-[2,4']bipyridinyl-6-carboxylic acid cyclopropylamide;
1'-(3-trifluoromethoxybenzenesulfonyl)-1',2',3',6'-tetrahydro-[2,4']bipyridinyl-6-carboxylic acid cyclopropylamide;
1'-(3-cyano-4-fluorobenzenesulfonyl)-1',2',3',6'-tetrahydro-[2,4']bipyridinyl-6-carboxylic acid cyclopropylamide;
1'-(pyridin-2-ylsulfonyl)-1',2',3',6'-tetrahydro-[2,4']bipyridinyl-6-carboxylic acid cyclopropylamide;
1'-(pyridin-3-ylsulfonyl)-1',2',3',6'-tetrahydro-[2,4']bipyridinyl-6-carboxylic acid cyclopropylamide;
1'-(3-trifluoromethylbenzylsulfonyl)-1',2',3',6'-tetrahydro-[2,4']bipyridinyl-6-carboxylic acid cyclopropylamide;
1'-(3,5-dichlorobenzenesulfonyl)-1',2',3',6'-tetrahydro-[2,4']bipyridinyl-6-carboxylic acid cyclopropylamide;
1'-(2,4,6-trifluorobenzenesulfonyl)-1',2',3',6'-tetrahydro-[2,4']bipyridinyl-6-carboxylic acid cyclopropylamide;
1'-(2-methylprop-1-ylsulfonyl)-1',2',3',6'-tetrahydro-[2,4']bipyridinyl-6-carboxylic acid cyclopropylamide;
1'-cyclopentylsulfonyl-1',2',3',6'-tetrahydro-[2,4']bipyridinyl-6-carboxylic acid cyclopropylamide;
1'-(thiophen-3-ylsulfonyl)-1',2',3',6'-tetrahydro-[2,4']bipyridinyl-6-carboxylic acid cyclopropylamide;
1'-(4-trifluoromethoxybenzyl)-1',2',3',6'-tetrahydro-[2,4']bipyridinyl-6-carboxylic acid cyclopropylamide;
2-[1-(4-trifluoromethoxybenzenesulfonyl)-1,2,3,6-tetrahydropyridin-4-yl]-pyrimidine-4-carboxylic acid amide;
2-[1-(3-trifluoromethylbenzenesulfonyl)-1,2,3,6-tetrahydropyridin-4-yl]-pyrimidine-4-carboxylic acid amide;
1'-(3-trifluoromethylbenzenesulfonyl)-1',2',3',6'-tetrahydro-[3,4']bipyridinyl-2-carboxylic acid methyl ester;
1'-(3-trifluoromethylbenzenesulfonyl)-1',2',3',6'-tetrahydro-[3,4']bipyridinyl-2-carboxylic acid cyclopropylmethylamide;
1'-(3-trifluoromethylbenzenesulfonyl)-1',2',3',6'-tetrahydro-[3,4']bipyridinyl-2-carboxylic acid 2,2,2-trifluoroethylamide;
1'-(3-trifluoromethylbenzenesulfonyl)-1',2',3',6'-tetrahydro-[3,4']bipyridinyl-2-carboxylic acid 3,3,3-trifluoropropylamide;
1'-(4-trifluoromethoxybenzenesulfonyl)-1',2',3',6'-tetrahydro-[3,4']bipyridinyl-2-carboxylic acid 2,2,2-trifluoroethylamide;

1'-(4-trifluoromethoxybenzenesulfonyl)-1',2',3',6'-tetrahydro-[3,4']bipyridinyl-2-carboxylic acid 3,3,3-trifluoropropylamide;
1'-(4-trifluoromethoxybenzenesulfonyl)-1',2',3',6'-tetrahydro-[3,4']bipyridinyl-2-carboxylic acid cyclopropylmethylamide;
1'-(3-trifluoromethylbenzenesulfonyl)-1',2',3',6'-tetrahydro-[2,4']bipyridinyl-6-carboxylic acid cyclopropylmethylamide;
1'-(3-trifluoromethylbenzenesulfonyl)-1',2',3',6'-tetrahydro-[2,4']-bipyridinyl-6-carboxylic acid 2,2,2-trifluoroethylamide;
1'-(3-trifluoromethylbenzenesulfonyl)-1',2',3',6'-tetrahydro-[2,4']-bipyridinyl-6-carboxylic acid 3,3,3-trifluoropropylamide;
1'-(4-trifluoromethoxybenzenesulfonyl)-1',2',3',6'-tetrahydro-[2,4']-bipyridinyl-6-carboxylic acid 2,2,2-trifluoroethylamide;
1'-(4-trifluoromethoxybenzenesulfonyl)-1',2',3',6'-tetrahydro-[2,4']bipyridinyl-6-carboxylic acid 3,3,3-trifluoropropylamide;
1'-(4-trifluoromethoxybenzenesulfonyl)-1',2',3',6'-tetrahydro-[2,4']bipyridinyl-6-carboxylic acid 4-fluorophenylamide;
1'-(3-trifluoromethylbenzenesulfonyl)-1',2',3',6'-tetrahydro-[2,4']bipyridinyl-6-carboxylic acid amide;
1'-(3-trifluoromethylbenzenesulfonyl)-1',2',3',6'-tetrahydro-[2,4']bipyridinyl-6-carboxylic acid 2-hydroxyethylamide;
1'-(3-trifluoromethylbenzenesulfonyl)-1',2',3',6'-tetrahydro-[2,4']bipyridinyl-6-carboxylic acid 1,3-dihydroxyprop-2-ylamide;
1'-(3-trifluoromethylbenzenesulfonyl)-1',2',3',6'-tetrahydro-[2,4']bipyridinyl-6-carbonitrile;
N-cyclopropylmethyl-1'-(4-trifluoromethoxybenzenesulfonyl)-1',2',3',6'-tetrahydro-[2,4']bipyridinyl-6-carboxamidine;
2-[1-(3-trifluoromethylbenzenesulfonyl)-1,2,3,6-tetrahydropyridin-4-yl]pyrimidine-4-carboxylic acid cyclopropylamide;
2-[1-(3-trifluoromethylbenzenesulfonyl)-1,2,3,6-tetrahydropyridin-4-yl]pyrimidine-4-carboxylic acid cyclopropylmethylamide;
2-[1-(4-trifluoromethoxybenzenesulfonyl)-1,2,3,6-tetrahydropyridin-4-yl]pyrimidine-4-carboxylic acid cyclopropylamide;
5-chloro-1'-(3-trifluoromethylbenzenesulfonyl)-1',2',3',6'-tetrahydro-[2,4']bipyridinyl-6-carboxylic acid cyclopropylamide;
5-chloro-1'-(4-trifluoromethoxybenzenesulfonyl)-1',2',3',6'-tetrahydro-[2,4']bipyridinyl-6-carboxylic acid cyclopropylamide;
6'-oxo-1'-(3-trifluoromethylbenzenesulfonyl)-1',2',3',6'-tetrahydro-[2,4']bipyridinyl-6-carboxylic acid cyclopropylamide;
6-[8-(3-trifluoromethylbenzenesulfonyl)-8-aza-bicyclo[3.2.1]oct-2-en-3-yl]pyridine-2-carboxylic acid cyclopropylamide;
2-[1-(4-trifluoromethoxybenzenesulfonyl)-1,2,3,6-tetrahydropyridin-4-yl]oxazole-4-carboxylic acid cyclopropylamide;
1'-[2,2,2-trifluoro-1-(4-trifluoromethoxyphenyl)-ethyl]-1',2',3',6'-tetrahydro-[2,4']bipyridinyl-6-carboxylic acid cyclopropylamide;
1'-[2,2,2-trifluoro-1-(4-hydroxymethylphenyl)-ethyl]-1',2',3',6'-tetrahydro-[2,4']bipyridinyl-6-carboxylic acid cyclopropylamide;
N-cyclopropyl-6-{1-[(3-trifluoromethylisoxazol-5-yl)methyl]-1,2,3,6-tetrahydropyridin-4-yl}picolinamide;
1'-(3-trifluoromethylbenzenesulfonyl)-1',2',3',6'-tetrahydro-[2,4']bipyridinyl-6-carboxylic acid methyl ester;
1'-(3-trifluoromethylbenzenesulfonyl)-1',2',3',6'-tetrahydro-[2,4']bipyridinyl-6-carboxylic acid;
1'-(3-trifluoromethylbenzenesulfonyl)-1',2',3',6'-tetrahydro-[2,4']bipyridinyl-6-yl]methanol;
1'-(3-trifluoromethylbenzenesulfonyl)-1',2',3',6'-tetrahydro [2,4']bipyridinyl-6-cyclopropanoylamine;
1'-[(3-trifluoromethylbenzene)aminosulfonyl]-1',2',3',6'-tetrahydro-[2,4']bipyridinyl-6-carboxylic acid cyclopropylamide;

and the pharmaceutically acceptable salts, prodrugs and solvates thereof.

Useful cycloalkyl groups are selected from $C_{3-12}$ cycloalkyl. Typical cycloalkyl groups include cyclopropyl, cyclobutyl, cyclopentyl, cyclohexyl, cycloheptyl, and cyclooctyl.

Useful cycloalkenyl groups are selected from $C_{3-12}$ cycloalkenyl. Typical cycloalkenyl groups include cyclopropenyl, cyclobutenyl, cyclopentenyl, cyclohexenyl, cycloheptenyl, and cyclooctenyl.

Useful halo or halogen groups include fluorine, chlorine, bromine and iodine.

Useful alkyl groups are selected from straight-chained and branched $C_{1-10}$ alkyl groups, more preferably straight chain $C_{1-6}$ alkyl groups and branched chain $C_{3-6}$ alkyl groups, and more preferably straight chain $C_{1-4}$ alkyl groups and branched chain $C_{3-4}$ alkyl groups. Typical $C_{1-10}$ alkyl groups include methyl, ethyl, propyl, isopropyl, butyl, sec-butyl, tert-butyl, iso-butyl, 3-pentyl, hexyl, heptyl, octyl, nonyl and decyl, among others.

Useful alkenyl groups are selected from $C_{2-6}$ alkenyl groups, preferably $C_{2-4}$ alkenyl. Typical $C_{2-6}$ alkenyl groups include ethenyl, propenyl, isopropenyl, butenyl, sec-butenyl, pentenyl, and hexenyl. Typical $C_{2-4}$ alkenyl groups include ethenyl, propenyl, isopropenyl, butenyl, and sec-butenyl.

Useful alkynyl groups are selected from $C_{2-6}$ alkynyl groups, preferably $C_{2-4}$ alkynyl. Typical $C_{2-6}$ alkynyl groups include ethynyl, propynyl, butynyl, 2-butynyl, pentynyl, and hexynyl groups. Typical $C_{2-4}$ alkynyl groups include ethynyl, propynyl, butynyl, and 2-butynyl groups.

Useful arylalkyl groups include any of the above-mentioned $C_{1-10}$ alkyl groups substituted by any of the $C_{6-14}$ aryl groups mentioned below. Typical arylalkyl groups include benzyl, phenethyl, and naphthylmethyl.

Useful arylalkenyl groups include any of the above-mentioned $C_{2-6}$ alkenyl groups substituted by any of the $C_{6-14}$ aryl groups mentioned below.

Useful arylalkynyl groups include any of the above-mentioned $C_{2-6}$ alkynyl groups substituted by any of the $C_{6-14}$ aryl groups mentioned below.

Useful (cycloalkyl)alkyl groups include any of the above-mentioned $C_{1-10}$ alkyl groups substituted by any of the above-mentioned cycloalkyl groups.

Useful haloalkyl groups include any of the above-mentioned $C_{1-10}$ alkyl groups substituted by one or more fluorine, chlorine, bromine or iodine atoms (e.g., fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups).

Useful hydroxyalkyl groups include any of the above-mentioned $C_{1-10}$ alkyl groups substituted by one or more hydroxy groups, such as monohydroxyalkyl and dihydroxyalkyl groups (e.g., hydroxymethyl, hydroxyethyl, hydroxypropyl and hydroxybutyl groups, and especially hydroxymethyl, 1-hydroxyethyl, 2-hydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl).

Useful alkoxy groups include oxygen substituted by one of the $C_{1-10}$ alkyl groups mentioned above (e.g., methoxy, ethoxy, propoxy, iso-propoxy, butoxy, tert-butoxy, iso-butoxy, sec-butoxy, and pentyloxy).

Useful alkoxyalkyl groups include any of the above-mentioned $C_{1-10}$ alkyl groups substituted with any of the above-mentioned alkoxy groups (e.g., methoxymethyl, methoxyethyl, methoxypropyl, methoxybutyl, ethoxymethyl, ethoxyethyl, ethoxypropyl, ethoxybutyl, propoxymethyl, isopropoxymethyl, propoxyethyl, propoxypropyl, butoxymethyl, tert-butoxymethyl, isobutoxymethyl, sec-butoxymethyl, and pentyloxymethyl).

Useful haloalkoxy groups include oxygen substituted by one of the $C_{1-10}$ haloalkyl groups mentioned above (e.g., fluoromethoxy, difluoromethoxy, trifluoromethoxy, and 2,2,2-trifluoroethoxy).

Useful aryl groups are $C_{6-14}$ aryl, especially $C_{6-10}$ aryl. Typical $C_{6-14}$ aryl groups include phenyl, naphthyl, phenanthryl, anthracyl, indenyl, azulenyl, biphenyl, biphenylenyl, and fluorenyl groups, more preferably phenyl, naphthyl, and biphenyl groups.

The term "heteroaryl" or "heteroaromatic" as employed herein refers to groups having 5 to 14 ring atoms, with 6, 10 or 14 π electrons shared in a cyclic array, and containing carbon atoms and 1, 2, or 3 oxygen, nitrogen or sulfur heteroatoms, or 4 nitrogen atoms. Examples of heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. Preferred heteroaryl groups include thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, pyrimidin-5-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl).

As used herein, the term "6-membered heteroaromatic ring" includes any of the above-mentioned heteroaromatic groups that have 6 ring atoms.

As used herein, the term "5-membered heteroaromatic ring" includes any of the above-mentioned heteroaromatic groups that have 5 ring atoms.

As used herein, the term "5-membered, N-containing heteroaryl" includes any of the above-mentioned heteroaryl groups that have 5 ring atoms and at least one nitrogen atom as a ring atom.

Useful heteroarylalkyl groups include any of the above-mentioned $C_{1-10}$ alkyl groups substituted by any of the heteroaryl groups mentioned above. Useful values include, for example, pyridin-2-ylmethyl, pyridin-3-ylmethyl, and pyridin-4-ylmethyl.

The terms "heterocyclic" and "heterocyclo" are used herein to mean saturated or wholly or partially unsaturated 3-7 membered monocyclic, or 7-10 membered bicyclic ring system, which consist of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on a carbon atom or on a nitrogen atom if the resulting compound is stable. Examples include, but are not limited to, pyrrolidinyl, piperidinyl, piperazinyl, morpholinyl, imidazolinyl, pyrazolidinyl, tetrahydrofuranyl, oxazolidinyl, tetrahydrothienyl, imidazolidinyl, hexahydropyrimidinyl, benzodiazepines, and the like.

As used herein, the term "5-membered heterocyclic ring" includes any of the above-mentioned heterocyclic groups that are 5-membered, i.e., that have 5 ring atoms.

As used herein, the term "5-membered, partially unsaturated, N-containing heterocyclo" includes any of the above-mentioned heterocyclo groups that are 5-membered, partially unsaturated and contain at least one nitrogen atom as a ring member.

Useful heterocycloalkyl groups include any of the above-mentioned $C_{1-10}$ alkyl groups substituted by any of the above-mentioned heterocyclic groups.

As used herein, the term "amino" or "amino group" refers to —$NH_2$.

Useful aminoalkyl groups include any of the above-mentioned $C_{1-10}$ alkyl groups substituted with an amino group.

Useful diaminoalkyl groups include any of the above-mentioned $C_{1-10}$ alkyl groups substituted with two amino groups.

Useful alkylamino and dialkylamino groups are —$NHR^{15}$ and —$NR^{15}R^{16}$, respectively, wherein $R^{15}$ and $R^{16}$ are each independently selected from a $C_{1-10}$ alkyl group.

Useful hydroxyalkylamino groups are —$NHR^{15}$, wherein $R^{15}$ is any of the above-mentioned hydroxyalkyl groups.

Useful arylamino groups are —$NHR^{15}$, wherein $R^{15}$ is any of the above-mentioned aryl groups, such as phenylamino.

Useful aryl(alkyl)amino groups are —$NR^{15}R^{16}$, wherein $R^{15}$ is any of the above-mentioned aryl groups and $R^{16}$ is any of the above-mentioned $C_{1-10}$ alkyl groups (e.g., phenyl(methyl)amino, phenyl(ethyl)amino, phenyl(propyl)amino, and phenyl(iso-propyl)amino groups.)

Useful alkylaminoalkyl and dialkylaminoalkyl groups are any of the above-mentioned $C_{1-10}$ alkyl groups substituted by any of the above-mentioned alkylamino and dialkylamino groups, respectively.

As used herein, the term "aminocarbonyl" refers to —C(=O)$NH_2$.

Useful alkylcarbonyl groups include a carbonyl group, i.e., —C(=O)—, substituted by any of the above-mentioned $C_{1-10}$ alkyl groups.

Useful alkylcarbonylamino groups include any of the above-mentioned alkylcarbonyl groups attached to an amino nitrogen, such as methylcarbonylamino.

Useful mercaptoalkyl groups include any of the above-mentioned $C_{1-10}$ alkyl groups substituted by a —SH group.

As used herein, the term "carboxy" refers to —COOH.

Useful carboxyalkyl groups include any of the above-mentioned $C_{1-10}$ alkyl groups substituted by —COOH.

As used herein, the term "ureido" refers to —NH—C(=O)—$NH_2$.

As used herein, the term "azido" refers to —$N_3$.

As used herein, the term "optionally substituted" refers to a group that may be unsubstituted or substituted.

Optional substituents on optionally substituted groups, when not otherwise indicated, include one or more groups, preferably 1, 2, or 3 groups, independently selected from the group consisting of halo, halo($C_{1-6}$)alkyl, aryl, heterocycle, cycloalkyl, $C_{1-6}$ alkyl, $C_{2-6}$ alkenyl, $C_{2-6}$ alkynyl, aryl($C_{1-6}$) alkyl, aryl($C_{2-6}$)alkenyl, aryl($C_{2-6}$)alkynyl, cycloalkyl($C_{1-6}$) alkyl, heterocyclo($C_{1-6}$)alkyl, hydroxy($C_{1-6}$)alkyl, amino ($C_{1-6}$)alkyl, carboxy($C_{1-6}$)alkyl, alkoxy($C_{1-6}$)alkyl, nitro, amino, ureido, cyano, alkylcarbonylamino, hydroxy, thiol, alkylcarbonyloxy, azido, alkoxy, carboxy, aminocarbonyl, and mercapto($C_{1-6}$)alkyl groups mentioned above. Preferred optional substituents include halo, halo($C_{1-6}$)alkyl, hydroxy ($C_{1-6}$)alkyl, amino($C_{1-6}$)alkyl, hydroxy, nitro, $C_{1-6}$ alkyl, alkoxy, and amino.

The invention disclosed herein is also meant to encompass prodrugs of any of the disclosed compounds. As used herein, prodrugs are considered to be any covalently bonded carriers that release the active parent drug in vivo. In general, such prodrugs will be a functional derivative of a compound of Formula I-XII which is readily convertible in vivo, e.g., by being metabolized, into the required compound of Formula I-XII. Conventional procedures for the selection and preparation of suitable prodrug derivatives are described in, for example, *Design of Prodrugs*, H. Bundgaard ed., Elsevier (1985); "Drug and Enzyme Targeting, Part A," K. Widder et al. eds., Vol. 112 in *Methods in Enzymology*, Academic Press (1985); Bundgaard, "Design and Application of Prodrugs," Chapter 5 (pp. 113-191) in *A Textbook of Drug Design and Development*, P. Krogsgaard-Larsen and H. Bundgaard eds., Harwood Academic Publishers (1991); Bundgaard et al., *Adv. Drug Delivery Revs.* 8:1-38 (1992); Bundgaard et al., *J. Pharmaceut. Sci.* 77:285 (1988); and Kakeya et al., *Chem. Pharm. Bull.* 32:692 (1984). Non-limiting examples of prodrugs include esters or amides of compounds of any of Formulae I-XII having hydroxyalkyl or aminoalkyl as a substituent, and these may be prepared by reacting such parent compounds with anhydrides such as succinic anhydride.

The invention disclosed herein is also intended to encompass any of the disclosed compounds being isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, and a $^{36}Cl$, respectively, and preferably $^3H$, $^{11}C$, and $^{14}C$. Isotopically-labeled compounds of the present invention can be prepared by methods known in the art.

The present invention is also directed specifically to $^3H$, $^{11}C$, or $^{14}C$ radiolabeled compounds of any of Formulae I-XII, as well as their pharmaceutically acceptable salts, prodrugs and solvates, and the use of any such compounds as radioligands for their binding site on the calcium channel. For example, one use of the labeled compounds of the present invention is the characterization of specific receptor binding. Another use of a labeled compound of the present invention is an alternative to animal testing for the evaluation of structure-activity relationships. For example, the receptor assay may be performed at a fixed concentration of a labeled compound of the invention and at increasing concentrations of a test compound in a competition assay. For example, a tritiated compound of any of Formulae I-XII can be prepared by introducing tritium into the particular compound, for example, by catalytic dehalogenation with tritium. This method may include reacting a suitably halogen-substituted precursor of the compound with tritium gas in the presence of a suitable catalyst, for example, Pd/C, in the presence or absence of a base. Other suitable methods for preparing tritiated compounds can be found in Filer, *Isotopes in the Physical and Biomedical Sciences, Vol. 1, Labeled Compounds (Part A)*, Chapter 6 (1987). $^{14}C$-labeled compounds can be prepared by employing starting materials having a $^{14}C$ carbon.

Some of the compounds disclosed herein may contain one or more asymmetric centers and may thus give rise to enantiomers, diastereomers, and other stereoisomeric forms. The present invention is meant to encompass the uses of all such possible forms, as well as their racemic and resolved forms and mixtures thereof. The individual enantiomers may be separated according to methods known to those of ordinary skill in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

The term "treating" or "treatment" is meant to encompass administering to a subject a compound of the present invention for the purposes of amelioration or cure, including pre-emptive and palliative treatment.

The invention disclosed herein also encompasses the use of salts of the disclosed compounds, including all non-toxic pharmaceutically acceptable salts thereof of the disclosed compounds. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like.

Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present invention with a solution of a pharmaceutically acceptable non-toxic base such as sodium hydroxide, potassium hydroxide, choline hydroxide, sodium carbonate and the like.

The invention disclosed herein is also meant to encompass solvates of any of the disclosed compounds. Solvates typically do not significantly alter the physiological activity or toxicity of the compounds, and as such may function as pharmacological equivalents. The term "solvate" as used herein is a combination, physical association and/or solvation of a compound of the present invention with a solvent molecule such as, e.g. a disolvate, monosolvate or hemisolvate, where the ratio of solvent molecule to compound of the present invention is 2:1, 1:1 or 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of any of Formulae I-XII may be present as solvated forms with a pharmaceutically acceptable solvent, such as water, methanol, ethanol, and the like, and it is intended that the invention includes both solvated and unsolvated forms of compounds of any of Formulae I-XII. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al., *J. Pharmaceut. Sci.,* 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.,* 5(1): Article 12 (2004), and A. L. Bingham et al., *Chem. Commun.:* 603-604 (2001). A typical, non-limiting, process of preparing a solvate would involve dissolving a compound of any of Formulae I-XII in a desired solvent (organic, water, or a mixture thereof) at temperatures above about 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

Since compounds of Formulae I-XII are blockers of calcium ($Ca^{2+}$) channels, a number of diseases and conditions mediated by calcium ion influx can be treated by employing these compounds (See, e.g., Gould et al., *Proc. Natl. Acad. Sci. USA* 80:5122-5125 (1983); Schwartz et al., *Am. J. Cardiol.* 62:3 G-6G (1988); Ito, M., *Ann. Rev. Neurosci.* 12:85-102 (1989); Nuglisch et al., *J. Cereb. Blood Flow Metab.* 10:654-659 (1990); Janis, R. J. & Triggle, D. J., *Drugs Acting on Calcium Channels, in Calcium Channels: Their Properties, Functions, Regulation and Clinical Relevance, p.* 195-249, Hurwitz et al. eds., CRC Press, London (1991); Hu et al., *Bioorg. Med. Chem. Lett.* 9:2151-2156 (1999); Hu et al., *J. Med. Chem.* 42:4239-4249 (1999); Hu et al., *Bioorg. Med. Chem.* 8:1203-1212 (2000); Song et al., *J. Med. Chem.* 43:3474-3477 (2000); Vanegas et al., *Pain* 85:9-18 (2000); Wallace, M. S., *The Clinical Journal of Pain* 16:S80-S85 (2000); and Lukyanetz et al., *Epilepsia* 43:9-18 (2002)). The present invention is thus directed generally to a method for treating a disorder responsive to the blockade of calcium channels, and particularly the selective blockade of N-type calcium channels, in an animal suffering from, or at risk of suffering from, said disorder, said method comprising administering to the animal an effective amount of a compound represented by any of defined Formulae I-XII, or a pharmaceutically acceptable salt, prodrug or solvate thereof.

The present invention is further directed to a method of modulating calcium channels, especially N-type calcium channels, in an animal in need thereof, said method comprising administering to the animal at least one compound represented by any of defined Formulae I-XII, or a pharmaceutically acceptable salt, prodrug or solvate thereof.

More specifically, the present invention provides a method of treating stroke, the neuronal damage resulting from head trauma, epilepsy, pain (e.g., acute pain, chronic pain, which includes but is not limited to neuropathic pain and inflammatory pain, or surgical pain), migraine, a mood disorder, schizophrenia, a neurodegenerative disorder (e.g., Alzheimer's disease, amyotrophic lateral sclerosis (ALS), or Parkinson's disease), depression, anxiety, a psychosis, hypertension, or cardiac arrhythmia. In one embodiment, the invention provides a method of treating pain. In another embodiment, the type of pain treated is chronic pain. In another embodiment, the type of pain treated is neuropathic pain. In another embodiment, the type of pain treated is inflammatory pain. In another embodiment, the type of pain treated is surgical pain. In another embodiment, the type of pain treated is acute pain. In another embodiment, the treatment of pain (e.g., chronic pain, such as neuropathic pain or inflammatory pain, acute pain or surgical pain) is preemptive. In another embodiment, the treatment of pain is palliative. In each instance, such method of treatment requires administering to an animal in need of such treatment an amount of a compound of the present invention that is therapeutically effective in achieving said treatment. In one embodiment, the amount of such compound is the amount that is effective as to block calcium channels in vivo.

Chronic pain includes, but is not limited to, inflammatory pain, neuropathic pain, postoperative pain, cancer pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes.

Chronic somatic pain generally results from inflammatory responses to tissue injury such as nerve entrapment, surgical procedures, cancer or arthritis (Brower, *Nature Biotechnology* 2000; 18: 387-391).

The inflammatory process is a complex series of biochemical and cellular events activated in response to tissue injury or the presence of foreign substances (Levine, *Inflammatory Pain, In: Textbook of Pain,* Wall and Melzack eds., 3$^{rd}$ ed., 1994). Inflammation often occurs at the site of injured tissue, or foreign material, and contributes to the process of tissue repair and healing. The cardinal signs of inflammation include erythema (redness), heat, edema (swelling), pain and loss of function (ibid.). The majority of patients with inflammatory pain do not experience pain continually, but rather experience enhanced pain when the inflamed site is moved or touched. Inflammatory pain includes, but is not limited to, that associated with osteoarthritis and rheumatoid arthritis.

Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. Chronic pain is different from acute pain in that patients suffer the abnormal pain sensations that can be described as spontaneous pain, continuous superficial burning and/or deep aching pain. The pain can be evoked by heat-, cold-, and mechano-hyperalgesia or by heat-, cold-, or mechano-allodynia.

Neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can also cause nerve injury. Neuropathic pain includes but is not limited to pain caused by nerve injury such as, for example, the pain from which diabetics suffer.

The present invention is also directed to the use of a compound represented by any of defined Formulae I-XII, or a pharmaceutically acceptable salt, prodrug or solvate thereof, in the manufacture of a medicament for treating a disorder responsive to the blockade of calcium channels (e.g., any of the disorders listed above) in an animal suffering from said disorder. In one embodiment, the disorder is responsive to the selective blockade of N-type calcium channels.

Furthermore, the present invention is directed to a method of modulating calcium channels, especially N-type calcium channels, in an animal in need thereof, said method comprising administering to the animal at least one compound represented by any defined Formulae I-XII, or a pharmaceutically acceptable salt, prodrug or solvate thereof.

The present invention is also directed to the use of a compound represented by any of defined Formulae I-XII, or a pharmaceutically acceptable salt, prodrug or solvate thereof, in the manufacture of a medicament, in particular a medicament for modulating calcium channels, especially N-type calcium channels, in an animal in need thereof.

Synthesis of Compounds

The compounds of the present invention can be prepared using methods known to those skilled in the art in view of this disclosure. For example, compounds of Formula I where n, X, Z, $R^1$, $R^2$, $R^8$, $R^9$, and m are as described above, can be prepared as shown in Scheme 1. Additional methods of synthesis are described and illustrated in the working examples set forth below.

Scheme 1

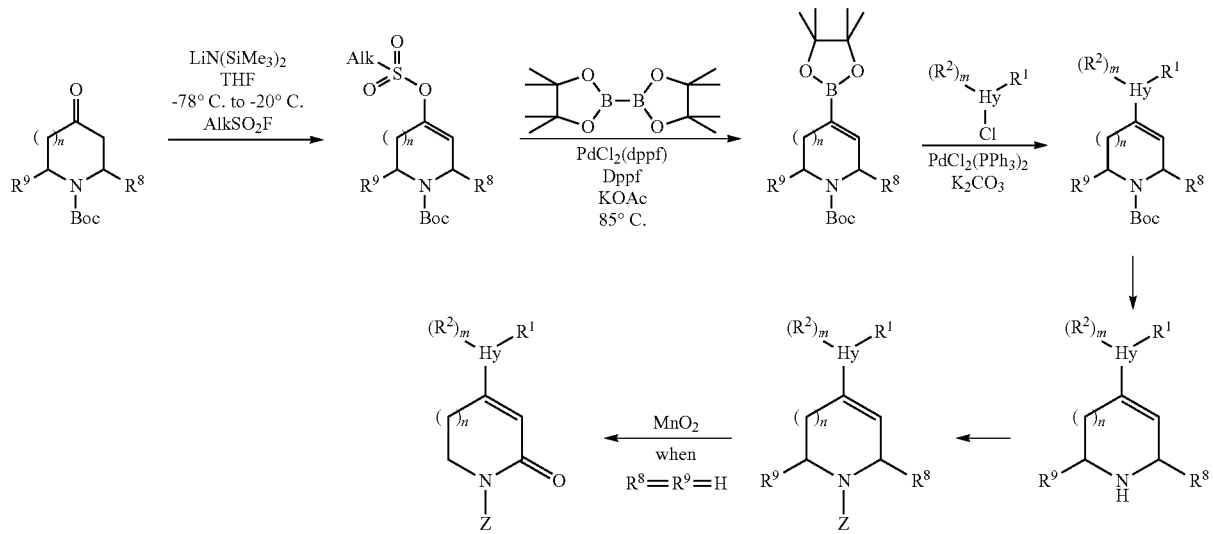

Testing of Compounds

Representative compounds of the present invention were assessed by calcium mobilization and/or electrophysiological assays for calcium channel blocker activity. One aspect of the present invention is based on the use of the compounds herein described as N-type calcium channel blockers. In one aspect of the present invention, it has been found that certain compounds herein described show selectivity as N-type calcium channel blockers. Based upon this property, these compounds are considered useful in treating stroke, neuronal damage resulting from head trauma, migraine, epilepsy, a mood disorder, schizophrenia, a neurodegenerative disorder (such as, e.g., Alzheimer's disease, ALS, or Parkinson's disease), a psychosis, depression, anxiety, hypertension, or cardiac arrhythmia. The compounds of the present invention are also expected to be effective in treating pain, such as acute pain, chronic pain, which includes but is not limited to neuropathic pain and inflammatory pain, or surgical pain.

More specifically, the present invention is directed to compounds of Formulae I-XII that are blockers of calcium channels. According to the present invention, those compounds having preferred N-type calcium channel blocking properties exhibit an $IC_{50}$ of about 100 μM or less in the calcium mobilization and/or electrophysiological assays described herein. Preferably, the compounds of the present invention exhibit an $IC_{50}$ of 10 μM or less. More preferably, the compounds of the present invention exhibit an $IC_{50}$ of about 6 μM or less. Most preferably, the compounds of the present invention exhibit an $IC_{50}$ of about 1.0 μM or less. Compounds of the present invention can be tested for their N-type and L-type $Ca^{2+}$ channel blocking activity by the following calcium mobilization and/or electrophysiological assays.

In one embodiment, compounds useful in the present invention are those represented by any one of Formulae I-XII that exhibit selectivity for N-type calcium channels over L-type calcium channels in the calcium mobilization and/or electrophysiological assays described herein. The phrase "selectivity for N-type calcium channels over L-type calcium channels" is used herein to mean that the ratio of an $IC_{50}$ for L-type channel blocking activity for a compound of the present invention over an $IC_{50}$ for N-type channel blocking activity for the same compound is more than 1, i.e., LTCC $IC_{50}$/NTCC $IC_{50}$>1. Preferably, compounds of the present invention exhibit an LTCC $IC_{50}$/NTCC $IC_{50}$ ratio of about 2 or more, about 10 or more, about 20 or more, about 30 or more, about 50 or more, or about 100 or more.

Calcium Mobilization and Electrophysiological Assay Protocols:

Cell maintenance and differentiation. Unless noted otherwise, cell culture reagents were purchased from Mediatech of Herndon, Md. IMR32 cells (American Type Culture Collection, ATCC, Manassas, Va.) were routinely cultured in growth medium consisting of minimum essential medium containing 10% fetal bovine serum (FBS, Hyclone, Logan, Utah), 100 U/mL penicillin, 100 µg/mL streptomycin, 2 mM L-glutamine, 1 mM sodium pyruvate, and 1×MEM non-essential amino acids. 80-90% confluent flasks of cells were differentiated using the following differentiation medium: Growth medium plus 1 mM dibutyryl cyclic AMP (Sigma, St. Louis, Mo.), and 2.5 µM bromodeoxyuridine (Sigma). Cells were differentiated for 8 days by replacing differentiation medium every 2-3 days.

A7r5 (ATCC) cells were maintained and routinely cultured in A7r5 growth medium consisting of Dulbecco's Modified Eagles Medium containing 10% FBS, 100 U/mL penicillin, 100 µg/mL streptomycin, 4 mM L-glutamine, and 0.15% sodium bicarbonate. 80-90% confluent flasks of cells were differentiated using the following differentiation medium: A7r5 Growth Medium plus 1 mM dibutyryl cyclic AMP (Sigma). Cells were differentiated for 8 days by replacing differentiation medium every 2-3 days.

Recombinant human embryonal kidney cells (HEK293, ATCC) stably transfected with either N-type calcium channel (NTCC) subunits ($\alpha 1b$, $\alpha 2\delta$, and $\beta 3$) or L-type calcium channel (LTCC) subunits ($\alpha 1c$, $\alpha 2\delta$, and $\beta 1$) were routinely cultured in growth medium consisting of Dulbecco's Modified Eagles Medium containing 10% FBS, 100 U/mL penicillin, 100 µg/mL streptomycin, 4 mM L-glutamine, 500 µg/mL geneticin (G418), 20 µg/mL Blasticidin S (InVivogen, San Diego, Calif.) and 500 µg/mL zeocin (InVivogen).

FLIPR Calcium Mobilization Assay for N-type Calcium Channel. One day prior to performing this assay, differentiated IMR32 cells were treated with 1× CellStripper, and seeded on poly-D-lysine-coated 96-well clear-bottom black plates (Becton Dickinson, Franklin Lakes, N.J.) at 200,000 cells/well. On the day of the assay, the cell plates were washed with IMR32 buffer (127 mM NaCl, 1 mM KCl, 2 mM $MgCl_2$, 700 µM $NaH_2PO_4$, 5 mM $CaCl_2$, 5 mM $NaHCO_3$, 8 mM HEPES, 10 mM glucose, pH 7.4), then pre-stimulated with KCl and loaded as follows: 0.05 mL of IMR32 buffer, 0.05 mL of each compound tested diluted in IMR32 buffer containing 20 µM nitrendipine (Sigma), and 0.1 mL KCl dissolved in IMR32 buffer, plus Fluo-4 were added (3 µM final concentration, Molecular Probes, Eugene, Oreg.). Final test compound concentrations ranged from about 846 pM to about 17 µM, final nitrendipine concentration was 5 µM, and final KCl concentration was 90 mM. After 1 hour, the cells were washed twice with 0.05 mL of each compound tested in nitrendipine-containing IMR32 buffer (no KCl or Fluo-4), and then replaced with 0.1 mL of each compound tested in nitrendipine-containing IMR32 buffer. Plates were then transferred to a Fluorimetric Imaging Plate Reader (FLIPR[96], Molecular Devices, Inc., Sunnyvale, Calif.) for assay. The FLIPR measured basal Fluo-4 fluorescence for 315 seconds (i.e., 5 minutes and 15 seconds), then added 0.1 mL KCl agonist dissolved in IMR32 buffer and measured fluorescence for another 45 seconds. Final test compound concentrations on the cells after FLIPR read ranged from about 846 pM to about 17 final nitrendipine concentration was 5 µM, and final KCl concentration was 90 mM. Data were collected over the entire time course and analyzed using Excel, Graph Pad Prism (version 3.02, Graph Pad, San Diego, Calif.), or an in-house non-linear regression analysis software.

FLIPR Calcium Mobilization Assay for L-type Calcium Channel. One day prior to performing this assay, HEK293 cells stably expressing recombinant rat L-type calcium channel (LTCC) subunits ($\alpha 1c$, $\alpha 2\delta$, and $\beta 1$) were trypsinized, then seeded on poly-D-lysine-coated 96-well clear-bottom black plates (Becton Dickinson, Franklin Lakes, N.J.) at 75,000 cells/well. On the day of the assay, the plates were washed with LTCC wash buffer (127 mM NaCl, 2 mM $MgCl_2$, 700 µM $NaH_2PO_4$, 5 mM $CaCl_2$, 5 mM $NaHCO_3$, 8 mM HEPES, 10 mM glucose, pH 7.4), then loaded with 0.1 mL of LTCC wash buffer containing Fluo-4 (3 µM final concentration, Molecular Probes, Eugene, Oreg.). After 1 hour, the cells were washed with 0.1 mL LTCC wash buffer and resuspended in 0.05 mL LTCC assay buffer (same composition as LTCC wash buffer). Plates were then transferred to a FLIPR[96] for assay. The FLIPR measured basal Fluo-4 fluorescence for 15 seconds, then added 0.05 mL of each compound tested diluted in LTCC assay buffer at final concentrations ranging from about 846 pM to about 17 µM. Fluo-4 fluorescence was then measured for 5 minutes. 0.1 mL KCl agonist dissolved in LTCC assay buffer was then added to the cells to produce a final concentration of 90 mM KCl, and fluorescence was measured for another 45 seconds. Data were collected over the entire time course and analyzed using Excel, Graph Pad Prism, or an in-house regression analysis software.

Alternative FLIPR Calcium Mobilization Assay for L-type Calcium Channel. Alternatively, the following cell line and procedure may be used for the FLIPR calcium mobilization assay for L-type calcium channel. One day prior to performing this assay, differentiated A7r5 cells are trypsinized, then seeded on tissue culture treated 96-well clear-bottom black plates (Becton Dickinson, Franklin Lakes, N.J.) at a dilution of 1:1 from a confluent T150 $cm^2$ flask. On the day of the assay, the plates are washed with A7r5 wash buffer (127 mM NaCl, 2 mM $MgCl_2$, 700 µM $NaH_2PO_4$, 5 mM $CaCl_2$, 5 mM $NaHCO_3$, 8 mM HEPES, 10 mM glucose, pH 7.4), then loaded with 0.1 mL of A7r5 wash buffer containing Fluo-4 (3 µM final concentration, Molecular Probes, Eugene, Oreg.). After 1 hour, the cells are washed with 0.1 mL A7r5 wash buffer and resuspended in 0.05 mL A7r5 assay buffer that is composed of A7r5 wash buffer plus 50 µM valinomycin (Sigma). Plates are then transferred to a FLIPR[96] for assay. The FLIPR measures basal Fluo-4 fluorescence for 15 seconds, then adds 0.05 mL of each compound tested diluted in A7r5 assay buffer at final concentrations ranging from about 846 pM to about 17 µM. Fluo-4 fluorescence is then measured for 5 minutes. 0.1 mL KCl agonist dissolved in A7r5 assay buffer is then added to the cells to produce a final concentration of 90 mM KCl, and fluorescence was measured for another 45 seconds. Data were collected over the entire time course and analyzed using Excel, Graph Pad Prism, or an in-house regression analysis software.

Cloning of N- and L-type calcium channel subunit open reading frame cDNAs. Five cDNAs encoding subunits of the rat N- or L-type calcium channels were cloned by PCR amplification in order to reconstitute functional channels in a heterologous system. These were the alpha1b (α1b), beta1 (β1), beta3 (β3), alpha2delta (α2δ), and alpha1c (α1c) subunit cDNAs. The alpha1b subunit cDNA has been described by Dubel et al. in *Proc. Natl. Acad. Sci. U.S.A* 89: 5058-5062 (1992). The beta1 subunit cDNA has been described by Pragnell et al. in *FEBS Lett.* 291: 253-258 (1991). The beta3 subunit cDNA has been described by Castellano et al. in *J. Biol. Chem.* 268: 12359-12366 (1993). The alpha2delta subunit cDNA has been described by Kim et al. in *Proc. Natl. Acad. Sci. U.S.A*. 89: 3251-3255 (1992). The alpha1c subunit cDNA has been described by Koch et al. in *J. Biol. Chem.* 265: 17786-17791 (1990).

The 7.0 kb cDNA containing the entire α1b open reading frame (ORF) was PCR amplified as two overlapping cDNA fragments, i.e., a 2.7 kb 5' fragment and a 4.4 kb 3' fragment. The 5' fragment was amplified from rat brain cDNA using primers 1 (SEQ ID NO:1, TABLE 1) and 2 (SEQ ID NO:2, TABLE 1), and the 3' fragment was amplified from rat spinal cord cDNA using primers 3 (SEQ ID NO:3, TABLE 1) and 4 (SEQ ID NO:4, TABLE 1). The two fragments were joined by ligation at a common restriction site to create the entire 7.0 kb cDNA. This ORF encodes the protein isoform generated by alternative splicing termed "+A ΔSFMG ΔET" according to the nomenclature of Lin et al. (*Neuron* 18: 153-166 (1997)). The entire cDNA was sequenced with redundant coverage on both strands. The cDNA was then inserted into the mammalian expression vector pcDNA6.2DEST (Invitrogen, Carlsbad Calif.) by homologous recombination using the Gateway system (Invitrogen).

The 1.8 kb cDNA encoding the β1 subunit, the 1.45 kb cDNA encoding the beta3 subunit, and the 3.3 kb cDNA encoding the alpha2delta subunit were cloned by PCR amplification from rat spinal cord cDNA (β1) or brain cDNA (β3, α2δ). Primers 5 (SEQ ID NO:5, TABLE 1) and 6 (SEQ ID NO:6, TABLE 1) were used for the β1 cDNA amplification; primers 7 (SEQ ID NO:7, TABLE 1) and 8 (SEQ ID NO:8, TABLE 1) were used for the β3 cDNA amplification; and primers 9 (SEQ ID NO:9, TABLE 1) and 10 (SEQ ID NO:10, TABLE 1) were used for the α2δ cDNA amplification. PCR products were subcloned and fully sequenced on both strands. Clones matching the reference sequence (β1: NM_017346; β3: NM_012828; α2δ: M86621) and the gene's GenBank rat genomic DNA sequences were recombined into the mammalian expression vector pcDNA3.2DEST (β1, β3) or pcDNA3.1-Zeo (α2δ), which had been modified to a vector compatible with the Gateway recombination system using the Gateway vector adaptor kit (Invitrogen). Proper recombination was confirmed by sequencing of recombinogenic regions. For β3 expression vector, proper protein expression was confirmed by Western blot analysis of lysates of transfected HEK293 cells using a rabbit polyclonal antiserum directed against the rat β3 subunit (USA Biological).

The 6.5 kb cDNA encoding the L-type calcium channel α1c subunit was cloned by PCR amplification from rat heart cDNA using primers 11 (SEQ ID NO:11, TABLE 1) and 12 (SEQ ID NO:12, TABLE 1). The PCR fragment was subcloned and fully sequenced on both strands to confirm its identity. A clone matching consensus reference sequence AF394939 and rat genomic DNA sequences was recombined into the mammalian expression vector pcDNA6.2DEST. Sequences around the recombinogenic region were sequenced to confirm accurate recombination into the expression vector.

TABLE 1

| PRIMER SEQUENCE | SEQ ID NO. |
|---|---|
| CACC ATG GTC CGC TTC GGG GAC | 1 |
| CCG TTC AGT GGC CTC CTC C | 2 |
| C TAG CAC CAG TGA TCC TGG TCTG | 3 |
| AGT GCG TTG TGA GCG CAG TA | 4 |
| CAC CAT GGT CCA GAA GAG CGG | 5 |
| TCTCAGCGGATGTAGACGCCT | 6 |
| CAC CAT GTA TGA CGA CTC CTA C | 7 |
| GGT GGT CAG TAG CTG TCC TTA GG | 8 |
| CAC CAT GGC TGC TGG CTG CCT | 9 |
| AGA GGG TCA CCA TAG ATA GTG TCT G | 10 |
| CACCATGATTCGGGCCTTCGCT | 11 |
| AGCCTGCGGACTACAGGTTGCTGAC | 12 |

N-type Recombinant Cell Line Development. N-type calcium channel expressing HEK-293 cells were created in two stages. Stage 1 was created as follows. The rat α1b, and β3 cDNA expression constructs (2.5 µg each) were co-transfected into human embryonic kidney (HEK-293) cells by Lipofectamine Plus reagent (Invitrogen), as per manufacturer's instructions. 24 hours later, cells were split in limiting dilution into multiple 96-well plates in selection media containing 20 µg/mL blasticidin and 500 µg/mL geneticin, and incubated for 3 weeks at 37° C., 5% $CO_2$, 95% humidity. Plates containing ≦1 clone per well were cultured until wells positive for single clones were confluent. Individual clones were then arrayed into columns of a destination 96-well plate, and partly split into 6-well plates for culture maintenance. Array plates were washed once with IMR32 buffer and cells loaded for 1 hour with 0.1 mL of IMR32 buffer containing Fluo-4 (3 µM final concentration, Molecular Probes). Then they were washed twice with 0.1 mL of IMR32 buffer, and replaced with 0.1 mL IMR32 buffer. Plates were then transferred to a FLIPR[96] for assay. The FLIPR measured basal Fluo-4 fluorescence for 315 seconds, then added 0.1 mL KCl agonist dissolved in IMR32 buffer and measured fluorescence for another 45 seconds. Final KCl concentration was 90 mM. Data were collected over the entire time course and analyzed using Excel, Graph Pad Prism, or Activity Base (version 5.1, IDBS, Parsippany, N.J.) software. The clone with the greatest signal-to-noise ratio, best stability of response with passage number, and best adhesion to PDL precoated plates (Becton Dickinson) was expanded, characterized and used for stage 2 cell line development.

Stage 2 of N-type cell line development was carried out as follows. The rat α2δ cDNA expression construct (5 µg each) was transfected into the stage 1 N-type clonal cell line by Lipofectamine Plus reagent (Invitrogen), as per manufacturer's instructions. 24 hours later, cells were split in limiting dilution into multiple 96-well plates in selection media containing 20 µg/mL blasticidin, 500 µg/mL geneticin, and 250 µg/mL zeocin and incubated for 3 weeks at 37° C., 5% $CO_2$, 95% humidity. Plates containing 1 clone per well were cultured and handled according to the same steps and procedures described above for the stage 1 cell line. The three clones with the greatest signal-to-noise, best stability of response with passage number, and best adhesion to PDL precoated plates (Becton Dickinson) were expanded, characterized and tested in electrophysiology for the best current size, N-type pharmacology, N-type characteristic current-voltage relationship and kinetics as described below.

L-type Recombinant Cell Line Development. L-type calcium channel expressing HEK-293 cells were created in two stages. Stage 1 was created as follows. The rat α1c, and β1 cDNA expression constructs (2.5 µg each) were co-transfected into human embryonic kidney (HEK-293) cells by Lipofectamine Plus reagent (Invitrogen), as per manufacturer's instructions. 24 hours later, cells were split in limiting dilution into multiple 96-well plates in selection media containing 20 µg/mL blasticidin and 500 µg/mL geneticin, and incubated for 3 weeks at 37° C., 5% $CO_2$, 95% humidity. Plates containing ≦1 clone per well were cultured until wells positive for single clones were confluent. Individual clones were then arrayed into columns of a destination 96-well plate, and partly split into 6-well plates for culture maintenance. Array plates were washed once with LTCC wash (or assay) buffer and cells loaded for 1 hour with 0.1 mL of LTCC buffer containing Fluo-4 (3 µM final concentration, Molecular Probes). Then they were washed twice with 0.1 mL of LTCC buffer, and replaced with 0.1 mL LTCC buffer. Plates were then transferred to a FLIPR[96] for assay. The FLIPR measured basal Fluo-4 fluorescence for 315 seconds, then added 0.1 mL KCl agonist dissolved in LTCC buffer and measured fluorescence for another 45 seconds. Final KCl concentration was 90 mM. Data were collected over the entire time course and analyzed using Excel, Graph Pad Prism, or Activity Base software. The clone with the greatest signal-to-noise ratio, best stability of response with passage number, and best adhesion to PDL precoated plates (Becton Dickinson) was expanded, characterized and used for stage 2 cell line development.

Stage 2 of L-type cell line development was carried out as follows. The rat α2δ cDNA expression construct (5 µg each) was transfected into the stage 1 L-type clonal cell line by Lipofectamine Plus reagent (Invitrogen), as per manufacturer's instructions. 24 hours later, cells were split in limiting dilution into multiple 96-well plates in selection media containing 20 µg/mL blasticidin, 500 µg/mL geneticin, and 250 µg/mL zeocin and incubated for 3 weeks at 37° C., 5% $CO_2$, 95% humidity. Plates containing 1 clone per well were cultured and handled according to the same steps and procedures described above for the stage 1 cell line. The three clones with the greatest signal-to-noise, best stability of response with passage number, and best adhesion to PDL precoated plates (Becton Dickinson) were expanded and characterized.

N-type Electrophysiology in Recombinant Cells. For electrophysiological recording, the cells expressing α1b, β3 and α2δ subunits were seeded on 35-mm culture Petri dishes at a density of approximately $10^4$ cells/dish and kept in an incubator for up to three days for subsequent recordings. For recordings, the dishes were positioned on the stage of an inverted microscope (Nikon, Eclipse E600, Japan) and superfused with a bath solution comprised of $BaCl_2$ (11 mM), $MgCl_2$ (1.5 mM), HEPES (10 mM), TEA chloride (120 mM), glucose (10 mM) adjusted to pH 7.4 with KOH. Whole-cell voltage-clamp recordings were made using conventional patch-clamp techniques (Hamill et al., *Pfluegers Arch.* 391: 85-100 (1981)) at room temperature (22-24° C.). The patch-clamp pipettes were pulled from WPI, thick-walled borosilicate glass (WPI, Sarasota, Fla.). Currents were recorded using an Axopatch 200A amplifier (Axon Instruments, Union City, Calif.) and were leak-subtracted (P/4), low-pass filtered (1 kHz, 4-pole Bessel), digitized (20-50-µs intervals), and stored using Digidata 1200 B interface and Pclamp8.0/Clampex software (Axon Instruments, Union City, Calif.). The pipettes were back-filled with internal solution containing CsCl (110 mM), $MgCl_2$ (3 mM), EGTA (3 mM), HEPES (40 mM), Mg-ATP (4 mM), $Na_2GTP$ (0.5 mM), and adjusted to pH 7.2 with CsOH. The pipette resistance ranged from 2 to 3 MOhm and was compensated by 75-80% by the built-in electronic circuitry.

Currents were elicited by stepping from a holding potential of −90 mV to 0 mV for 20 ms every 20 sec. At the −90 mV membrane voltage about 50% of channels were in the inactivated state, and thus contact with a blocker would involve interaction with both resting and inactivated channels. Every drug was applied at 3 to 4 concentrations increasing in a cumulative manner. Fractional inhibition levels in steady-state were used to draw the partial inhibition concentration curves to get the $IC_{50}$ (i.e. concentration causing 50% reduction in the size of the response) values at −90 mV.

Stock solutions of each test compound were prepared using DMSO. Serial dilutions to desired concentrations were done with bath solution; concentration of DMSO in final solutions was 0.1%. Drugs were applied by gravity flow using a plane multi-barrel array shooter positioned 0.5 mm apart from the cell.

All curve fittings were carried out using Origin software (version 5.0, Microcal). A Hill equation was fit to the concentration-inhibition curves to determine $IC_{50}$ values.

N-type Electrophysiology in Neuronal Cells. To determine dissociation constants in resting versus inactivated state for N-type calcium channels, neuronal cells that endogenously express N-type calcium channels can be used. For electrophysiological recording, the neuronal cells expressing N-type calcium channels are seeded on 35-mm culture Petri dishes at a density of approximately $10^4$ cells/dish and kept in an incubator for up to three days for subsequent recordings. For recordings, the dishes are positioned on the stage of an inverted microscope (Nikon, Eclipse E600, Japan) and superfused with a bath solution comprised of $BaCl_2$ (11 mM), $MgCl_2$ (1.5 mM), HEPES (10 mM), TEA chloride (120 mM), glucose (10 mM) adjusted to pH 7.4 with KOH. Whole-cell voltage-clamp recordings are made using conventional patch-clamp techniques (Hamill et al., *Pfluegers Arch.* 391: 85-100 (1981)) at room temperature (22-24° C.). The patch-clamp pipettes are pulled from WPI, thick-walled borosilicate glass (WPI, Sarasota, Fla.). Currents are recorded using an Axopatch 200A amplifier (Axon Instruments, Union City, Calif.) and leak-subtracted (P/4), low-pass filtered (1 kHz, 4-pole Bessel), digitized (20-50-µs intervals), and stored using Digidata 1200 B interface and Pclamp8.0/Clampex software (Axon Instruments, Union City, Calif.). The pipettes are back-filled with internal solution containing CsCl (110 mM), $MgCl_2$ (3 mM), EGTA (3 mM), HEPES (40 mM), Mg-ATP (4 mM), $Na_2GTP$ (0.5 mM), and adjusted to pH 7.2 with CsOH. The pipette resistance ranges from 2 to 3 MOhm and is compensated by 75-80% by the built-in electronic circuitry.

Currents are elicited by stepping from a holding potential of −90 mV to 0 mV for 20 ms every 10 sec. At the −90 mV membrane voltage a proportion of channels is in the inactivated state, and thus contact with a blocker would involve interaction with both resting and inactivated channels. This protocol is used as a first tier screen. For dissection of two components of inhibition (resting block with the apparent dissociation constant $K_r$ and inactivated state block with $K_i$), steady-state inactivation curves are collected using a double-pulse protocol. Three-second long depolarizing pre-pulse incrementing in 10 mV steps is followed by a 10 ms test pulse to 0 mV.

Stock solutions of each test compound are prepared using DMSO. Serial dilutions to desired concentrations are done with bath solution; concentration of DMSO in final solutions is 0.1%. Drugs are applied by gravity flow using a plane multi-barrel array shooter positioned ~1 mm apart from the cell.

All curve fittings can be carried out using Origin software (version 5.0, Microcal). A Hill equation is used to fit the concentration-response curves and to determine $IC_{50}$ values. A Boltzman equation is used to fit inactivation curves, returning half-inactivation voltage, $V_{0.5}$, slope p and the amplitude of current at the most negative voltage where eventually all channels are in the resting state. These parameters are used to calculate the apparent dissociation constants: $K_r=((Ab/Ac)/(1-(Ab/Ac))*[b])$ where [b] is the drug concentration, Ac is the maximum test current amplitude in control conditions and Ab is the maximum test current amplitude in the presence of a blocker; $K_i=[b]/((\exp(-(dx/p))*(1+([b]/K_r))-1)$ where dx is the difference between half-inactivation voltage $V_{0.5}$ in the presence and absence of drug and p is the slope.

In Vivo Pharmacology

The compounds of the present invention can be tested for in vivo anticonvulsant activity after i.v., p.o., or i.p. injection using any of a number of anticonvulsant tests in mice, including the maximum electroshock seizure test (MES). Maximum electroshock seizures are induced in male NSA mice weighing between 15-20 g and in male Sprague-Dawley rats weighing between 200-225 g by application of current (for mice: 50 mA, 60 pulses/sec, 0.8 msec pulse width, 1 sec duration, D.C.; for rats: 99 mA, 125 pulses/sec, 0.8 msec pulse width, 2 sec duration, D.C.) using a Ugo Basile ECT device (Model 7801). Mice are restrained by gripping the loose skin on their dorsal surface and saline-coated corneal electrodes are held lightly against the two corneae. Rats are allowed free movement on the bench top and ear-clip electrodes are used. Current is applied and animals are observed for a period of up to 30 seconds for the occurrence of a tonic hindlimb extensor response. A tonic seizure is defined as a hindlimb extension in excess of 90 degrees from the plane of the body. Results can be treated in a quantal manner.

The compounds can be tested for their antinociceptive activity in the formalin model as described in Hunskaar, S., O. B. Fasmer, and K. Hole, *J. Neurosci. Methods* 14: 69-76 (1985). Male Swiss Webster NIH mice (20-30 g; Harlan, San Diego, Calif.) can be used in all experiments. Food is withdrawn on the day of experiment. Mice are placed in Plexiglass jars for at least 1 hour to acclimate to the environment. Following the acclimation period mice are weighed and given either the compound of interest administered i.p. or p.o., or the appropriate volume of vehicle (for example, 10% Tween-80 or 0.9% saline, and other pharmaceutically acceptable vehicles) as control. Fifteen minutes after the i.p. dosing, and 30 minutes after the p.o. dosing mice are injected with formalin (20 μL of 5% formaldehyde solution in saline) into the dorsal surface of the right hind paw. Mice are transferred to the Plexiglass jars and monitored for the amount of time spent licking or biting the injected paw. Periods of licking and biting are recorded in 5-minute intervals for 1 hour after the formalin injection. All experiments are done in a blinded manner during the light cycle. The early phase of the formalin response is measured as licking/biting between 0-5 minutes, and the late phase is measured from 15-50 minutes. Differences between vehicle and drug treated groups can be analyzed by one-way analysis of variance (ANOVA). A P value<0.05 is considered significant. Compounds are considered to be efficacious for treating acute and chronic pain if they have activity in blocking both the early and second phase of formalin-induced paw-licking activity.

Compounds can be tested for their potential to treat chronic pain (i.e., antiallodynic and antihyperalgesic activities) using the Chung model of peripheral neuropathy (Kim and Chung, *Pain* 50: 355-363 (1992)). Male Sprague-Dawley rats weighing between 200-225 g are anesthetized with halothane (1-3% in a mixture of 70% air and 30% oxygen), and their body temperature controlled during anesthesia through use of a homeothermic blanket. A 2-cm dorsal midline incision is then made at the L5 and L6 level, and the para-vertebral muscle groups retracted bilaterally. L5 and L6 spinal nerves are then exposed, isolated, and tightly ligated with 6-0 or 7-0 silk suture. A sham operation is performed exposing the contralateral L5 and L6 spinal nerves, without ligating, as a negative control.

Tactile Allodynia: Sensitivity to non-noxious mechanical stimuli can be measured in animals to assess tactile allodynia. Rats are transferred to an elevated testing cage with a wire mesh floor and allowed to acclimate for five to ten minutes. A series of von Frey monofilaments are applied to the plantar surface of the hindpaw to determine the animal's withdrawal threshold. The first filament used possesses a buckling weight of 9.1 gms (0.96 log value) and is applied up to five times to see if it elicits a withdrawal response. If the animal has a withdrawal response, then the next lightest filament in the series would be applied up to five times to determine if it also could elicit a response. This procedure is repeated with subsequent lesser filaments until there is no response and the identity of the lightest filament that elicits a response is recorded. If the animal does not have a withdrawal response from the initial 9.1 gms filament, then subsequent filaments of increased weight are applied until a filament elicits a response and the identity of this filament is recorded. For each animal, three measurements are made at every time point to produce an average withdrawal threshold determination. Tests can be performed prior to, and at 1, 2, 4 and 24 hours post drug administration.

Mechanical Hyperalgesia: Sensitivity to noxious mechanical stimuli can be measured in animals using the paw pressure test to assess mechanical hyperalgesia. In rats, hind paw withdrawal thresholds ("PWT"), measured in grams, in response to a noxious mechanical stimulus are determined using an analgesymeter (Model 7200, commercially available from Ugo Basile of Italy), as described in Stein (*Biochemistry & Behavior* 31: 451-455 (1988)). The rat's paw is placed on a small platform, and weight is applied in a graded manner up to a maximum of 250 grams. The endpoint is taken as the weight at which the paw is completely withdrawn. PWT is determined once for each rat at each time point. PWT can be measured only in the injured paw, or in both the injured and non-injured paw. In one non-limiting embodiment, mechanical hyperalgesia associated with nerve injury induced pain (neuropathic pain) can be assessed in rats. Rats are tested prior to surgery to determine a baseline, or normal, PWT. Rats are tested again 2 to 3 weeks post-surgery, prior to, and at different times after (e.g. 1, 3, 5 and 24 hr) drug administration. An increase in PWT following drug administration indicates that the test compound reduces mechanical hyperalgesia.

Pharmaceutical Compositions

Although a compound of the present invention may be administered to a mammal in the form of a raw chemical without any other components present, the compound is preferably administered as part of a pharmaceutical composition containing the compound combined with a suitable pharmaceutically acceptable carrier. Such a carrier can be selected from pharmaceutically acceptable excipients and auxiliaries.

Pharmaceutical compositions within the scope of the present invention include all compositions where a compound of the present invention is combined with a pharmaceutically acceptable carrier. In a preferred embodiment, the compound is present in the composition in an amount that is effective to achieve its intended therapeutic purpose. While individual needs may vary, a determination of optimal ranges of effective amounts of each compound is within the skill of the art. Typically, the compounds may be administered to a mammal, e.g., a human, orally at a dose of from about 0.0025 to about 1500 mg per kg body weight of the mammal, or an equivalent amount of a pharmaceutically acceptable salt, prodrug, or solvate thereof, per day to treat, prevent or ameliorate the particular disorder. A useful oral dose of a compound of the present invention administered to a mammal is from about 0.0025 to about 50 mg per kg body weight of the mammal, or an equivalent amount of the pharmaceutically acceptable salt, prodrug, or solvate thereof. For intramuscular injection, the dose is typically about one-half of the oral dose.

A unit oral dose may comprise from about 0.01 to about 50 mg, and preferably about 0.1 to about 10 mg, of the compound. The unit dose can be administered one or more times daily, e.g., as one or more tablets or capsules, each containing from about 0.01 to about 50 mg of the compound, or an equivalent amount of a pharmaceutically acceptable salt, prodrug or solvate thereof.

A pharmaceutical composition of the present invention can be administered to any animal that may experience the beneficial effects of a compound of the present invention. Foremost among such animals are mammals, e.g., humans and companion animals, although the invention is not intended to be so limited.

A pharmaceutical composition of the present invention can be administered by any means that achieves its intended purpose. For example, administration can be by the oral, parenteral, subcutaneous, intravenous, intramuscular, intraperitoneal, transdermal, intranasal, transmucosal, rectal, intravaginal or buccal route, or by inhalation. The dosage administered and route of administration will vary, depending upon the circumstances of the particular subject, and taking into account such factors as age, health, and weight of the recipient, condition or disorder to be treated, kind of concurrent treatment, if any, frequency of treatment, and the nature of the effect desired.

In one embodiment, a pharmaceutical composition of the present invention can be administered orally and is formulated into tablets, dragees, capsules or an oral liquid preparation. In one embodiment, the oral formulation comprises extruded multiparticulates comprising the compound of the invention.

Alternatively, a pharmaceutical composition of the present invention can be administered rectally, and is formulated in suppositories.

Alternatively, a pharmaceutical composition of the present invention can be administered by injection.

Alternatively, a pharmaceutical composition of the present invention can be administered transdermally.

Alternatively, a pharmaceutical composition of the present invention can be administered by inhalation or by intranasal or transmucosal administration.

Alternatively, a pharmaceutical composition of the present invention can be administered by the intravaginal route.

A pharmaceutical composition of the present invention can contain from about 0.01 to 99 percent by weight, and preferably from about 0.25 to 75 percent by weight, of active compound(s).

A method of the present invention, such as a method for treating a disorder responsive to the blockade of calcium channels in an animal in need thereof, can further comprise administering a second therapeutic agent to the animal in combination with a compound of the present invention. In one embodiment, the other therapeutic agent is administered in an effective amount.

Effective amounts of the other therapeutic agents are known to those skilled in the art. However, it is well within the skilled artisan's purview to determine the other therapeutic agent's optimal effective-amount range.

A compound of the present invention (i.e., the first therapeutic agent) and the second therapeutic agent can act additively or, in one embodiment, synergistically. Alternatively, the second therapeutic agent can be used to treat a disorder or condition that is different from the disorder or condition for which the first therapeutic agent is being administered, and which disorder or condition may or may not be a condition or disorder as defined herein. In one embodiment, a compound of the present invention is administered concurrently with a second therapeutic agent; for example, a single composition comprising both an effective amount of a compound of any of Formulae I-XII, and an effective amount of the second therapeutic agent can be administered. Accordingly, the present invention further provides a pharmaceutical composition comprising a combination of a compound of the present invention, the second therapeutic agent, and a pharmaceutically acceptable carrier. Alternatively, a first pharmaceutical composition comprising an effective amount of a compound of any of Formulae I-XII and a second pharmaceutical composition comprising an effective amount of the second therapeutic agent can be concurrently administered. In another embodiment, an effective amount of a compound of the present invention is administered prior or subsequent to administration of an effective amount of the second therapeutic agent. In this embodiment, the compound of the present invention is administered while the second therapeutic agent exerts its therapeutic effect, or the second therapeutic agent is administered while the compound of the present invention exerts its therapeutic effect for treating a disorder or condition.

The second therapeutic agent can be an opioid agonist, a non-opioid analgesic, a non-steroidal anti-inflammatory agent, an antimigraine agent, a Cox-H inhibitor, a β-adrenergic blocker, an anticonvulsant, an antidepressant, an anticancer agent, an agent for treating addictive disorder, an agent for treating Parkinson's disease and parkinsonism, an agent for treating anxiety, an agent for treating epilepsy, an agent for treating a seizure, an agent for treating a stroke, an agent for treating a pruritic condition, an agent for treating psychosis, an agent for treating ALS, an agent for treating a cognitive disorder, an agent for treating a migraine, an agent for treating vomiting, an agent for treating dyskinesia, or an agent for treating depression, or a mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Examples of other suitable non-opioid analgesics include the following, non limiting, chemical classes of analgesic, antipyretic, nonsteroidal antiinflammatory drugs: salicylic acid derivatives, including aspirin, sodium salicylate, choline magnesium trisalicylate, salsalate, diflunisal, salicylsalicylic acid, sulfasalazine, and olsalazin; para aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic Antipyretic and Antiinflammatory Agents and Drugs Employed in the Treatment of Gout*, in Goodman & Gilman's *The Pharmacological Basis of Therapeutics* 617-57 (Perry B. Molinhoff and Raymond W. Ruddon eds., 9th ed 1996) and Glen R. Hanson, *Analgesic, Antipyretic and Anti Inflammatory Drugs* in Remington: *The Science and Practice of Pharmacy* Vol II 1196-1221 (A. R. Gennaro ed. 19th ed. 1995) which are hereby incorporated by reference in their entireties. Suitable Cox-II inhibitors and 5-lipoxygenase inhibitors, as well as combinations thereof, are described in U.S. Pat. No. 6,136,839, which is hereby incorporated by reference in its entirety. Examples of useful Cox II inhibitors include, but are not limited to, rofecoxib and celecoxib.

Examples of useful antimigraine agents include, but are not limited to, alpipride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, and cisplatin.

Therapeutic agents useful for treating an addictive disorder include, but are not limited to, methadone, desipramine, amantadine, fluoxetine, buprenorphine, an opiate agonist, 3-phenoxypyridine, or a serotonin antagonist.

Examples of useful therapeutic agents for treating Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating epilepsy or seizure include, but are not limited to, carbamazepine, ethosuximide, gabapentin, lamotrigine, phenobarbital, phenyloin, primidone, valproic acid, trimethadione, benzodiazepines, gamma-vinyl GABA, acetazolamide, and felbamate.

Examples of useful therapeutic agents for treating stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating a pruritic condition include, but are not limited to, naltrexone; nalmefene; danazol; tricyclics such as amitriptyline, imipramine, and doxepin; antidepressants such as those given below; menthol; camphor; phenol; pramoxine; capsaicin; tar; steroids; and antihistamines.

Examples of useful therapeutic agents for treating psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating ALS include, but are not limited to, baclofen, neurotrophic factors, riluzole, tizanidine, benzodiazepines such as clonazepan and dantrolene.

Examples of useful therapeutic agents for treating cognitive disorders include, but are not limited to, agents for treating or preventing dementia such as tacrine; donepezil; ibuprofen; antipsychotic drugs such as thioridazine and haloperidol; and antidepressant drugs such as those given below.

Examples of useful therapeutic agents for treating a migraine include, but are not limited to, sumatriptan; methysergide; ergotamine; caffeine; and beta-blockers such as propranolol, verapamil, and divalproex.

Examples of useful therapeutic agents for treating vomiting include, but are not limited to, 5-HT3 receptor antagonists such as ondansetron, dolasetron, granisetron, and tropisetron; dopamine receptor antagonists such as prochlorperazine, thiethylperazine, chlorpromazine, metoclopramide, and domperidone; glucocorticoids such as dexamethasone; and benzodiazepines such as lorazepam and alprazolam.

Examples of useful therapeutic agents for treating dyskinesia include, but are not limited to, reserpine and tetrabenazine.

Examples of useful therapeutic agents for treating depression include, but are not limited to, tricyclic antidepressants such as amitryptyline, amoxapine, bupropion, clomipramine, desipramine, doxepin, imipramine, maprotiline, nefazadone, nortriptyline, protriptyline, trazodone, trimipramine, and venlafaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

A pharmaceutical composition of the present invention is preferably manufactured in a manner which itself will be known in view of the instant disclosure, for example, by means of conventional mixing, granulating, dragee-making, dissolving, extrusion, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethylstarch, cross-linked polyvinyl pyrrolidone, agar, or alginic acid or a salt thereof, such as sodium alginate.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate can be used. Dye stuffs or pigments may be added to the tablets or dragee coatings, for example, for identification or in order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which may be mixed with fillers such as lactose, binders such as starches, and/or lubricants such as talc or magnesium stearate and, optionally, stabilizers, or in the form of extruded multiparticulates. In soft capsules, the active compounds are preferably dissolved or suspended in suitable liquids, such as fatty oils or liquid paraffin. In addition, stabilizers may be added.

Possible pharmaceutical preparations for rectal administration include, for example, suppositories, which consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

Suitable formulations for parenteral administration include aqueous solutions of the active compound in a water-soluble form such as, for example, a water-soluble salt, alkaline solution, or acidic solution. Alternatively, a suspension of the active compound may be prepared as an oily suspension. Suitable lipophilic solvents or vehicles for such as suspension may include fatty oils (for example, sesame oil), synthetic fatty acid esters (for example, ethyl oleate), triglycerides, or a polyethylene glycol such as polyethylene glycol-400 (PEG-400). An aqueous suspension may contain one or more substances to increase the viscosity of the suspension, including, for example, sodium carboxymethyl cellulose, sorbitol, and/or dextran. The suspension may optionally contain stabilizers.

The following examples are illustrative, but not limiting, of the compounds, compositions and methods of the present invention. Suitable modifications and adaptations of the variety of conditions and parameters normally encountered in clinical therapy and which are obvious to those skilled in the art in view of this disclosure are within the spirit and scope of the invention.

EXAMPLES

Example 1

N-Cyclopropyl-6-(1,2,3,6-tetrahydropyridin-4-yl) picolinamide hydrochloride (5)

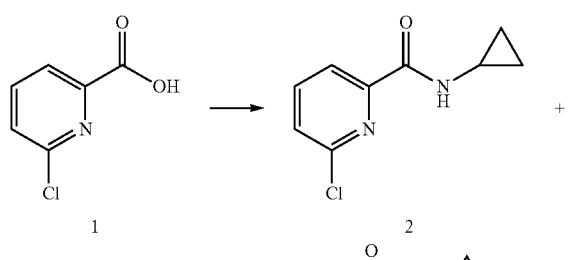

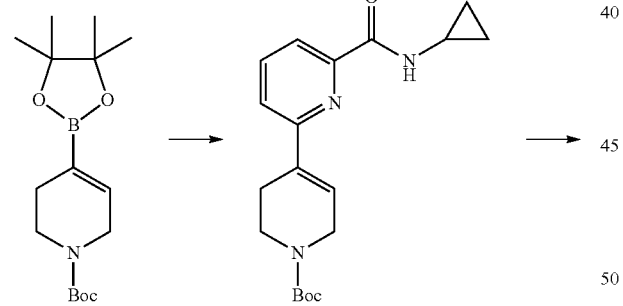

a) To a stirred suspension of compound 1 (500 mg, 3.18 mmol, Aldrich), 1-hydroxybenzotriazole hydrate (HOBt) (430 mg, 3.18 mmol, Aldrich), and N-(3-dimethylaminopropyl)-N' ethylcarbodiimide hydrochloride (EDCI) (672 mg, 3.50 mmol, Aldrich) in dichloromethane was added sequentially diisopropyl ethyl amine (1.1 ml, 6.4 mmol) and cyclopropyl amine (245 μl, 3.5 mmol, Aldrich). The resulting mixture was slowly warmed to room temperature and stirred for 12 hours. The crude mixture was purified on CombiFlash® (Teledyne Isco, Inc., Lincoln, Nebr.) with a gradient of 20% to 80% EtOAc in hexane to provide compound 2 as a white solid (483 mg, yield 77%).

b) The suspension of compound 2 (180 mg, 0.92 mmol), 3,6-dihydro-2H-pyridine-1-tert-butoxycarbonyl-4-boronic acid pinacol ester (3) (284 mg, 0.92 mmol, Carbocore), potassium carbonate (254 mg, 1.84 mmol) and palladium bistriphenylphosphine dichloride (52 mg, 0.07 mmol, Aldrich) in ethyleneglycol dimethylether/ethanol/water in the ratio of 2/1/2 was heated in an oil bath at 95° C. while stirring for 0.5 hour. The crude product was purified without work-up on CombiFlash® with a gradient of 20~40% EtOAc in hexane to provide compound 4 (283 mg, yield 90%).

c) To a solution of compound 4 (283 mg, 0.83 mmol) in 10 ml of EtOAc at 0° C. was added 4N HCl in 1,4-dioxane (5 ml, 20 mmol) while stirring. The resulting mixture was allowed to warm to room temperature and was stirred for 12 hours. The mixture was concentrated to dryness and then suspended in EtOAc. After filtration and washing with hexane, the title compound 5 was obtained as a solid (HCl salt, 173 mg, yield 85%): $^1$H NMR (400 MHz, CD$_3$OD): δ 8.01 (m, 2H), 7.82 (m, 1H), 6.88 (m, 1H), 3.96 (m, 2H), 3.52 (m, 2H), 3.03 (m, 2H), 2.89 (m, 1H), 0.87 (m, 2H), 0.69 (m, 2H).

Example 2

1'-(3-Trifluoromethylbenzenesulfonyl)-1',2',3',6'-tetrahydro-[2,4']bipyridinyl-6-carboxylic acid cyclopropylamide (7)

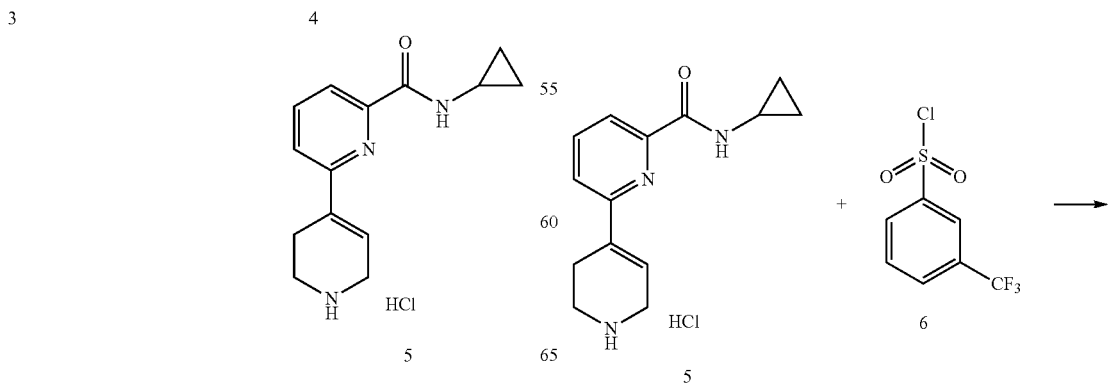

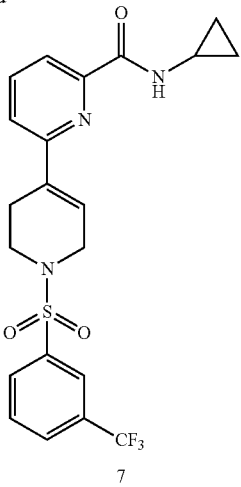

7

Diisopropyl ethyl amine (66 ml, 0.36 mmol) and 3-(trifluoromethyl)benzene sulfonyl chloride (6) (44 mg, 0.18 mmol, Aldrich) were sequentially added to a suspension of compound 5 (50 mg, 0.18 mmol) in dichloromethane at 0° C. while stirring. The reaction was completed within 0.5 hour and the crude product was purified without work-up on CombiFlash® with a gradient of 50-100% EtOAc in hexane to provide the title compound 7 as a white solid (50 mg, yield 64%). $^1$H NMR (400 MHz, CD$_3$OD): δ 8.15 (m, 2H), 8.02-7.83 (m, 4H), 7.67 (dd, 1H, J=1.2, 7.6 Hz), 6.78 (m, 1H), 3.92 (m, 2H), 3.45 (m, 2H), 2.87 (m, 1H), 2.77 (m, 2H), 0.86 (m, 2H), 0.70 (m, 2H); MS: 452 (M+H$^+$), 474 (M+Na).

Similarly, the following compounds were prepared by reacting compound 5 with an appropriate reagent (in parenthesis):

1'-(4-Trifluoromethoxybenzenesulfonyl)-1',2',3',6'-tetrahydro-[2,4']bipyridinyl-6-carboxylic acid cyclopropylamide (4-trifluoromethoxybenzenesulfonyl chloride): $^1$H NMR (400 MHz, CD$_3$OD): δ 8.00 (m, 2H), 7.96 (dd, 1H, J=1.2, 7.2 Hz), 7.91 (t, 1H, J=7.6 Hz), 7.67 (dd, 1H, J=1.2, 7.2 Hz), 7.54 (m, 2H), 6.771 (m, 1H), 3.89 (m, 2H), 3.42 (m, 2H), 2.87 (m, 1H), 2.78 (m, 2H), 0.87 (m, 2H), 0.70 (m, 2H); MS: 468 (M+H$^+$), 490 (M+Na).

1'-(3-Chlorobenzenesulfonyl)-1',2',3',6'-tetrahydro-[2,4']bipyridinyl-6-carboxylic acid cyclopropylamide (3-chlorobenzenesulfonyl chloride): $^1$H NMR (400 MHz, CD$_3$OD): δ 7.74-7.86 (m, 3H), 7.70 (m, 1H), 7.47-7.60 (m, 3H), 6.65 (m, 1H), 3.77 (m, 2H), 3.30 (m, 2H), 2.74 (m, 1H), 2.65 (m, 2H), 0.74 (m, 2H), 0.59 (m, 2H); MS: 418 (M+H$^+$), 440 (M+Na).

1'-(2-Trifluoromethylbenzenesulfonyl)-1',2',3',6'-tetrahydro-[2,4']bipyridinyl-6-carboxylic acid cyclopropylamide (2-trifluoromethylbenzenesulfonyl chloride): $^1$H NMR (400 MHz, CD$_3$OD): δ 8.07 (dd, 1H, J=7.2, 1.6 Hz), 7.89 (dd, 1H, J=1.6, 7.6 Hz), 7.86 (dd, 1H, J=1.2, 7.6 Hz), 7.81 (t, 1H, J=7.6 Hz), 7.74 (m, 2H), 7.60 (dd, 1H, J=1.2, 7.6 Hz), 6.71 (m, 1H), 3.95 (m, 2H), 3.51 (t, 2H, J=5.6 Hz), 2.76 (m, 1H), 2.68 (m, 2H), 0.73 (m, 2H), 0.60 (m, 2H); MS: 452 (M+H$^+$), 475 (M+Na).

1'-(4-Trifluoromethylbenzenesulfonyl)-1',2',3',6'-tetrahydro-[2,4']bipyridinyl-6-carboxylic acid cyclopropylamide (4-trifluoromethylbenzenesulfonyl chloride): $^1$H NMR (400 MHz, CD$_3$OD): δ 7.96 (d, 2H, J=8.4 Hz), 7.84 (d, 2H, J=7.6 Hz), 7.79 (t, 1H, J=7.6 Hz), 7.55 (dd, 1H, J=1.2, 7.6 Hz), 6.65 (m, 1H), 3.80 (m, 2H), 3.32 (t, 2H, J=5.6 Hz), 2.75 (m, 1H), 2.67 (m, 2H), 0.76 (m, 2H), 0.56 (m, 2H); MS: 452 (M+H$^+$), 474 (M+Na).

1'-(4-Fluorobenzenesulfonyl)-1',2',3',6'-tetrahydro-[2,4']bipyridinyl-6-carboxylic acid cyclopropylamide (4-fluorobenzenesulfonyl chloride): $^1$H NMR (400 MHz, CD$_3$OD): δ 7.77-7.86 (m, 4H), 7.56 (dd, 1H, J=8, 1.2 Hz), 7.26 (m, 2H), 6.65 (m, 1H), 3.75 (m, 2H), 3.26 (t, 2H, J=5.6 Hz), 2.75 (m, 1H), 2.67 (m, 2H), 0.75 (m, 2H), 0.60 (m, 2H); MS: 402 (M+H$^+$), 424 (M+Na).

1'-(3-Cyanobenzenesulfonyl)-1',2',3',6'-tetrahydro-[2,4']bipyridinyl-6-carboxylic acid cyclopropylamide (3-cyanobenzenesulfonyl chloride): $^1$H NMR (400 MHz, CD$_3$OD): δ 8.15 (m, 1H), 8.05 (dt, 1H, J=1.6, 7.6 Hz), 7.92 (dt, 1H, J=1.2, 8 Hz), 7.84 (d, 1H, J=7.6 Hz), 7.79 (t, 1H, J=7.6 Hz), 7.70 (t, 1H, J=8 Hz), 7.56 (dd, 1H, J=8, 0.8 Hz), 6.67 (m, 1H), 3.81 (m, 2H), 3.31 (t, 2H, J=5.6 Hz), 2.75 (m, 1H), 2.66 (m, 2H), 0.73 (m, 2H), 0.59 (m, 2H); MS: 409 (M+H$^+$), 431 (M+Na).

1'-Dimethylsulfamoyl-1',2',3',6'-tetrahydro-[2,4']bipyridinyl-6-carboxylic acid cyclopropylamide (N,N'-dimethylaminosulfonyl chloride): $^1$H NMR (400 MHz, CD$_3$OD): δ 7.95 (dd, 1H, J=0.8, 8 Hz), 7.90 (t, 1H, J=7.6 Hz), 7.69 (dd, 1H, J=7.6, 1.2 Hz), 6.81 (m, 1H), 3.99 (m, 2H), 3.52 (t, 2H, J=6 Hz), 2.89 (m, 1H), 2.85 (s, 6H), 2.77 (m, 2H), 0.84 (m, 2H), 0.71 (m, 2H); MS: 351 (M+H$^+$), 373 (M+Na).

1'-(3,3,3-Trifluoropropylsulfonyl)-1',2',3',6'-tetrahydro-[2,4']bipyridinyl-6-carboxylic acid cyclopropylamide (3,3,3-trifluoropropylsulfonyl chloride): $^1$H NMR (400 MHz, CD$_3$OD): δ 7.86 (dd, 1H, J=1.2, 7.6 Hz), 7.81 (t, 1H, J=8 Hz), 7.61 (dd, 1H, J=1.2, 7.6 Hz), 6.74 (m, 1H), 3.99 (m, 2H), 3.50 (t, 2H, J=5.6 Hz), 3.25 (m, 4H), 2.76 (m, 1H), 2.71 (m, 2H), 2.61 (m, 2H), 0.78 (m, 2H), 0.61 (m, 2H); MS: 404 (M+H$^+$), 426 (M+Na).

1'-Cyclohexylsulfonyl-1',2',3',6'-tetrahydro-[2,4']bipyridinyl-6-carboxylic acid cyclopropylamide (cyclohexylsulfonyl chloride): $^1$H NMR (400 MHz, CD$_3$OD): δ 7.85 (dd, 1H, J=1.2, 7.6 Hz), 7.80 (t, 1H, J=7.6 Hz), 7.59 (dd, 1H, J=1.2, 7.6 Hz), 6.71 (m, 1H), 3.99 (m, 2H), 3.49 (t, 2H, J=5.6 Hz), 3.02 (tt, 1H, J=3.2, 12 Hz), 2.76 (m, 1H), 2.65 (m, 2H), 2.03 (d, 1H, J=12 Hz), 1.75 (dt, 1H, J=13, 3.2 Hz), 1.60 (d, 1H, J=12 Hz), 1.42 (m, 2H), 1.22 (m, 2H), 1.13 (m, 1H), 0.74 (m, 2H), 0.61 (m, 2H); MS: 390 (M+H$^+$), 412 (M+Na).

1'-(2,4-Dichlorobenzenesulfonyl)-1',2',3',6'-tetrahydro-[2,4']bipyridinyl-6-carboxylic acid cyclopropylamide (2,4-dichlorobenzenesulfonyl chloride): $^1$H NMR (400 MHz, CD$_3$OD): δ 80.7 (d, 1H, J=8.8 Hz), 7.94 (dd, 1H, J=8, 1.2 Hz), 7.89 (t, 1H, J=8 Hz), 7.68 (d, 1H, J=2), 7.67 (dt, 1H, J=1.2, 7.6 Hz), 7.54 (dd, 1H, J=2, 8.4 Hz), 6.79 (m, 1H), 4.09 (m, 2H), 3.58 (t, 2H, J=5.6 Hz), 2.86 (m, 1H), 2.73 (m, 2H), 0.85 (m, 2H), 0.71 (m, 2H); MS: 452 (M+

1'-(3-Trifluoromethoxybenzenesulfonyl)-1',2',3',6'-tetrahydro-[2,4']bipyridinyl-6-carboxylic acid cyclopropylamide (3-trifluoromethoxybenzenesulfonyl chloride): $^1$H NMR (400 MHz, CD$_3$OD): δ 7.82 (dd, 1H, J=1.2, 7.6 Hz), 7.77 (m, 2H), 7.64 (s, 1H), 7.63 (t, 1H, J=8 Hz), 7.52 (dd, 1H, J=1.2, 8 Hz), 7.49 (m, 1H), 6.63 (m, 1H), 3.78 (m, 2H), 3.30 (t, 2H, J=5.6 Hz), 2.74 (m, 1H), 2.63 (m, 2H), 0.75 (m, 2H), 0.58 (m, 2H); MS: 468 (M+H$^+$).

1'-(3-Cyano-4-fluorobenzenesulfonyl)-1',2',3',6'-tetrahydro-[2,4']bipyridinyl-6-carboxylic acid cyclopropylamide (3-cyano-4-fluorobenzenesulfonyl chloride): $^1$H NMR (400 MHz, CD$_3$OD): δ 8.18-8.08 (m, 3H), 8.00 (bd, 1H, NH), 7.86 (t, 1H, J=8 Hz), 7.52 (dd, 1H, J=0.8, 8 Hz), 7.45 (t, 1H, J=8.8 Hz), 6.57 (m, 1H), 3.93 (m, 2H), 3.46 (t, 2H, J=5.6 Hz), 2.93 (m, 1H), 2.81 (m, 2H), 0.91 (m, 2H), 0.68 m, 2H); MS: 427 (M+H$^+$).

1'-(Pyridin-2-ylsulfonyl)-1',2',3',6'-tetrahydro-[2,4']bipyridinyl-6-carboxylic acid cyclopropylamide (pyridin-2-ylsulfonyl chloride): ¹H NMR (400 MHz, CD₃OD): δ 8.57 (m, 1H), 7.97 (dt, 1H, J=1.2, 7.2 Hz), 7.92 (m, 1H), 7.85 (dd, 1H, J=1.2, 7.6 Hz), 7.79 (t, 1H, J=7.6 Hz), 7.56 (dd, 1H, J=1.2, 7.6 Hz), 7.52 (ddd, 1H, J=1.6, 4.4, 7.6 Hz), 6.67 (m, 1H), 4.01 (m, 2H), 3.50 (t, 2H, J=5.6 Hz), 2.75 (m, 1H), 2.64 (m, 2H), 0.76 (m, 2H), 0.60 (m, 2H); MS: 385 (M+H⁺), 407 (M+Na).

1'-(Pyridin-3-ylsulfonyl)-1',2',3',6'-tetrahydro-[2,4']bipyridinyl-6-carboxylic acid cyclopropylamide (pyridin-3-ylsulfonyl chloride): ¹H NMR (400 MHz, CD₃OD): δ 8.91 (m, 1H), 8.69 (m, 1H), 8.18 (m, 1H), 7.79 (m, 2H), 7.55 (m, 2H), 6.67 (m, 1H), 3.81 (m, 2H), 3.33 (m, 2H), 2.75 (m, 1H), 2.65 (m, 2H), 0.72 (m, 2H), 0.58 (m, 2H); MS: 385 (M+H⁺), 407 (M+Na).

1'-(3-Trifluoromethylbenzylsulfonyl)-1',2',3',6'-tetrahydro-[2,4']bipyridinyl-6-carboxylic acid cyclopropylamide (3-trifluoromethylbenzylsulfonyl chloride): ¹H NMR (400 MHz, CD₃OD): δ 7.86 (dd, 1H, J=0.8, 7.6 Hz), 7.81 (t, 1H, J=7.6 Hz), 7.67 (s, 1H), 7.62 (d, 1H, J=7.6 Hz), 7.58 (dd, 1H, J=1.2, 7.6 Hz), 7.57 (d, 1H, J=7.6 Hz), 7.46 (t, 1H, J=7.6 Hz), 6.67 (m, 1H), 4.41 (s, 2H), 3.88 (m, 2H), 3.37 (t, 2H, J=5.6 Hz), 2.76 (m, 1H), 2.58 (m, 2H), 0.76 (m, 2H), 0.60 (m, 2H); MS: 466 (M+H⁺), 488 (M+Na).

1'-(3,5-Dichlorobenzenesulfonyl)-1',2',3',6'-tetrahydro-[2,4]bipyridinyl-6-carboxylic acid cyclopropylamide (3,5-dichlorobenzenesulfonyl chloride): ¹H NMR (400 MHz, CD₃OD): δ 7.85 (dd, 1H, J=1.2, 7.6 Hz), 7.80 (t, 1H, J=8 Hz), 7.72 (d, 2H, J=2 Hz), 7.68 (t, 1H, J=2 Hz), 7.57 (dd, 1H, J=1.2, 7.6 Hz), 6.66 (m, 1H), 3.79 (m, 2H), 3.34 (t, 2H, J=5.6 Hz), 2.76 (m, 1H), 2.66 (m, 2H), 0.75 (m, 2H), 0.60 (m, 2H); MS: 452 (M+H⁺).

1'-(2,4,6-Trifluorobenzenesulfonyl)-1',2',3',6'-tetrahydro-[2,4']bipyridinyl-6-carboxylic acid cyclopropylamide (2,4,6-trifluorobenzenesulfonyl chloride): ¹H NMR (400 MHz, CD₃OD): δ 7.85 (dd, 1H, J=1.6, 7.2 Hz), 7.81 (t, 1H, J=7.6 Hz), 7.59 (dd, 1H, J=0.8, 7.6 Hz), 7.02 (t, 2H, J=9.2 Hz), 6.71 (m, 1H), 3.90 (m, 2H), 3.50 (t, 2H, J=5.6 Hz), 2.76 (m, 1H), 2.70 (m, 2H), 0.76 (m, 2H), 0.62 (m, 2H); MS: 438 (M+H⁺).

1'-(2-Methylprop-1-ylsulfonyl)-1',2',3',6'-tetrahydro-[2,4']bipyridinyl-6-carboxylic acid cyclopropylamide (2-methylprop-1-ylsulfonyl chloride): ¹H NMR (400 MHz, CD₃OD): δ 8.51 (bd, 0.5H, NH), 7.85 (dd, 1H, J=0.8, 7.2 Hz), 7.80 (t, 1H, J=7.6 Hz), 7.59 (dd, 1H, J=0.8, 7.6 Hz), 6.73 (m, 1H), 3.92 (m, 2H), 3.43 (t, 2H, J=6 Hz), 2.85 (d, 2H, J=6.4 Hz), 2.76 (m, 1H), 2.69 (m, 2H), 2.15 (m, 1H), 1.01 (d, 6H, J=6.8 Hz), 0.75 (m, 2H), 0.61 (m, 2H); MS: 364 (M+H⁺).

1'-Cyclopentylsulfonyl-1',2',3',6'-tetrahydro-[2,4']bipyridinyl-6-carboxylic acid cyclopropylamide (cyclopentylsulfonyl chloride): ¹H NMR (400 MHz, CD₃OD): δ 7.98d, 1H, J=7.6 Hz), 7.933 (t, 1H, J=7.6 Hz), 7.74 (d, 1H, J=7.6 Hz), 6.86 (m, 1H), 4.11 (m, 2H), 3.72 (m, 1H), 3.62 (t, 2H, J=5.6 Hz), 2.89 (m, 1H), 2.81 (m, 2H), 2.02 (m, 4H), 1.80 (m, 2H), 1.67 (m, 2H), 0.87 (m, 2H), 0.72 (m, 2H); MS: 376 (M+H⁺).

1'-(Thiophen-3-ylsulfonyl)-1',2',3',6'-tetrahydro-[2,4']bipyridinyl-6-carboxylic acid cyclopropylamide (thiophen-3-ylsulfonyl chloride): ¹H NMR (400 MHz, CD₃OD): δ 8.19 (dd, 1H, J=0.8, 3.2 Hz), 7.96 (dd, 1H, J=1.6, 7.2 Hz), 7.91 (t, 1H, J=7.6 Hz), 7.69 (dd, 1H, J=1.2, 7.6 Hz), 7.67 (dd, 1H, J=3.2, 5.2 Hz), 7.41 (dd, 1H, J=1.2, 6.4 Hz), 6.79 (m, 1H), 3.89 (m, 2H), 3.40 (t, 2H, J=5.6 Hz), 2.87 (m, 1H), 2.80 (m, 2H), 0.87 (m, 2H), 0.72 (m, 2H); MS: 390 (M+H⁺).

Example 3

1'-(4-Trifluoromethoxybenzyl)-1',2',3',6'-tetrahydro-[2,4']bipyridinyl-6-carboxylic acid cyclopropylamide (9)

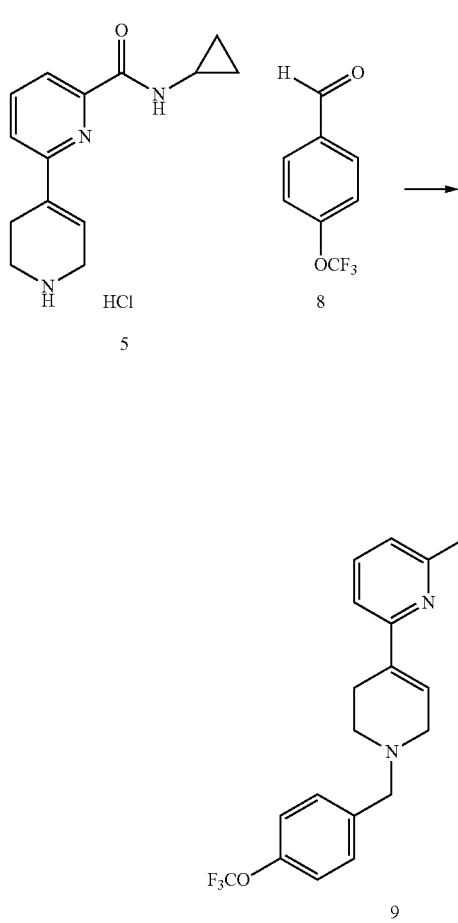

1'-(4-Trifluoromethoxybenzyl)-1',2',3',6'-tetrahydro-[2,4'] bipyridinyl-6-carboxylic acid cyclopropylamide (9) was prepared by adding diisopropyl ethyl amine to a suspension of compound 5 (72 mg, 0.25 mmol), 4-trifluoromethoxybenzaldehyde (8) (Aldrich) and 3 Å molecular sieves (200 mg, Aldrich). The mixture was stirred for 12 hours and NaCNBH₃ was added. The crude product was filtered and then purified on Prep TLC (10% MeOH in dichloromethane with 1% NH₄OH) to provide the title compound 9 (25 mg, yield 23%): ¹H NMR (400 MHz, CD₃OD, HCl-salt): δ 8.48 (bd, 1 h, NH), 7.88 (d, 1H, J=7.6 Hz), 7.83 (t, 1H, J=7.6 Hz), 7.65 (d, 1H, J=7.6 Hz), 7.57 (m, 2H), 7.32 (d, 2H, J=8.8 Hz), 6.68 (m, 1H), 4.39 (m, 2H), 3.85 (m, 2H), 3.68 (m, 1H), 3.26 (m, 1H), 3.12 (m, 1H), 2.82 (m, 1H), 2.71 (m, 1H), 0.72 m, 2H), 0.54 (m, 2H); MS: 418.

Example 4

2-[1-(4-Trifluoromethoxybenzenesulfonyl)-1,2,3,6-tetrahydropyridin-4-yl]-pyrimidine-4-carboxylic acid amide (15)

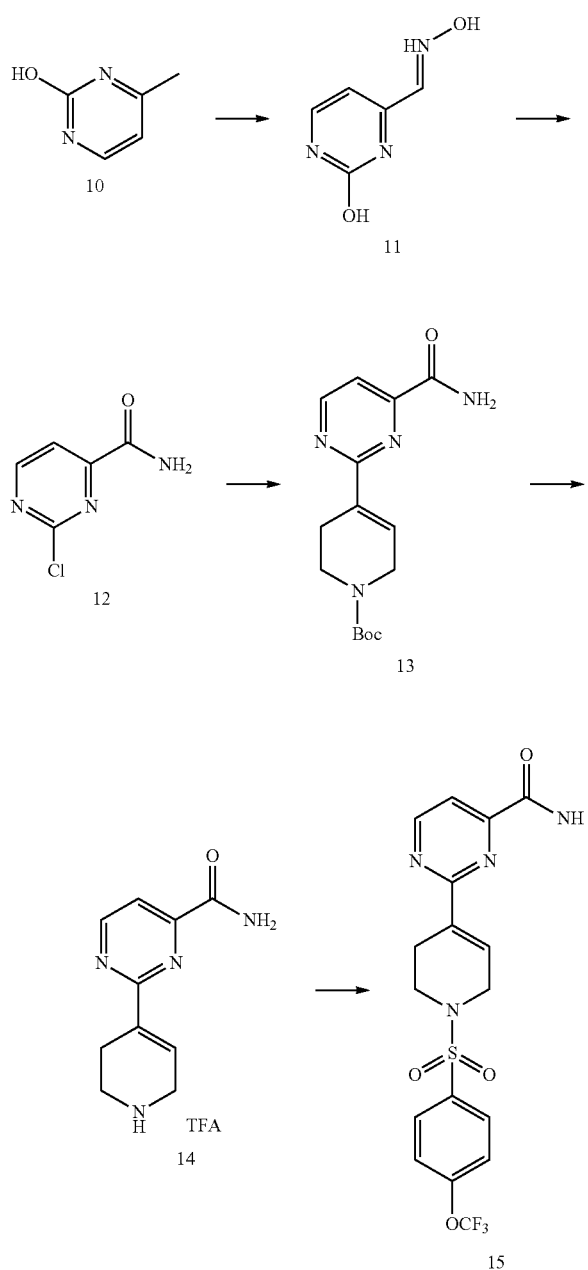

a) NaNO$_2$ (10.4 g, 150 mmol) was added in portions to a solution of compound 10 (14 g, 95 mmol, Aldrich) in 50 ml of glacial acetic acid. Exothermal reaction occurred and cooling with ice water was applied during the addition of NaNO$_2$. After the addition of NaNO$_2$, the mixture was stirred at room temperature for 3 hours. The resulting suspension was filtered and compound 11 was obtained as a solid, which was washed with ice water and then dried in oven at 50° C. for 12 hours.

b) Compound 11 was added into 40 ml of POCl$_3$. The resulting mixture was heated until no violent reaction occurred, and then the mixture was stirred at room temperature for 12 hours. Dimethyl aniline (5 ml) was added into the mixture and the resulting mixture was heated at 90° C. for 4 hours. After cooling to room temperature, the mixture was further cooled at 0° C. and ice was carefully added until no violent reaction was observed. The resulting mixture was extracted with diethyl ether (3×100 ml). The combined organic phase was washed with aqueous NaHCO$_3$ and then dried with Na$_2$SO$_4$, filtered, and concentrated to dryness to give compound 12.

c) The mixture of compound 12 (3 g, 19 mmol), compound 3 (5.9 g, 19.1 mmol), K$_2$CO$_3$ (5.8 g, 42 mmol), and palladium bistriphenylphosphine dichloride (1 g, 1.52 mmol) in 50 ml of a solvent mixture of ethyleneglycol dimethyl ether/ethanol/water in a ratio of 2/1/2 was heated in an oil bath at 95° C. while stirring for 2 hours. After cooling to room temperature, the solvent was removed under reduced pressure. The residue was dissolved in EtOAc (150 ml) and washed with brine (2×100 ml). The combined aqueous phase was extracted with EtOAc (2×150 ml). The combined organic phase was dried with Na$_2$SO$_4$, filtered and concentrated to dryness. The obtained solid was washed with 50% EtOAc in hexane and then dried to give pure compound 13 (6 g, yield 100%).

d) To a solution of compound 13 (140 mg, 0.46 mmol) in 5 ml of dichloromethane at 0° C. was added 1 ml of trifluoroacetic acid (TFA). After one hour, the mixture was concentrated to dryness to give crude compound 14 which was used without further purification.

e) Diisopropyl ethyl amine and 4-(trifluoromethoxy)benzenesulfonyl chloride were sequentially added to a solution of compound 14 (100 mg, 0.23 mmol) in dichloromethane at 0° C. The reaction mixture was allowed to warm to room temperature and it was purified without work-up on Combi-Flash® with a gradient of 50-80% EtOAc in hexane to provide the title compound 2-[1-(4-trifluoromethoxybenzenesulfonyl)-1,2,3,6-tetrahydropyridin-4-yl]-pyrimidine-4-carboxylic acid amide (15) as a white solid (30 mg, yield 30%). $^1$H NMR (400 MHz, CD$_3$OD): δ 8.98 (d, 1H, J=5.2 Hz), 8.36 (bd, 1H, NH), 7.99 (d, 2H, J=9.2 Hz), 7.96 (bd, 1H, NH), 7.80 (d, 1H, J=5.2 Hz), 7.63 (m, 2H), 7.39 (m, 1H), 3.89 (m, 2H), 3.34 (m, 2H), 2.73 (m, 2H); MS: 429, 451.

Similarly, 2-[1-(3-trifluoromethylbenzenesulfonyl)-1,2,3,6-tetrahydropyridin-4-yl]-pyrimidine-4-carboxylic acid amide was prepared from compound 14 and 3-trifluoromethylbenzenesulfonyl chloride. $^1$H NMR (400 MHz, CD$_3$OD): δ 8.98 (d, 1H, J=4.8 Hz), 8.36 (bd, 1H, NH), 8.18 (d, 1H, J=7.6 Hz), 8.11 (d, 1H, J=8.4 Hz), 8.079 (s, 1H), 7.96 (bd, 1H, NH), 7.91 (t, 1H, J=4.0 Hz), 7.80 (d, 1H, J=4.8 Hz), 7.40 (m, 1H), 3.92 (m, 2H), 3.36 t, 2H, J=5.6 Hz), 2.72 (m, 2H); MS: 413 (M+H$^+$), 454 (M+Na).

Example 5

1'-(3-Trifluoromethylbenzenesulfonyl)-1',2',3',6'-tetrahydro-[3,4']bipyridinyl-2-carboxylic acid methyl ester (19)

1'-(3-Trifluoromethylbenzenesulfonyl)-1',2',3',6'-tetrahydro-[3,4']bipyridinyl-2-carboxylic acid cyclopropylmethylamide (21)

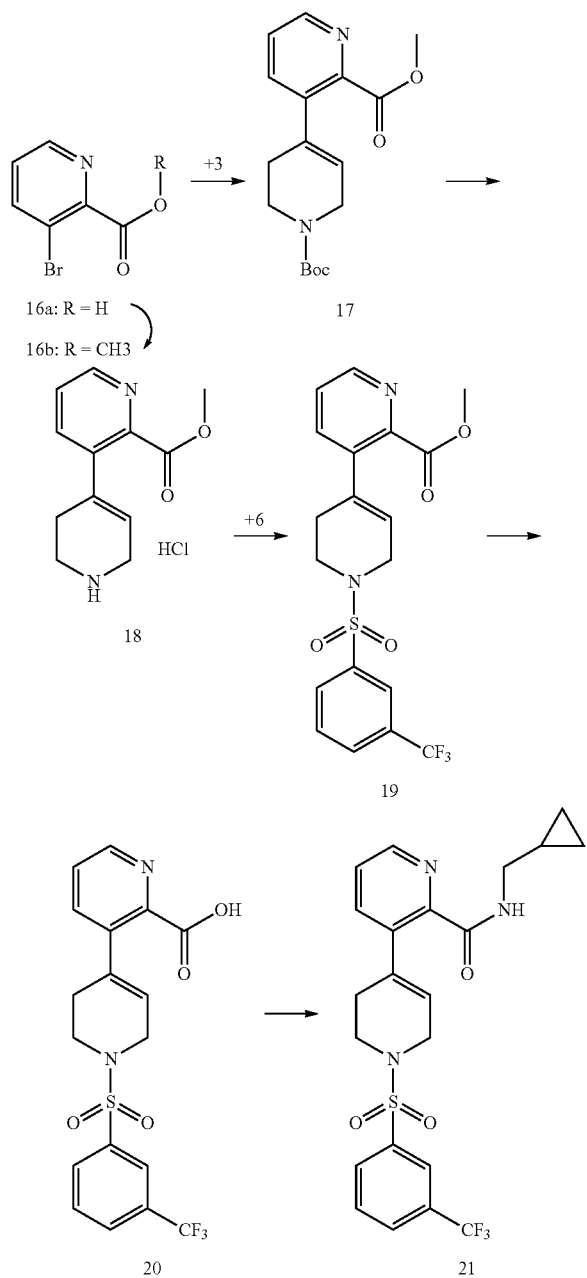

a) To the methanol solution of compound 16a (1 g, 4.9 mmol, Matrix) at room temperature was added a few drops of concentrated sulfuric acid. The mixture was stirred for 12 hours. After removal of MeOH, the crude residue was purified on silica gel column on CombiFlash® with 20-50% EtOAc in hexane to provide compound 16b (450 mg, 41%). Compound 17 (yield 82%) was synthesized following the procedure described in Example 1 for preparing compound 4 starting from compound 16b.

b) 1'-(3-Trifluoromethylbenzenesulfonyl)-1',2',3',6'-tetrahydro-[3,4']bipyridinyl-2-carboxylic acid methyl ester (19) was prepared by first treating compound 17 with 4N HCl to obtain compound 18 according to the procedure described in Example 4 for preparing compound 5. Compound 18 was allowed to react with 3-trifluoromethylbenzenesulfonyl chloride (6) to obtain compound 19 (yield 38%) as described in Example 2 for preparing compound 7. $^1$H NMR (400 MHz, CDCl$_3$): δ 8.75 (dd, 1H, J=2, 5.2 Hz), 8.11 (s, 1H), 8.05 (d, 1H, J=9.2 Hz), 7.92 (d, 1H, J=8 Hz), 7.76 (t, 1H, J=8 Hz), 7.71 (dd, 1H, J=2, 7.6 Hz), 7.61 (dd, 1H, J=4.8, 8 Hz), 5.59 (m, 1H), 3.93 (s, 3H), 3.83 (m, 2H), 3.45 (t, 2H, J=5.6 Hz), 2.51 (m, 2H); MS: 427 (M+H$^+$).

c) Compound 19 was treated with mixture of aqueous 2 N NaOH in methanol at room temperature for 12 hours, and then the mixture was cooled to 0° C. and acidified with dilute aqueous HCl to pH 1. The resulting mixture was freeze-dried and the crude compound 20 was used without further purification. $^1$H NMR (400 MHz, CD$_3$OD): δ 8.67 (dd, 1H, J=4.4, 2 Hz), 8.12 (s, 1H), 8.05 (d, 1H, J=8 Hz), 7.92 (d, 1H, J=8 Hz), 7.75 (t, 1H, J=8 Hz), 7.54 (dd, 1H, J=7.6, 1.6 Hz), 7.45 (dd, 1H, J=4.8, 8 Hz), 5.539 (m, 1H), 3.82 (m, 2H), 3.45 (t, 2H, J=5.6 Hz), 2.51 (m, 2H); MS: 427, 450.

d) Diisopropyl ethyl amine (72 ml, 0.39 mmol) and cyclopropylmethyl amine were sequentially added to a suspension of compound 20 (53 mg, 0.13 mmol), HOBt (17 mg, 0.13 mmol), and N-(3-dimethylaminopropyl)-N' ethylcabodiimide hydrochloride (25 mg, 0.13 mmol) in dichloromethane at 0° C. The resulting mixture was allowed to warm to room temperature. The reaction mixture was purified without work-up on CombiFlash® with a gradient of 50-80% EtOAc in hexane to obtain the title compound 21 (7 mg, yield 12%). $^1$H NMR (400 MHz, CDCl$_3$): δ 8.28 (dd, 1H, J=1.6, 4.8 Hz), 8.00 (bt, 1H, NH), 7.86 (s, 1H), 7.79 (d, 1H, J=7.6 Hz), 7.65 (d, 1H, J=7.6 Hz), 7.48 (t, 1H, J=8 Hz), 7.27 (dd, 1H, J=2, 8 Hz), 7.17 (dd, 1H, J=4.4, 7.6 Hz), 5.20 (m, 1H), 3.58 (m, 2H), 3.23 (t, 2H, J=5.6 Hz), 2.97 (dd, 2H, J=6, 7.2 Hz), 2.28 (m, 2H), 0.79 (m, 1H), 0.30 (m, 2H), 0.010 (m, 2H); MS: 468 (M+H$^+$).

Similarly, the following compounds were prepared by reacting compound 20 with an appropriate reagent (in parenthesis):

1'-(3-Trifluoromethylbenzenesulfonyl)-1',2',3',6'-tetrahydro-[3,4']bipyridinyl-2-carboxylic acid 2,2,2-trifluoroethylamide (2,2,2-trifluoroethylamine): $^1$H NMR (400 MHz, CDCl$_3$): δ 8.55 (dd, 1H, J=1.6, 4.4 Hz), 8.55 (bd, 1H, NH), 8.12 (s, 1H), 8.04 (d, 1H, J=8 Hz), 7.90 (d, 1H, J=7.6 Hz), 7.74 (t, 1H, J=7.6 Hz), 7.57 (dd, 1H, J=1.6, 8 Hz), 7.49 (dd, 1H, J=4.8, 7.6 Hz), 5.50 (m, 1H), 4.03 (m, 2H), 3.84 (m, 2H), 3.48 (t, 2H, J=5.6 Hz), 2.50 (m, 2H); MS: 494 (M+H$^+$), 516 (M+Na).

1'-(3-Trifluoromethylbenzenesulfonyl)-1',2',3',6'-tetrahydro-[3,4']bipyridinyl-2-carboxylic acid 3,3,3-trifluoropropylamide (3,3,3-trifluoropropylamine): $^1$H NMR (400 MHz, CDCl$_3$): δ 8.52 (dd, 1H, J=2, 4.8 Hz), 8.48 (bt, 1H, NH), 8.12 (s, 1H), 8.05 (d, 1H, J=8 Hz), 7.90 (d, 1H, J=8 Hz), 7.74 (t, 1H, J=7.6 Hz), 7.56 (dd, 1H, J=2, 8 Hz), 7.46 (dd, 1H, J=4.8, 8 Hz), 5.48 (m, 1H), 3.85 (m, 2H), 3.65 (q, 2H, J=6.4 Hz), 3.48 (t, 2H, J=5.2 Hz), 2.50 (m, 2H), 2.42 (m, 2H); MS: 508 (M+H$^+$), 530 (M+Na).

The following compounds were prepared according to the procedure of Example 5 using appropriate reagents:

1'-(4-Trifluoromethoxybenzenesulfonyl)-1',2',3',6'-tetrahydro-[3,4']bipyridinyl-2-carboxylic acid 2,2,2-trifluoroethylamide: $^1$H NMR (400 MHz, CDCl$_3$): δ 8.55 (dd, 1H, J=1.6, 4.8 Hz), 8.54 (bd, 1H, NH), 7.91 (m, 2H), 7.56 (dd, 1H, J=1.6, 7.6 Hz), 7.47 (dd, 1H, J=4.8, 7.6 Hz), 7.40 (m, 2H), 5.49 (m, 1H), 4.02 (m, 2H), 3.82 (m, 2H), 3.48 (t, 2H, J=5.6 Hz), 2.49 (m, 2H); MS: 510 (M+H$^+$), 532 (M+Na).

Example 6

1'-(3-Trifluoromethylbenzenesulfonyl)-1',2',3',6'-tetrahydro-[2,4']bipyridinyl-6-carboxylic acid cyclopropylmethylamide (27)

1'-(3-Trifluoromethylbenzenesulfonyl)-1',2',3',6'-tetrahydro-[2,4']bipyridinyl-6-carboxylic acid amide (28)

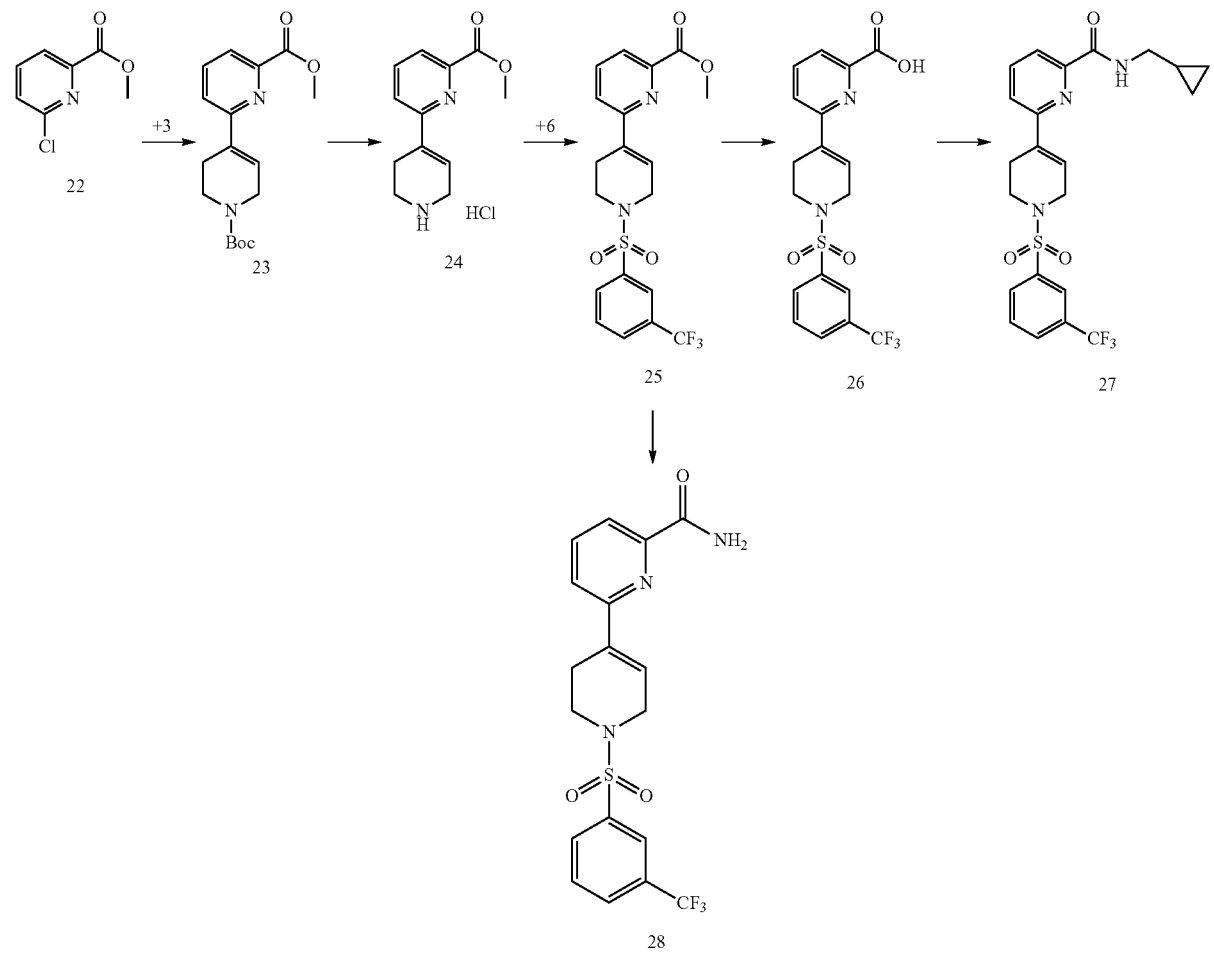

1'-(4-Trifluoromethoxybenzenesulfonyl)-1',2',3',6'-tetrahydro-[3,4']bipyridinyl-2-carboxylic acid 3,3,3-trifluoropropylamide: $^1$H NMR (400 MHz, CDCl$_3$): δ 8.52 (dd, 1H, J=2, 4.8 Hz), 8.47 (bt, 1H, NH), 7.91 (m, 2H), 7.54 (dd, 1H, J=2, 8 Hz), 7.45 (dd, 1H, J=3.2, 8 Hz), 7.40 (m, 2H), 5.47 (m, 1H), 3.84 (m, 2H), 3.65 (q, 2H, J=6.4, 6.8 Hz), 3.48 (t, 2H, J=5.2 Hz), 2.51 (m, 2H), 2.42 (m, 2H); MS: 524 (M+546 (M+Na).

1'-(4-Trifluoromethoxybenzenesulfonyl)-1',2',3',6'-tetrahydro-[3,4']bipyridinyl-2-carboxylic acid cyclopropylmethylamide: $^1$H NMR (400 MHz, CDCl$_3$): δ 8.29 (dd, 1H, J=2, 4.8 Hz), 8.07 (bt, 1H, NH), 7.65 (m, 2H), 7.31 (dd, 1H, J=1.6, 7.6 Hz), 7.20 (dd, 1H, J=4.8, 7.6 Hz), 7.16 (d, 2H, J=8 Hz), 5.22 (m, 1H), 3.57 (m, 2H), 3.23 (t, 2H, J=5.2 Hz), 3.00 (dd, 2H, J=5.6, 7.2 Hz), 2.28 (m, 2H), 0.81 (m, 1H), 0.32 (m, 2H), 0.026 (m, 2H); MS: 482 (M+H$^+$), 504 (M+Na).

a) 1'-(3-Trifluoromethylbenzenesulfonyl)-1',2',3',6'-tetrahydro-[2,4]-bipyridinyl-6-carboxylic acid cyclopropylmethylamide (27) was synthesized according to the procedure described in Example 5 for preparing compound 21 in Example 5 using compound 22 as the starting material instead of compound 16. $^1$H NMR (400 MHz, CDCl$_3$): δ 8.01 (s, 1H), 7.98 (dd, 1H, J=0.8, 8 Hz), 7.95 (d, 1H, J=8 Hz), 7.91 (bt, 1H, NH), 7.77 (d, 1H, J=8 Hz), 7.71 (t, 1H, J=7.6 Hz), 7.62 (t, 1H, J=7.6 Hz), 7.38 (dd, 1H, J=0.8, 8 Hz), 6.46 (m, 1H), 3.81 (m, 2H), 3.34 (t, 2H, J=6 Hz), 3.24 (dd, 2H, J=6, 6.8 Hz), 2.71 (m, 2H), 0.98 (m, 1H), 0.45 (m, 2H), 0.79 (m, 2H); MS: 466 (M+H$^+$), 489 (M+Na).

Similarly, the following compounds were prepared starting from compound 26 using an appropriate reagent (in parenthesis):

1'-(3-Trifluoromethylbenzenesulfonyl)-1',2',3',6'-tetrahydro-[2,4']-bipyridinyl-6-carboxylic acid 2,2,2-trifluoroethylamide (2,2,2-trifluoroethylamine): $^1$H NMR (400 MHz, CDCl$_3$): δ 8.24 (bt, 1H, NH), 8.13 (s, 1H), 8.12 (d, 1H, J=7.6 Hz), 8.07 (d, 1H, J=8 Hz), 7.89 (d, 1H, J=7.6 Hz), 7.88 (t, 1H, J=7.6 Hz), 7.74 (t, 1H, J=7.6 Hz), 7.56 (d, 1H, J=8 Hz), 6.59 (m, 1H), 4.15 (m, 2H), 3.95 (m, 2H), 3.46 (t, 2H, J=5.6 Hz), 2.81 (m, 2H); MS: 494 (M+516 (M+Na).

1'-(3-Trifluoromethylbenzenesulfonyl)-1',2',3',6'-tetrahydro-[2,4']-bipyridinyl-6-carboxylic acid 3,3,3-trifluoropropylamide (3,3,3-trifluoropropylamine): $^1$H NMR (400 MHz, CDCl$_3$): δ 8.25 (bt, 1H, NH), 8.13 (s, 1H), 8.081 (m, 1H), 7.90 (d, 1H, J=7.6 Hz), 7.85 (t, 1H, J=8 Hz), 7.74 (t, 1H, J=8 Hz), 7.53 (dd, 1H, J=0.8, 8.4 Hz), 6.58 (m, 1H), 3.93 (m, 2H), 3.78 (q, 2H, J=6.4 Hz), 3.45 (t, 2H, J=6 Hz), 2.81 (m, 2H), 2.49 (m, 2H); MS: 508 (M+H$^+$), 530 (M+Na).

The following compounds were prepared according to the procedure of Example 6 using appropriate reagents:

1'-(4-Trifluoromethoxybenzenesulfonyl)-1',2',3',6'-tetrahydro-[2,4]-bipyridinyl-6-carboxylic acid 2,2,2-trifluoroethylamide: $^1$H NMR (400 MHz, CDCl$_3$): δ 8.256 (bd, 1H, NH), 8.12 (dd, 1H, J=0.8, 7.6 Hz), 7.93 (m, 2H), 7.88 t, 1H, J=8 Hz), 7.56 (dd, 1H, J=1.2, 8 Hz), 7.40 (m, 2H), 6.58 (m, 1H), 4.15 (m, 2H), 3.92 (m, 2H), 3.44 (t, 2H, J=5.6 Hz), 2.82 (m, 2H); MS: 510 (M+H$^+$), 532 (M+Na).

1'-(4-Trifluoromethoxybenzenesulfonyl)-1',2',3',6'-tetrahydro-[2,4']-bipyridinyl-6-carboxylic acid 3,3,3-trifluoropropylamide: $^1$H NMR (400 MHz, CDCl$_3$): δ 8.29 (bt, 1H, NH), 8.10 (dd, 1H, J=0.8, 7.6 Hz), 7.93 (m, 2H), 7.86 (t, 1H, J=7.6 Hz), 7.54 (dd, 1H, J=1.2, 8 Hz), 7.40 (dd, 2H, J=0.8, 8.8 Hz), 6.58 (m, 1H), 3.92 (m, 2H), 3.78 (m, 2H), 3.43 (t, 2H, J=5.6 Hz), 2.81 (m, 2H), 2.49 (m, 2H); MS: 524 (M+H$^+$), 546 (M+Na).

1'-(4-Trifluoromethoxybenzenesulfonyl)-1',2',3',6'-tetrahydro-[2,4]'-bipyridinyl-6-carboxylic acid 4-fluorophenylamide: $^1$H NMR (400 MHz, CD$_3$OD): δ 8.09-7.96 (m, 4H), 7.80 (m, 2H), 7.76 (m, 2H), 7.55 (m, 2H), 7.15 (m, 2H), 6.85 (m, 1H), 3.94 (m, 2H), 3.46 (t, 2H, J=6 Hz), 2.88 (m, 2H); MS: 522 (M+544 (M+Na).

b) 1'-(3-Trifluoromethylbenzenesulfonyl)-1',2',3',6'-tetrahydro-[2,4']bipyridinyl-6-carboxylic acid amide (28) was prepared as follows. A solution of compound 25 (55 mg, 0.13 mmol) in 2 M NH$_3$ in methanol was stirred at room temperature for 12 hours. The mixture was concentrated and the solid was washed with 20% EtOAc in hexane and dried to give the title compound 28 (44 mg, yield 85%). $^1$H NMR (400 MHz, CD$_3$OD): δ 8.16 (d, 1H, J=7.6 Hz), 8.12 (s, 1H), 8.00 (d, 1H, J=8 Hz), 7.98 (dd, 1H, J=1.2, 7.6 Hz), 7.91 (t, 1H, J=7.6 Hz), 7.86 (t, 1H, J=8 Hz), 7.70 (dd, 1H, J=1.2, 8 Hz), 6.78 (m, 1H), 3.93 (m, 2H), 3.45 (t, 2H, J=6 Hz), 2.79 (m, 2H); MS: 412 (M+H$^+$), 434 (M+Na).

Similarly, the following compounds were prepared starting from compound 25 using an appropriate reagent (in parenthesis):

1'-(3-Trifluoromethylbenzenesulfonyl)-1',2',3',6'-tetrahydro-[2,4']bipyridinyl-6-carboxylic acid 2-hydroxyethylamide (ethanol amine) [the product was purified without an aqueous work-up on CombiFlash® (44 mg, yield 70%)]: $^1$H NMR (400 MHz, CD$_3$OD): 8.15 (m, 1H), 8.12 (s, 1H), 8.022-7.85 (m, 4H), 7.69 (m, 1H), 6.79 (m, 1H), 3.93 (m, 2H), 3.73 (m, 2H), 3.57 (m, 2H), 3.45 (m, 2H), 2.80 (m, 2H); MS: 456 (M+H$^+$), 478 (M+Na).

1'-(3-Trifluoromethylbenzenesulfonyl)-1',2',3',6'-tetrahydro-[2,4']bipyridinyl-6-carboxylic acid 1,3-dihydroxyprop-2-ylamide (2-amino-1,3-propanediol) [the product was purified without an aqueous work-up on CombiFlash® (57 mg, yield 53%)]: $^1$H NMR (400 MHz, CD$_3$OD): δ 8.16 (d, 1H, J=8 Hz), 8.13 (s, 1H), 8.00 (m, 1H), 7.93 (t, 1H, J=7.6 Hz), 7.86 (t, 1H, J=7.6 Hz), 7.71 (dd, 1H, J=1.2, 8 Hz), 6.77 (m, 1H), 4.13 (m, 1H), 3.92 (m, 2H), 3.81 (dd, 2H, J=5.2, 11 Hz), 3.74 (dd, 2H, J=5.2, 11 Hz), 3.45 (t, 2H, J=6 Hz), 2.80 (m, 2H); MS: 486 (M+H$^+$).

Example 7

1'-(3-Trifluoromethylbenzenesulfonyl)-1',2',3',6'-tetrahydro-[2,4']bipyridinyl-6-carbonitrile (32)

N-Cyclopropylmethyl-1'-(4-trifluoromethoxybenzenesulfonyl)-1',2',3',6'-tetrahydro-[2,4']bipyridinyl-6-carboxamidine (34)

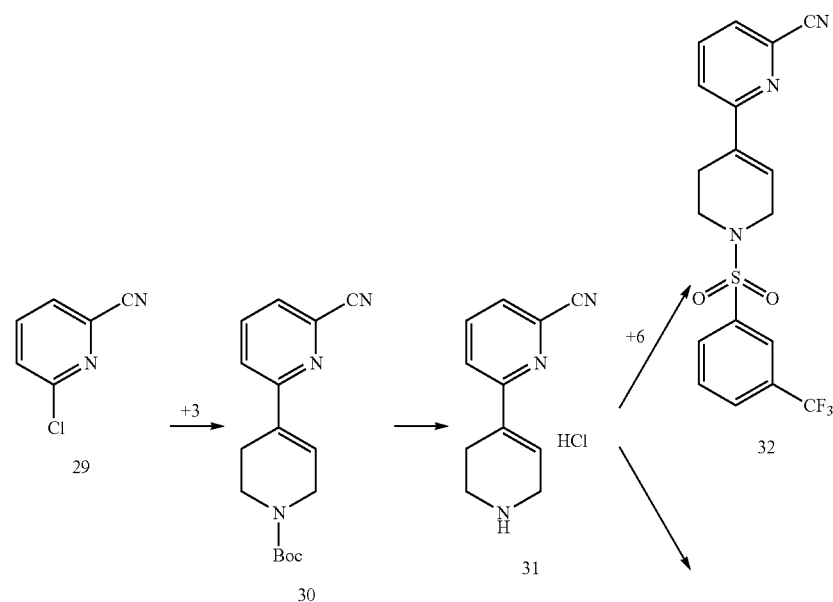

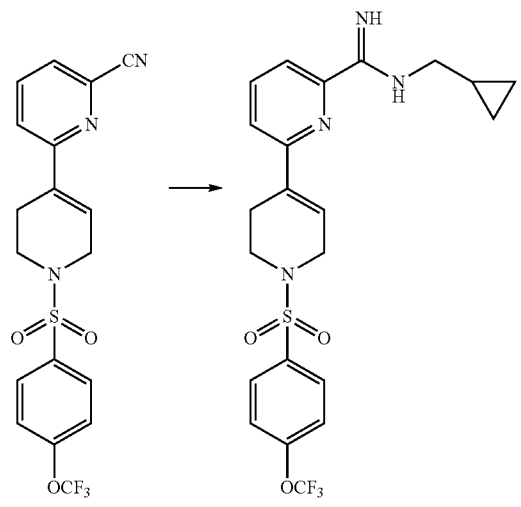

a) 1'-(3-Trifluoromethylbenzenesulfonyl)-1',2',3',6'-tetrahydro-[2,4']bipyridinyl-6-carbonitrile (32) was synthesized similarly to compound 7 in Example 1 starting with 2-chloro-6-cyanopyridine (22) instead of compound 1. $^1$H NMR (400 MHz, CD$_3$OD): δ 8.15 (d, 1H, J=8.4 Hz), 8.12 (s, 1H), 8.00 (d, 1H, J=7.6 Hz), 7.92 (m, 1H), 7.86 (m, 1H), 7.80 (m, 1H), 7.70 (m, 1H), 6.76 (m, 1H), 3.93 (m, 2H), 3.43 (m, 2H), 2.73 (m, 2H); MS: 394 (M+H$^+$).

b) N-Cyclopropylmethyl-1'-(4-trifluoromethoxybenzenesulfonyl)-1',2',3',6'-tetrahydro-[2,4']bipyridinyl-6-carboxamidine (34) was synthesized as follows. Compound 33 was prepared according to the procedure described above for preparing compound 32 using 4-(trifluoromethoxy)benzenesulfonyl chloride instead of 3-trifluoromethylbenzenesulfonyl chloride. To a solution of compound 33 (154 mg, 0.37 mmol) in ethanol was added cyclopropylmethylamine (52 mg, 0.75 mmol) and the resulting solution was heated at 55° C. for 12 hours. The mixture was purified, without an aqueous work-up, on CombiFlash® and further purified by Prep-TLC to obtain the title compound 34 (7 mg, yield 4%). $^1$H NMR (400 MHz, CD$_3$OD): δ 7.97-7.85 (m, 4H), 7.77 (d, 1H, J=8 Hz), 7.43 (d, 2H, J=8.8 Hz), 6.76 (m, 1H), 3.81 (m, 2H), 3.32 (m, 4H), 2.71 (m, 2H), 1.14 (m, 1H), 0.58 (m, 2H), 0.31 (m, 2H); MS: 481 (M+H$^+$).

Example 8

2-[1-(3-Trifluoromethylbenzenesulfonyl)-1,2,3,6-tetrahydropyridin-4-yl]pyrimidine-4-carboxylic acid cyclopropylamide (39)

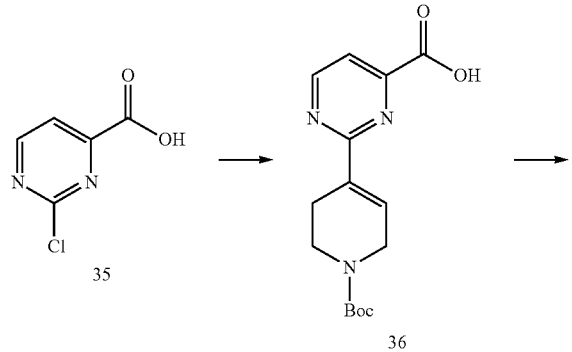

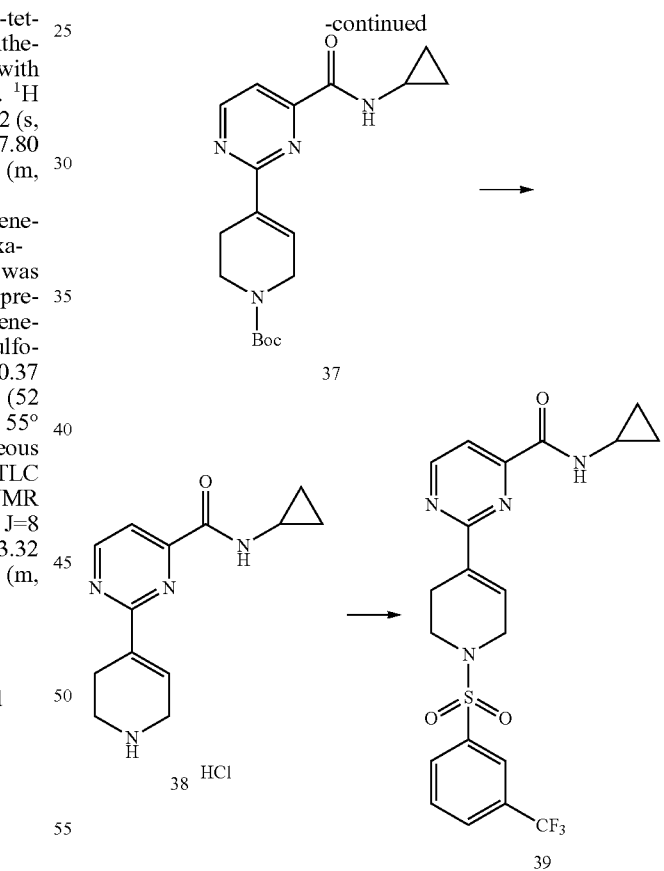

2-[1-(3-Trifluoromethylbenzenesulfonyl)-1,2,3,6-tetrahydropyridin-4-yl]pyrimidine-4-carboxylic acid cyclopropylamide (39) was prepared as follows:

a) Compound 37 was synthesized according to the procedure described in Example 1 for preparing compound 4 starting from compound 35 (158 mg, 1 mmol, Chem-Impex) to first obtain compound 36. Diisopropyl ethyl amine (138 μl, 0.75 mmol) and cyclopropylamine (20 μl, 0.27 mmol) were added sequentially to a solution of compound 36 (75 mg, 0.25 mmol), HOBt (33 mg, 0.25 mmol), N-(3-dimethylaminopropyl)-N' ethylcabodiimide hydrochloride (53 mg, 0.27 mmol) in dichloromethane at 0° C. The mixture was allowed to warm to room temperature and stirred for 3 hours. The mixture was concentrated to dryness to give the crude compound 37 (150 mg, yield 50%).

b) The residue from step a) was dissolved in EtOAc and then HCl in 1,4-dioxane was added at 0° C. The mixture was slowly warmed to room temperature and stirred for 12 hours. The solid was filtered and washed with hexane and dried to give compound 38. To a suspension of compound 38 in dichloromethane at 0° C. was added diisopropyl ethyl amine (138 ml, 0.75 mmol) followed by 3-trifluoromethylbenzenesulfonyl chloride. The reaction was complete within ten minutes and the crude product was purified on CombiFlash® without an aqueous work-up to give the title compound 39 (28 mg, yield 25% from compound 36). $^1$H NMR (400 MHz, CD$_3$OD): 8.81 (m, 1H), 8.04 (m, 2H), 7.86 (m, 1H), 7.71 (m, 2H), 7.28 (m, 1H), 3.84 (m, 2H), 3.30 (m, 2H), 2.77 (m, 1H), 2.68 (m, 2H), 0.74 (m, 2H), 0.59 (m, 2H); MS: 453 (M+H$^+$).

The following compounds were prepared according to the procedure described above:

2-[1-(3-Trifluoromethylbenzenesulfonyl)-1,2,3,6-tetrahydropyridin-4-yl]pyrimidine-4-carboxylic acid cyclopropylmethylamide: $^1$H NMR (400 MHz, CDCl$_3$): δ 8.82 (d, 1H, J=4.8 Hz), 8.05 (s, 1H), 7.97 (d, 1H, J=8.4 Hz), 7.89 (bt, 1H, NH), 7.87 (d, 1H, J=4.8 Hz), 7.81 (d, 1H, J=7.6 Hz), 7.65 (t, 1H, J=7.2 Hz), 7.17 (m, 1H), 3.90 (m, 2H), 3.37 (t, 2H, J=5.6 Hz), 3.28 (dd, 2H, J=5.6, 7.2 Hz), 2.80 (m, 2H), 1.01 (m 1H), 0.52 (m, 2H), 0.23 (m, 2H); MS: 467 (M+H$^+$).

2-[1-(4-Trifluoromethoxybenzenesulfonyl)-1,2,3,6-tetrahydropyridin-4-yl]pyrimidine-4-carboxylic acid cyclopropylamide: $^1$H NMR (400 MHz, CD$_3$OD): δ 8.78 (d, 1H, J=5.2 Hz), 7.85 (m, 2H), 7.70 (d, 1H, J=5.2 Hz), 7.38 (m, 2H), 7.23 (m, 1H), 3.80 (m, 2H), 3.27 (t, 2H, J=6 Hz), 2.75 (m, 1H), 2.69 (m, 2H), 0.73 (m, 2H), 0.58 (m, 2H); MS: 469 (M+H$^+$).

Example 9

5-Chloro-1'-(3-trifluoromethylbenzenesulfonyl)-1',2',3',6'-tetrahydro-[2,4']bipyridinyl-6-carboxylic acid cyclopropylamide (44)

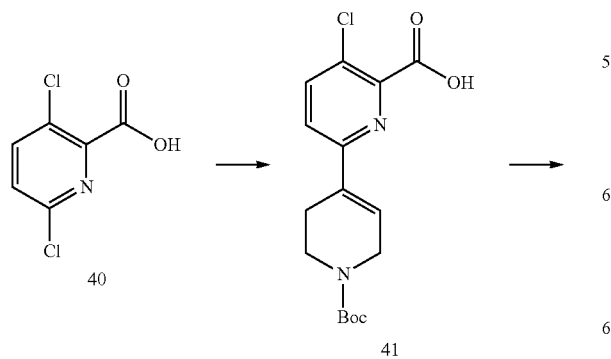

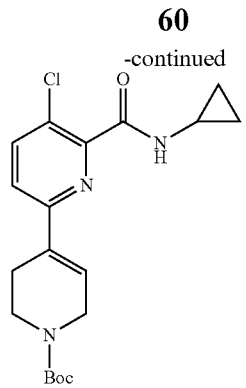

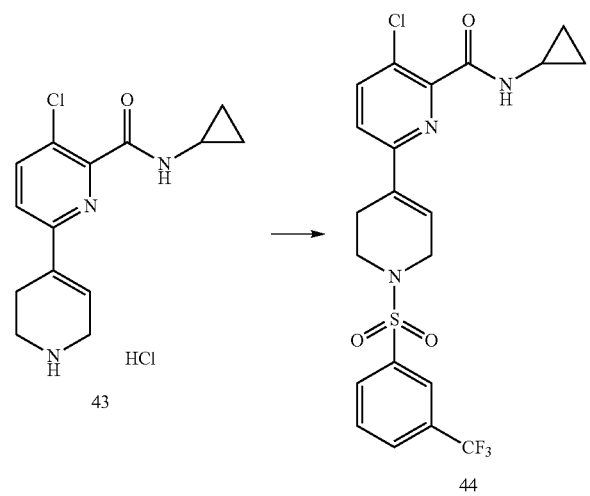

5-Chloro-1'-(3-trifluoromethylbenzenesulfonyl)-1',2',3',6'-tetrahydro-[2,4]'bipyridinyl-6-carboxylic acid cyclopropylamide (44) was synthesized according to the procedure described in Example 8 for preparing compound 39 starting from 3,6-dichloropyridine-2-carboxylic acid (40) (Matrix) instead of compound 35. $^1$H NMR (400 MHz, CD$_3$OD): δ 8.15 (d, 1H, J=7.6 Hz), 8.12 (s, 1H), 8.02 (d, 1H, J=8.4 Hz), 7.86 (m, 2H), 7.59 (d, 1H, J=8.4 Hz), 6.72 (m, 1H), 3.90 (m, 2H), 3.42 (t, 2H, J=5.6 Hz), 2.87 (m, 1H), 2.72 (m, 2H), 0.84 (m, 2H), 0.66 (m, 2H); MS: 486 (M+H$^+$).

Similarly, 5-chloro-1'-(4-trifluoromethoxybenzenesulfonyl)-1',2',3',6'-tetra-hydro-[2,4']bipyridinyl-6-carboxylic acid cyclopropylamide was synthesized using 4-trifluoromethoxybenzenesulfonyl chloride at the last step instead of 3-trifluoromethylbenzenesulfonyl chloride. $^1$H NMR (400 MHz, CD$_3$OD): δ 7.99 (m, 2H), 7.85 (d, 1H, J=8.4 Hz), 7.59 (d, 1H, J=8.4 Hz), 7.54 (m, 2H), 6.72 (m, 1H), 3.87 (m, 2H), 3.39 (t, 2H, J=5.6 Hz), 2.87 (m, 1H), 2.73 (m, 2H), 0.83 (m, 2H), 0.66 (m, 2H); MS: 502 (M+H$^+$).

Example 10

6'-Oxo-1'-(3-trifluoromethylbenzenesulfonyl)-1',2', 3',6'-tetrahydro-[2,4']bipyridinyl-6-carboxylic acid cyclopropylamide (45)

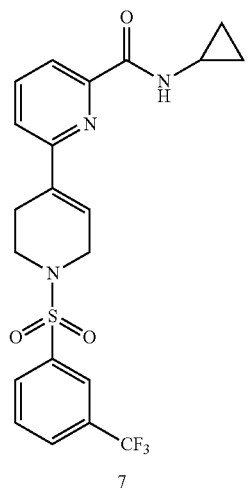

7

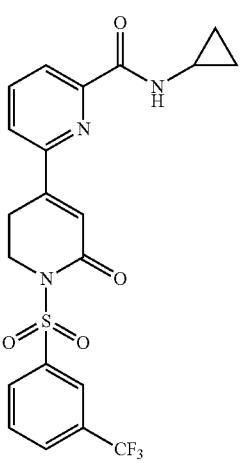

45

6'-Oxo-1'-(3-trifluoromethylbenzenesulfonyl)-1',2',3',6'-tetrahydro-[2,4']bipyridinyl-6-carboxylic acid cyclopropylamide (45) was prepared as follows. Excess MnO$_2$ was added to a solution of compound 7 prepared in Example 2 (140 mg, 0.31 mmol) in dichloromethane (10 ml) at room temperature. The resulting suspension was stirred for 12 hours. The mixture was filtered through paper and purified on the Combi-Flash® without an aqueous work-up to give the title compound 45 (11 mg, yield 8%). $^1$H NMR (400 MHz, CDCl$_3$): δ 8.27 (d, 1H, J=9.6 Hz), 8.26 (s, 1H), 8.18 (dd, 1H, J=0.8, 7.6 Hz), 7.87 (t, 1H, J=8 Hz), 7.84 (d, 1H, J=8 Hz), 7.77 (bd, 1H, NH), 7.65 (m, 2H), 6.54 (m, 1H), 4.19 (t, 2H, J=6.4 Hz), 3.09 (dt, J=1.2, 6.8 Hz), 2.84 (m, 1H), 0.86 (m, 2H), 0.60 (m, 2H); MS: 466 (M+H$^+$).

Example 11

6-[8-(3-Trifluoromethylbenzenesulfonyl)-8-aza-bicyclo[3.2.1]oct-2-en-3-yl]pyridine-2-carboxylic acid cyclopropylamide (55)

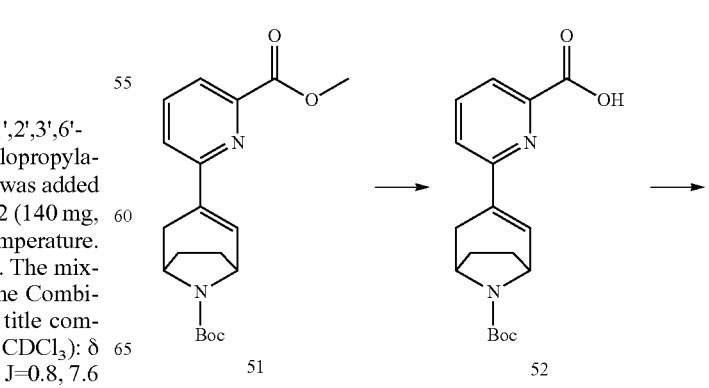
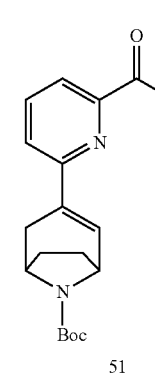
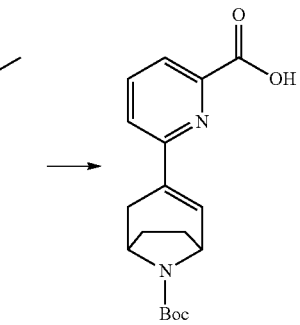

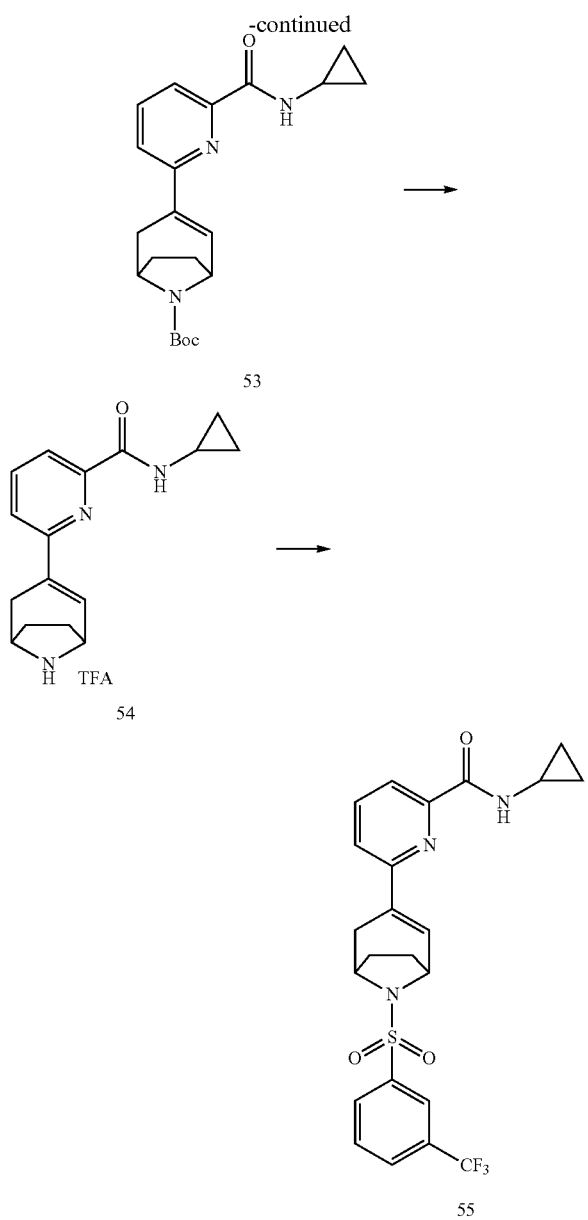

diluted with EtOAc (100 ml) and washed with brine. The aqueous phase was further extracted with EtOAc (2×100 ml) and the combined organic phase was dried with $Na_2SO_4$, filtered and concentrated to dryness. The residue was purified on CombiFlash® with 10-20% EtOAc in hexane to obtain compound 49 (688 mg, yield 55%).

c) Compound 51 was synthesized according to the procedure described in Example 6 for preparing compound 23 starting from compound 50 (Aldrich). To the solution of compound 51 (72 mg, 0.21 mmol) in methanol (1 ml) was added aqueous NaOH (1 ml, 2N). The resulting solution was stirred for 12 hours. Methanol was removed under reduced pressure and the residue was diluted with water and acidified with aqueous HCl to pH 5 at 0° C. The suspension with white precipitate was extracted with EtOAc (3×20 ml) and the combined organic phase was dried with $Na_2SO_4$, filtered, and concentrated to dryness to give compound 52 (60 mg, yield 87%).

d) 6-[8-(3-Trifluoromethylbenzenesulfonyl)-8-aza-bicyclo[3.2.1]oct-2-en-3-yl]pyridine-2-carboxylic acid cyclopropylamide (55) was then synthesized according to the procedure described in Example 8 for preparing compound 39 starting from compound 52 in a 50% yield. $^1$H NMR (400 MHz, $CDCl_3$): δ 8.16 (s, 1H), 8.10 (d, 1H, J=8 Hz), 8.09 (dd, 1H, J=0.8, 7.6 Hz), 7.97 (bd, 1H, NH), 7.78 (t, 1H, J=8 Hz), 7.70 (d, 1H, J=7.6 Hz), 7.56 (t, 1H, J=7.6 Hz), 7.34 (dd, 1H, J=0.8, 8 Hz), 6.84 (dt, 1H, J=6, 1.6 Hz), 4.60 (m, 2H), 2.92 (m, 2H), 2.45 (d, 1H, J=16 Hz), 2.18 (m, 1H), 2.01 (m, 2H), 1.72 (m, 1H), 0.92 (m, 2H), 0.68 (m, 2H); MS: 478 (M+H$^+$), 500 (M+Na).

Example 12

2-[1-(4-Trifluoromethoxybenzenesulfonyl)-1,2,3,6-tetrahydropyridin-4-yl]oxazole-4-carboxylic acid cyclopropylamide (61)

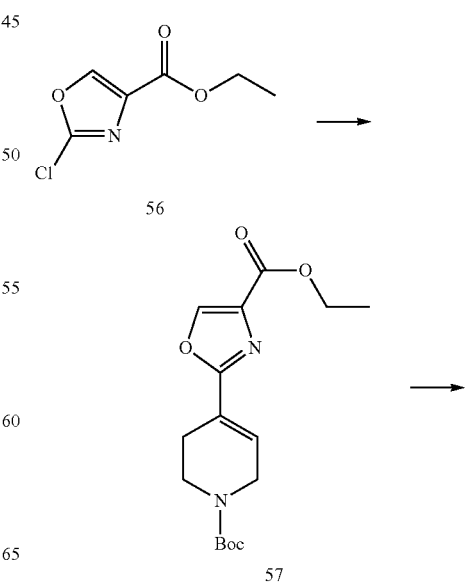

6-[8-(3-Trifluoromethylbenzenesulfonyl)-8-aza-bicyclo[3.2.1]oct-2-en-3-yl]pyridine-2-carboxylic acid cyclopropylamide (55) was prepared as follows:

a) A solution of compound 46 (1 g, 4.4 mmol, ChemImpex) in THF (5 ml) to sodium hexamethyldisilate (2.4 ml, 2M/THF, Aldrich) in 10 ml of THF at −60° C. After the addition, the mixture was allowed to warm to −20° C. and this temperature was maintained for 20 minutes. Perfluorobutanesulfonyl fluoride (1.35 g, 4.4 mmol, Aldrich) was added at −20° C. and the mixture was stirred at −20° C. for 20 minutes. The crude product was purified on silica gel column with 0-10% EtOAc in hexane to obtain compound 47 (1.9 g, yield 85%).

b) The suspension of compound 47 (1.9 g, 3.75 mmol), compound 48 (948 mg, 3.75 mmol, Carbocore), $PdCl_2$(dppf) $CH_2Cl_2$ (86 mg, 0.11 mmol, Aldrich), diphenylphosphinofferracene (61 mg, 0.11 mmol, Aldrich) and KOAc (1.03 g, 10.5 mmol) in 1,4-dioxane (15 ml) was heated at 85° C. for 1 hour. After cooling to room temperature, the reaction mixture was

Example 13

1'-[2,2,2-Trifluoro-1-(4-trifluoromethoxyphenyl)ethyl]-1',2',3',6'-tetrahydro-[2,4']bipyridinyl-6-carboxylic acid cyclopropylamide (64)

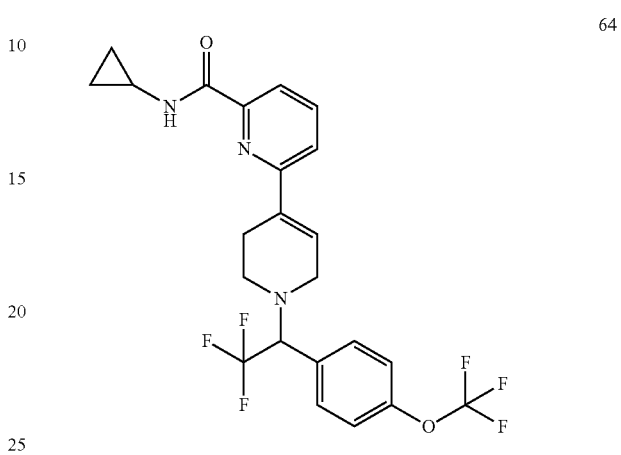

a) A solution of 1-bromo-4-(trifluoromethoxy)benzene (62) (23.4 g, 97.0 mmol, WACO) in diethyl ether (30 ml) was added dropwise over 30 minutes to a suspension of magnesium (2.60 g, 107 mmol) and catalytic amount of iodine in diethyl ether (8 ml) and the whole was stirred at room temperature for 1 hour. Trifluoroacetic anhydride (TFAA) (17.8 ml, 126 mmol) was added dropwise to the reaction mixture at 0° C. and stirred at room temperature for 1 hour. The reaction was quenched with aqueous HCl solution, extracted with ethyl acetate, washed with NaHCO$_3$ solution, dried over Na$_2$SO$_4$, filtered and concentrated in vacuo. The residue was purified by column chromatography (ethyl acetate/hexane: 1/99 to 20/80) to give 2,2,2-trifluoro-1-(4-trifluoromethoxyphenyl)ethanone (63) (599 mg, yield 2%) as colorless oil.

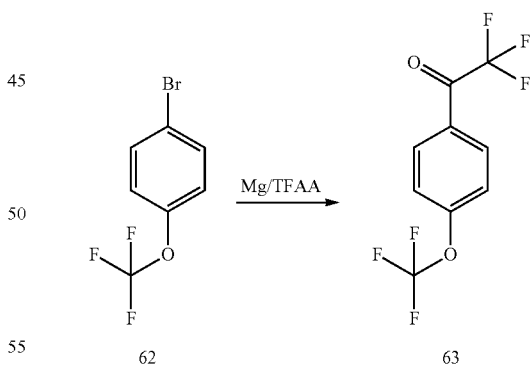

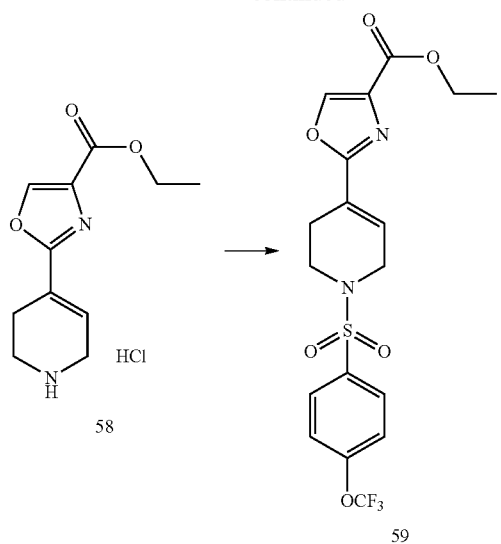

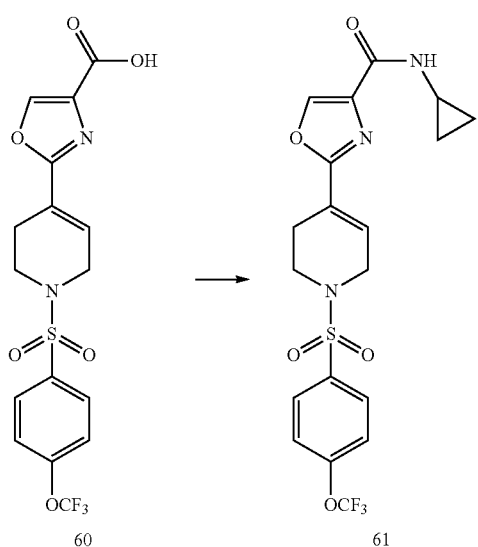

2-[1-(4-Trifluoromethoxybenzenesulfonyl)-1,2,3,6-tetrahydropyridin-4-yl]oxazole-4-carboxylic acid cyclopropylamide (61) was synthesized according to the procedure described for preparing compound 21 in Example 5 starting with compound 56 (Synchen). $^1$H NMR (400 MHz, CDCl$_3$): δ 8.03 (s, 1H), 7.80 (m, 2H), 7.30 (m, 2H), 6.85 (s, 1H), 6.58 (m, 1H), 3.79 (m, 2H), 3.28 (t, 2H, J=5.6 Hz), 2.78 (m, 1H), 2.62 (m, 2H), 0.79 (m, 2H), 0.57 (m, 2H); MS: 458 (M+H$^+$), 480 (M+Na).

b) Titanium (IV) chloride (0.098 ml, 0.887 mmol) was added to a solution of N-cyclopropyl-6-(1,2,3,6-tetrahydropyridin-4-yl)picolinamide free base (5b) (432 mg, 1.77 mmol), 2,2,2-trifluoro-1-(4-trifluoromethoxyphenyl)ethanone (63) (458 mg, 1.77 mmol) and triethylamine (0.492 ml, 3.55 mmol) in CH$_2$Cl$_2$ (12 ml) and stirred at room temperature for 18 hours. Sodium cyanoborohydride (334 mg, 5.32 mmol) in methanol (4 ml) was added to the reaction mixture and stirred for 19 hours. The reaction was quenched with aqueous NaOH solution (2 N), extracted with CH$_2$Cl$_2$, dried over Na$_2$SO$_4$, filtered and concentrated in vacuo. The residue was purified by column chromatography (ethyl acetate/hexane: 67/33) to give 1'-[2,2,2-trifluoro-1-(4-trifluoromethoxyphenyl)ethyl]-1',2',3',6'-tetrahydro-[2,4']bipyridinyl-6-carboxylic acid cyclopropylamide (64) (226 mg, yield 26%) as a pale orange oil. $^1$H NMR (400 MHz, CDCl$_1$): S 8.04 (m, 1H), 8.00 (brs, 1H), 7.77 (t, J=7.8 Hz, 1H), 7.47 (m, 3H), 7.26 (m, 2H), 6.58 (m, 1H), 4.21 (q, J=7.9 Hz, 1H), 3.45 (m, 2H), 2.97 (m, 1H), 2.90 (m, 1H), 2.80 (m, 1H), 2.66 (m, 2H), 0.88 (m, 2H), 0.65 (m, 2H); MS: 486 (M+H$^+$).

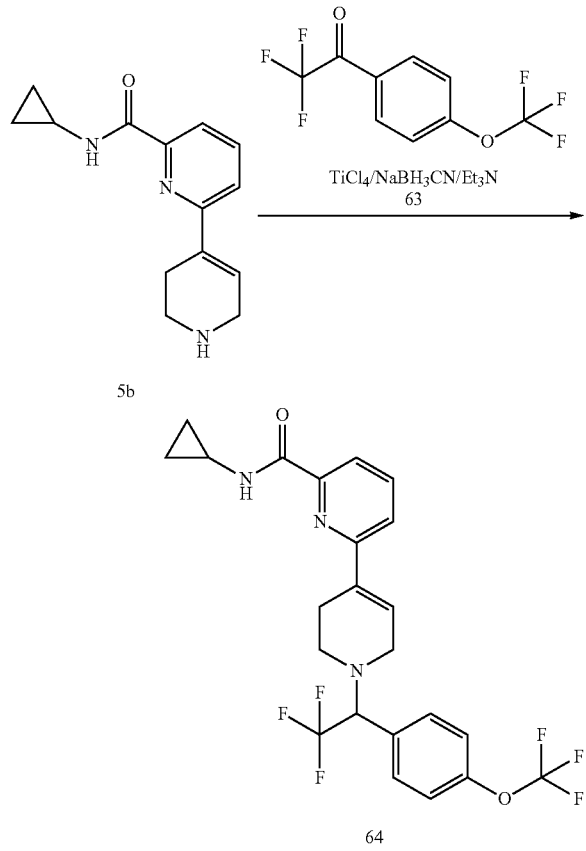

Example 14

1'-[2-Hydroxy-1-(4-trifluoromethoxyphenyl)ethyl]-1',2',3',6'-tetrahydro-[2,4']bipyridinyl-6-carboxylic acid cyclopropylamide (67)

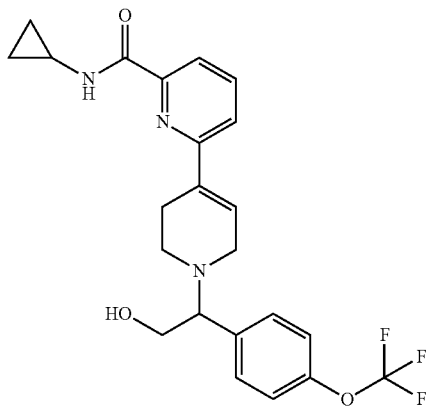

a) Sulfuric acid (0.484 ml, 9.08 mmol) was added dropwise to a solution of 2-(4-(trifluoromethoxy)phenyl)acetic acid (2.0 g, 9.08 mmol) in ethanol (20 ml), and heated under reflux for 5 hours. The reaction mixture was concentrated in vacuo, diluted with ethyl acetate (100 ml), washed with saturated NaHCO$_3$ solution and brine, dried over MgSO$_4$, filtered and concentrated in vacuo. The residue was purified by column chromatography (ethyl acetate/hexane: 0/100 to 20/80) to give ethyl 2-(4-(trifluoromethoxy)phenyl)acetate (2.06 g, yield 91%) as yellow oil.

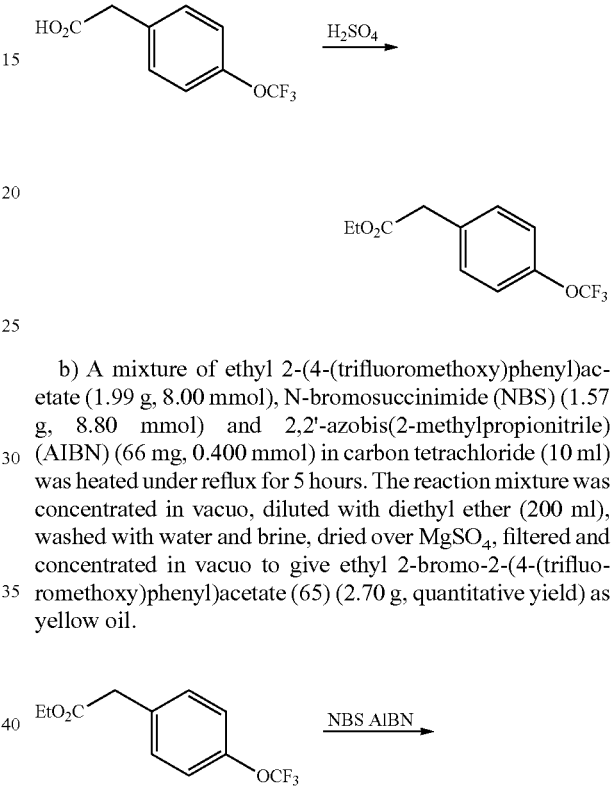

b) A mixture of ethyl 2-(4-(trifluoromethoxy)phenyl)acetate (1.99 g, 8.00 mmol), N-bromosuccinimide (NBS) (1.57 g, 8.80 mmol) and 2,2'-azobis(2-methylpropionitrile) (AIBN) (66 mg, 0.400 mmol) in carbon tetrachloride (10 ml) was heated under reflux for 5 hours. The reaction mixture was concentrated in vacuo, diluted with diethyl ether (200 ml), washed with water and brine, dried over MgSO$_4$, filtered and concentrated in vacuo to give ethyl 2-bromo-2-(4-(trifluoromethoxy)phenyl)acetate (65) (2.70 g, quantitative yield) as yellow oil.

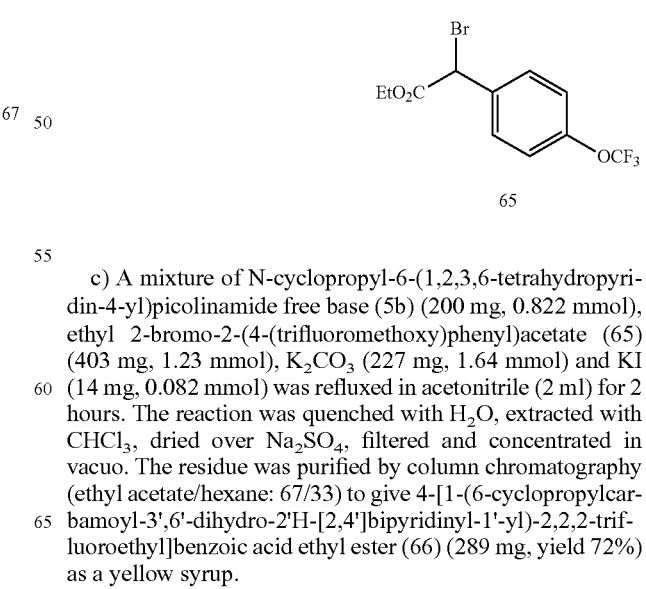

c) A mixture of N-cyclopropyl-6-(1,2,3,6-tetrahydropyridin-4-yl)picolinamide free base (5b) (200 mg, 0.822 mmol), ethyl 2-bromo-2-(4-(trifluoromethoxy)phenyl)acetate (65) (403 mg, 1.23 mmol), K$_2$CO$_3$ (227 mg, 1.64 mmol) and KI (14 mg, 0.082 mmol) was refluxed in acetonitrile (2 ml) for 2 hours. The reaction was quenched with H$_2$O, extracted with CHCl$_3$, dried over Na$_2$SO$_4$, filtered and concentrated in vacuo. The residue was purified by column chromatography (ethyl acetate/hexane: 67/33) to give 4-[1-(6-cyclopropylcarbamoyl-3',6'-dihydro-2'H-[2,4']bipyridinyl-1'-yl)-2,2,2-trifluoroethyl]benzoic acid ethyl ester (66) (289 mg, yield 72%) as a yellow syrup.

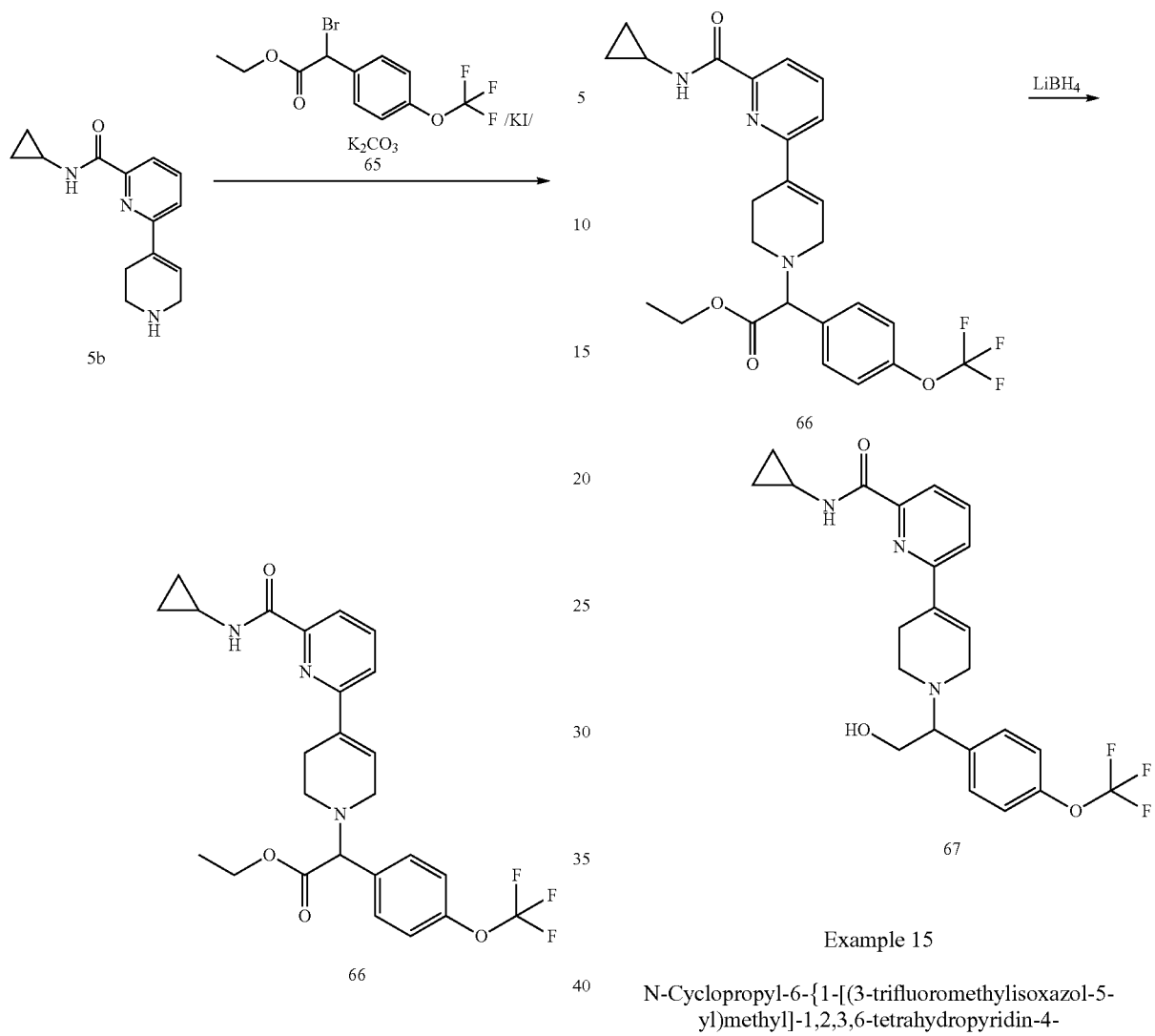

d) Lithium borohydride (34 mg, 1.6 mmol) was added to a solution of 4-[1-(6-cyclopropylcarbamoyl-3',6'-dihydro-2'H-[2,4']bipyridinyl-1'-yl)-2,2,2-trifluoro-ethyl]benzoic acid ethyl ester (66) (282 mg, 0.576 mmol) in tetrahydrofuran/ethanol (3:1, 4 ml) at room temperature and stirred for 20 hours. The reaction was quenched with $H_2O$, extracted with ethyl acetate, dried over $Na_2SO_4$, filtered and concentrated in vacuo. The residue was purified by column chromatography (methanol/$CHCl_3$: 10/90) to give 1'-[2,2,2-trifluoro-1-(4-hydroxymethylphenyl)ethyl]-1',2',3',6'-tetrahydro-[2,4']bipyridinyl-6-carboxylic acid cyclopropylamide (67) (187 mg, yield 73%) as a colorless foam. $^1$H NMR (400 MHz, $CDCl_3$): δ 8.05 (dd, J=1.2, 7.8 Hz, 1H), 8.00 (brs, 1H), 7.78 (t, J=7.8 Hz, 1H), 7.49 (dd, J=1.2, 7.8 Hz, 1H), 7.34 (m, 2H), 7.23 (m, 2H), 6.60 (m, 1H), 4.02 (m, 1H), 3.80 (m, 2H), 3.31 (m, 2H), 2.92 (m, 2H), 2.68 (m, 2H), 2.60 (m, 1H), 2H), 0.88 (m, 2H), 0.65 (m, 2H); MS: 448 (M+H$^+$).

Example 15

N-Cyclopropyl-6-{1-[(3-trifluoromethylisoxazol-5-yl)methyl]-1,2,3,6-tetrahydropyridin-4-yl}picolinamide hydrochloride (76)

a) A solution of 2,2,2-trifluoroacetic acid (68) (6.0 g, 52.6 mmol) in diethyl ether (80 ml) was added dropwise over 80 minutes to a suspension of lithium aluminiumhydride (1.52 g, 40.0 mmol) in diethyl ether (100 ml) at 0° C. and stirred at room temperature for 15 hours. The reaction was quenched with methanol (3.6 ml), $H_2O$ (3.2 ml) and concentrated $H_2SO_4$ (6.4 ml) and the resulting precipitation was filtered off. The filtrate was washed with $H_2O$ and brine, dried over $MgSO_4$, filtered and concentrated in vacuo to give a crude product of 2,2,2-trifluoroethane-1,1-diol (69). This was diluted with methanol (10 ml) and ice-water (20 g), and then hydroxylamine hydrochloride (4.06 g, 58.4 mmol) and aqueous NaOH solution (50%, 8.8 g, 110 mmol) was added successively to the mixture. The reaction mixture was stirred at room temperature for 16 hours and washed with diethyl ether (50 ml). Thus obtained aqueous phase was neutralized (pH=6) with concentrated hydrochloric acid, extracted with diethyl ether (100 ml×3), washed with H$_2$O and brine, dried over MgSO$_4$, filtered and concentrated in vacuo. The residue was purified by distillation to give (E)-2,2,2-trifluoroacetaldehyde oxime (70) (4.94 g, yield 53%) as a colorless oil (bp: 75° C.).

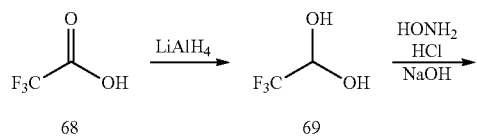

b) A solution of N-bromosuccinimide (NBS) (4.98 g, 28.0 mmol, Aldrich) in N,N-dimethylformamide (15 ml) was added dropwise over 15 minutes to a solution of (E)-2,2,2-trifluoroacetaldehyde oxime (70) (4.93 g, 28.0 mmol) in N,N-dimethylformamide (6 ml) and the whole was stirred for 16 hours. The reaction mixture was poured into ice-water (60 g), extracted with diethyl ether (60 ml×3), washed with H$_2$O and brine, dried over MgSO$_4$, filtered and concentrated in vacuo. The residue was purified by distillation to give (Z)-2,2,2-trifluoro-N-hydroxyacetimidoyl bromide (71) (5.37 g, yield 69%) as an orange oil (bp: 80-116° C.).

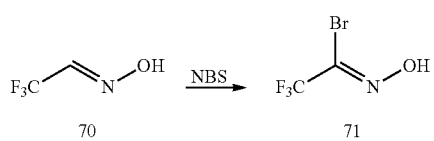

c) A solution of triethylamine (5.35 ml, 38.6 mmol) in toluene (15 ml) was added dropwise over 10 minutes to a solution of (Z)-2,2,2-trifluoro-N-hydroxyacetimidoyl bromide (71) (5.35 g, 19.3 mmol) and prop-2-yn-1-ol (72) (3.25 g, 57.9 mmol, TCI_JP) in toluene (37.5 ml) and stirred for 10 hours at room temperature. The reaction was quenched with H$_2$O (30 ml), extracted with ethyl acetate (50 ml), washed with brine, dried over MgSO$_4$, filtered and concentrated in vacuo to give a crude product of (3-(trifluoromethyl)isoxazol-5-yl)methanol (73) (1.88 g, yield 47%) as a brown oil.

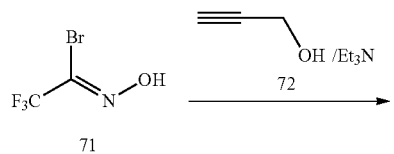

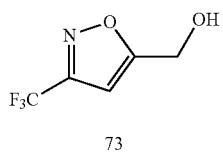

d) 2-Iodoxybenzoic acid (74) (804 mg, 2.87 mmol, Aldrich) was added to a solution of (3-(trifluoromethyl)isoxazol-5-yl)methanol (73) (300 mg, 1.44 mmol) in ethyl acetate (3 ml) at room temperature and stirred at 80° C. for 4 hours. After cooling to 0° C., insoluble materials were filtered off and the filtrate was concentrated in vacuo to give a crude product of 3-(trifluoromethyl)isoxazole-5-carbaldehyde (75) (270 mg, 57) as a pale-yellow solid.

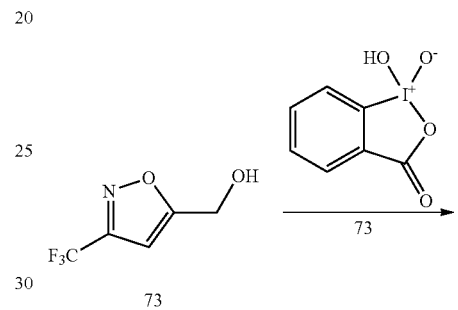

e) A mixture of N-cyclopropyl-6-(1,2,3,6-tetrahydropyridin-4-yl)picolinamide free base (5b) (133 mg, 0.545 mmol), 3-(trifluoromethyl)isoxazole-5-carbaldehyde (75) (270 mg, 0.818 mmol) and acetic acid (0.037 ml, 0.654 mmol) in tetrahydrofuran (5 ml) was stirred at room temperature for 1 hour. Sodium triacetoxyborohydride (347 mg, 1.636 mmol) was added to the reaction mixture and stirred at room temperature for 15 hours. The reaction was quenched with saturated NaHCO$_3$ solution (10 ml), extracted with ethyl acetate (50 ml×3), washed with brine, dried over MgSO$_4$, filtered and concentrated in vacuo. The residue was purified by column chromatography (ethyl acetate/hexane: 75/25 to 85/15) to give the desired free base. This was diluted with ethyl acetate and HCl solution (4 N in 1,4-dioxane) was added to the solution. The resulted solid was triturated with hexane to give N-cyclopropyl-6-(1-((3-(trifluoromethyl)isoxazol-5-yl)methyl)-1,2,3,6-tetrahydropyridin-4-yl)picolinamide hydrochloride (76) (33 mg, yield 14%) as a pale yellow solid. $^1$H NMR (DMSO-d$_6$): δ 8.52 (brs, 1H), 8.00 (m, 1H), 7.92 (m, 1H), 7.77 (m, 1H), 7.47 (m, 1H), 6.93 (s, 1H), 4.77 (m, 2H), 3.93 (m, 2H), 2.83-3.20 (m, 5H), 0.72 (m, 2H), 0.64 (m, 2H); MS: 393 (M+H$^+$).

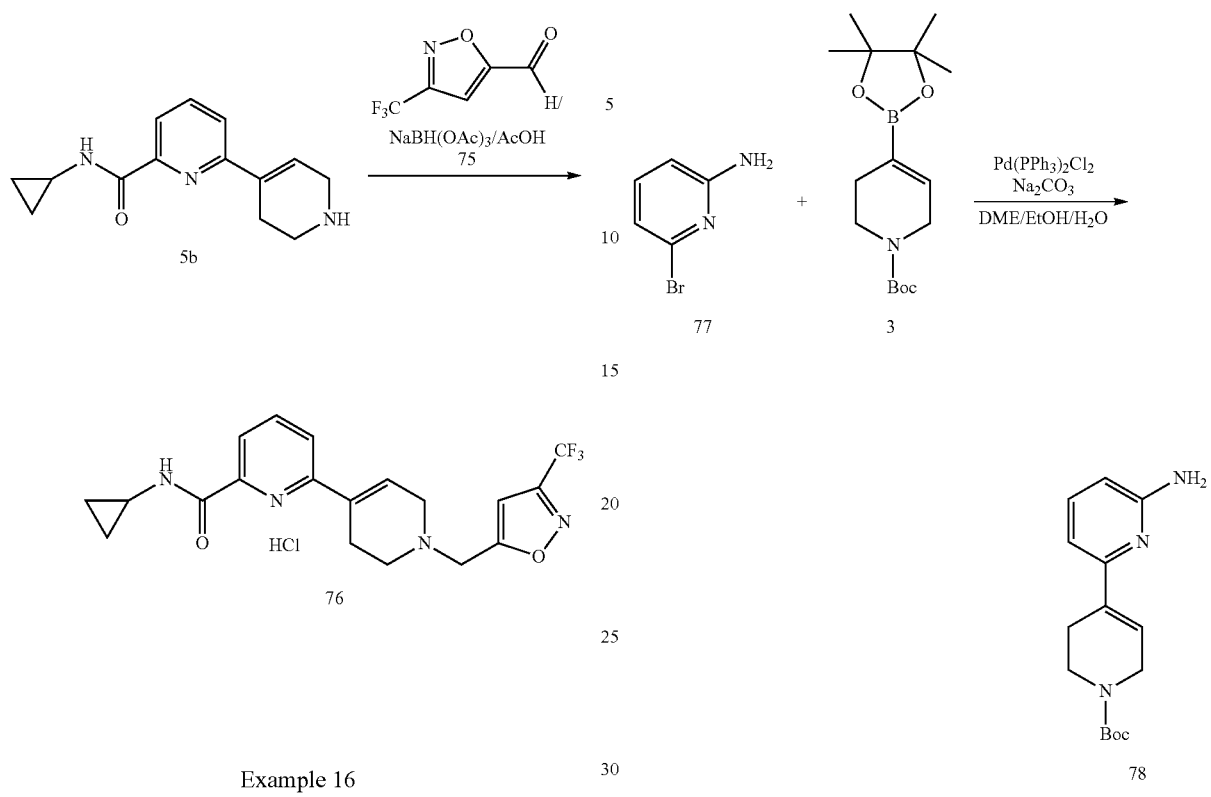

Example 16

1'-(3-Trifluoromethylbenzenesulfonyl)-1',2',3',6'-tetrahydro[2,4']bipyridinyl-6-cyclopropanoylamine (82)

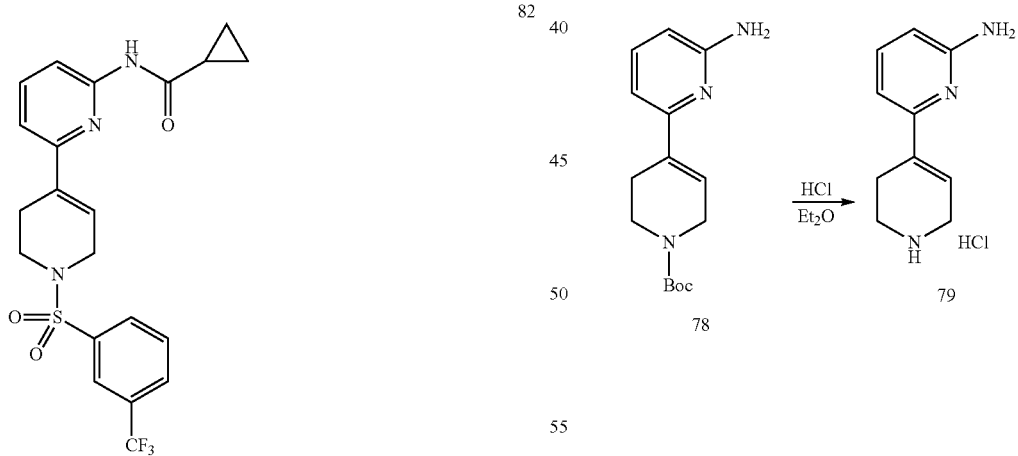

a) Compound 77 (2.5 g, 10.3 mmol, Aldrich), compound 3 (3.8 g, 12.4 mmol), Na$_2$CO$_3$ (2.12 g, 20.6 mmol) and Pd(PPh$_3$)$_2$Cl$_2$ (362 mg, 0.5 mmol) were dissolved in a mixture of DME (10 ml), EtOH (5 ml) and H$_2$O (10 ml) in a round bottom flask. The mixture was stirred at 95° C. for 2 hours, cooled to room temperature and worked-up with EtOAc, which was separated, dried and evaporated under rotary evaporator. The residue was subjected to flash column (hexanes/EtOAc) to give compound 78 (2.6 g, yield 70%).

b) Compound 78 was dissolved in about 5 ml of DCM, and then about 20 ml of 2N HCl in Et$_2$O was added. The resulting mixture was stirred at room temperature overnight. The precipitated compound 79 was filtered under vacuum and dried to give compound 79 quantitatively.

c) At −20° C., benzenesulfonyl chloride (6) (0.65 ml, 4.06 mmol) in DCM (5 ml) was added to a DCM suspension of compound 79 (1.0 g, 4.06 mmol) and TEA (2.2 ml, 16 mmol) dropwise. After the addition was complete, the mixture was slowly allowed to warm to room temperature over 2 hours, and then washed with water. The DCM layer was separated and dried over MgSO$_4$. The solvent was evaporated and the crude compound 80 was used in the next step without further purification.

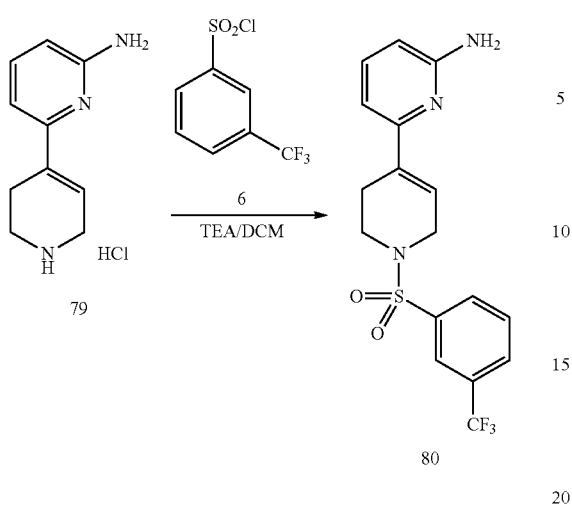

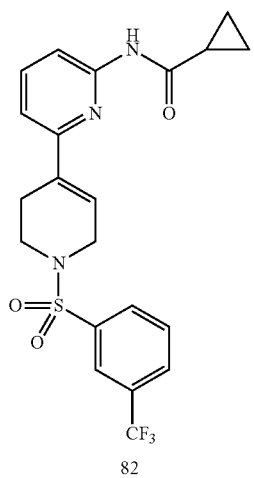

d) At 0° C., compound 81 (0.1 ml, 0.55 mmol) was added to a DCM (5 ml) solution of compound 80 (191 mg, 0.5 mmol) and TEA (0.1 ml) dropwise. After the addition was complete, the reaction mixture was slowly warmed up to room temperature overnight. The mixture was directly loaded on a silica gel column (Flash chromatography; hexanes/EtOAc) to give the title compound 82 as a white solid (160 mg, yield 71%). $^1$H NMR (400 MHz, CD$_3$OD): δ 8.02 (d, 1H, J=7.2 Hz), 8.00 (s, 1H), 7.89 (d, 1H, J=8 Hz), 7.81 (d, 1H, J=8.4 Hz), 7.74 (t, 1H, J=7.6 Hz), 7.56 (t, 1H, J=7.6 Hz), 7.07 (d, 1H, J=7.6 Hz), 6.53 (m, 2H), 3.77 (m, 2H), 3.29 (t, 2H, J=6 Hz), 2.60 (m, 2H), 1.78 (m, 1H), 0.86 (m, 2H), 0.76 (m, 2H); MS: 452 (M+H$^+$).

Example 17

1'-[(3-Trifluoromethylbenzene)aminosulfonyl]-1',2',3',6'-tetrahydro-[2,4']bipyridinyl-6-carboxylic acid cyclopropylamide (86)

a) To a suspension of compound 5 in acetonitrile (5 ml) were added TEA and compound 82 (Aldrich). After the mixture was stirred at room temperature overnight, it was diluted with EtOAc, which was washed with water. The organic layer was isolated, dried and evaporated. The residue was subjected to flash column to give compound 83 as a white foam (0.23 g, yield 70%).

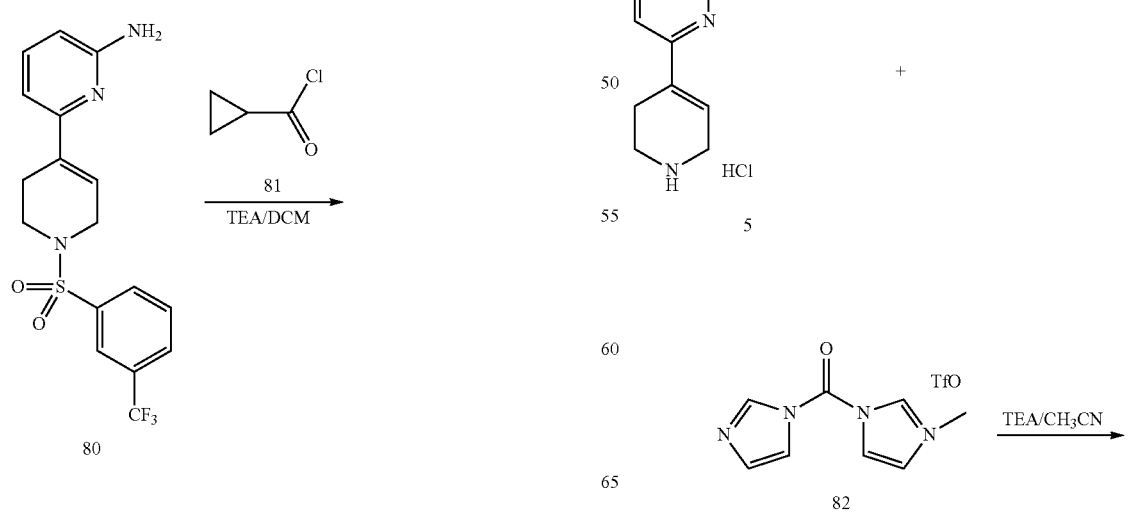

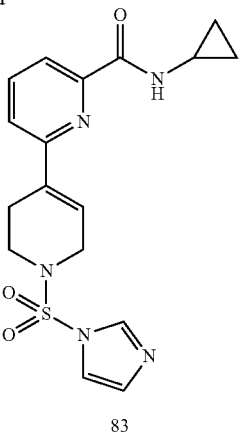

83 b) CF₃SO₃Me (0.07 ml, 0.62 mmol) was added to a DCM solution of compound 83 (0.23 g, 0.6 mmol) at 0° C. and the resulting mixture was allowed to warm up to room temperature overnight. The precipitate was collected by vacuum filtration to give compound 84 as a white solid (200 mg, 85%).

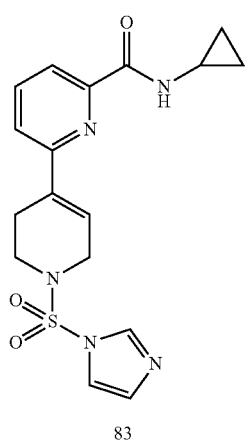 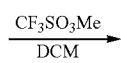

83

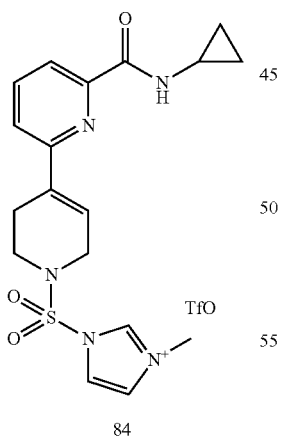

84 c) Compound 84 (100 mg, 0.18 mmol) and a corresponding aniline 85 (32 mg, 0.2 mmol) were mixed with acetonitrile, and TEA (0.2 ml) was added to the mixture subsequently. The reaction mixture was stirred at room temperature for 14 hours and then the solvent was removed by rotary evaporator. The residue was subjected to flash column to give the title compound 86 as a white foam (60 mg, yield 71%). ¹H NMR (CD₃OD): δ 7.30-8.1 (m, 7H), 6.85 (s, 1H), 4.05 (s, 2H), 3.54 (m, 2H), 2.90 (m, 1H), 2.65 (m, 2H), 0.60-0.80 (m, 4H); MS: 467 (M+H⁺).

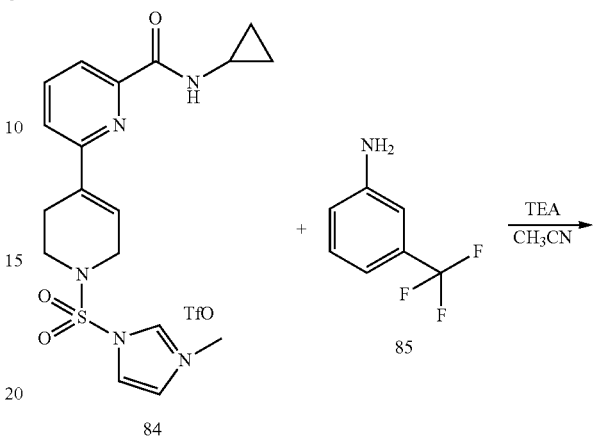

84

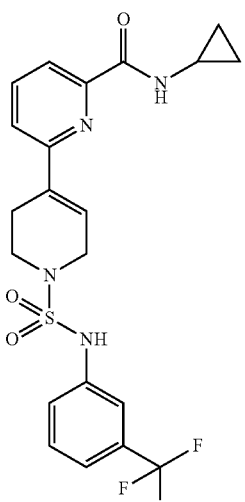

86

Example 18

Compounds of the invention have been tested in the calcium mobilization and/or electrophysiological assay for N-type calcium channel blocking activity, which are described in detail above. Representative values are presented in TABLE 2.

TABLE 2

Evaluation of the tested compounds as N-type calcium channel (NTCC) blockers after a calcium mobilization in vitro assay

| COMPOUND | NTCC IC$_{50}$ (μM) |
|---|---|
| 1'-(3-Trifluoromethylbenzenesulfonyl)-1',2',3',6'-tetrahydro-[2,4']bipyridinyl-6-carboxylic acid cyclopropylamide (7) | 0.03 |
| 1'-(4-Trifluoromethoxybenzenesulfonyl)-1',2',3',6'-tetrahydro-[2,4']bipyridinyl-6-carboxylic acid cyclopropylamide | 0.29 |

TABLE 2-continued

Evaluation of the tested compounds as N-type calcium channel (NTCC) blockers after a calcium mobilization in vitro assay

| COMPOUND | NTCC IC$_{50}$ (μM) |
|---|---|
| 1'-(3-Chlorobenzenesulfonyl)-1',2',3',6'-tetrahydro-[2,4']bipyridinyl-6-carboxylic acid cyclopropylamide | 0.08 |
| 1'-(2-Trifluoromethylbenzenesulfonyl)-1',2',3',6'-tetrahydro-[2,4']bipyridinyl-6-carboxylic acid cyclopropylamide | 0.08 |
| 1'-(4-Trifluoromethylbenzenesulfonyl)-1',2',3',6'-tetrahydro-[2,4']bipyridinyl-6-carboxylic acid cyclopropylamide | 0.11 |
| 1'-(4-Fluorobenzenesulfonyl)-1',2',3',6'-tetrahydro-[2,4']bipyridinyl-6-carboxylic acid cyclopropylamide | 0.35 |
| 1'-(3-Cyanobenzenesulfonyl)-1',2',3',6'-tetrahydro-[2,4']bipyridinyl-6-carboxylic acid cyclopropylamide | 0.05 |
| 1'-Dimethylsulfamoyl-1',2',3',6'-tetrahydro-[2,4']bipyridinyl-6-carboxylic acid cyclopropylamide | >20 |
| 1'-(3,3,3-Trifluoropropylsulfonyl)-1',2',3',6'-tetrahydro-[2,4']bipyridinyl-6-carboxylic acid cyclopropylamide | 3.10 |
| 1'-Cyclohexylsulfonyl-1',2',3',6'-tetrahydro-[2,4']bipyridinyl-6-carboxylic acid cyclopropylamide | 0.32 |
| 1'-(2,4-Dichlorobenzenesulfonyl)-1',2',3',6'-tetrahydro-[2,4']bipyridinyl-6-carboxylic acid cyclopropylamide | 0.19 |
| 1'-(3-Trifluoromethoxybenzenesulfonyl)-1',2',3',6'-tetrahydro-[2,4']bipyridinyl-6-carboxylic acid cyclopropylamide | 0.04 |
| 1'-(3-Cyano-4-fluorobenzenesulfonyl)-1',2',3',6'-tetrahydro-[2,4']bipyridinyl-6-carboxylic acid cyclopropylamide | 0.77 |
| 1'-(Pyridin-2-ylsulfonyl)-1',2',3',6'-tetrahydro-[2,4']bipyridinyl-6-carboxylic acid cyclopropylamide | 9.92 |
| 1'-(Pyridin-3-ylsulfonyl)-1',2',3',6'-tetrahydro-[2,4']bipyridinyl-6-carboxylic acid cyclopropylamide | 6.18 |
| 1'-(3-Trifluoromethylbenzylsulfonyl)-1',2',3',6'-tetrahydro-[2,4']bipyridinyl-6-carboxylic acid cyclopropylamide | 0.67 |
| 1'-(3,5-Dichlorobenzenesulfonyl)-1',2',3',6'-tetrahydro-[2,4']bipyridinyl-6-carboxylic acid cyclopropylamide | 0.05 |
| 1'-(2,4,6-Trifluorobenzenesulfonyl)-1',2',3',6'-tetrahydro-[2,4']bipyridinyl-6-carboxylic acid cyclopropylamide | 0.99 |
| 1'-(2-Methylprop-1-ylsulfonyl)-1',2',3',6'-tetrahydro-[2,4']bipyridinyl-6-carboxylic acid cyclopropylamide | 1.46 |
| 1'-Cyclopentylsulfonyl-1',2',3',6'-tetrahydro-[2,4']bipyridinyl-6-carboxylic acid cyclopropylamide | 2.70 |
| 1'-(Thiophen-3-ylsulfonyl)-1',2',3',6'-tetrahydro-[2,4']bipyridinyl-6-carboxylic acid cyclopropylamide | 1.05 |
| 1'-(4-Trifluoromethoxybenzyl)-1',2',3',6'-tetrahydro-[2,4']bipyridinyl-6-carboxylic acid cyclopropylamide (9) | 0.93 |
| 2-[1-(4-Trifluoromethoxybenzenesulfonyl)-1,2,3,6-tetrahydropyridin-4-yl]-pyrimidine-4-carboxylic acid amide (15) | >20 |
| 2-[1-(3-Trifluoromethylbenzenesulfonyl)-1,2,3,6-tetrahydropyridin-4-yl]-pyrimidine-4-carboxylic acid amide | 0.36 |
| 1'-(3-Trifluoromethylbenzenesulfonyl)-1',2',3',6'-tetrahydro-[3,4']bipyridinyl-2-carboxylic acid methyl ester | >20 |
| 1'-(3-Trifluoromethylbenzenesulfonyl)-1',2',3',6'-tetrahydro-[3,4']bipyridinyl-2-carboxylic acid cyclopropylmethylamide | 0.14 |
| 1'-(3-Trifluoromethylbenzenesulfonyl)-1',2',3',6'-tetrahydro-[3,4']bipyridinyl-2-carboxylic acid 2,2,2-trifluoroethylamide | 0.66 |
| 1'-(3-Trifluoromethylbenzenesulfonyl)-1',2',3',6'-tetrahydro-[3,4']bipyridinyl-2-carboxylic acid 3,3,3-trifluoropropylamide | 0.42 |
| 1'-(4-Trifluoromethoxybenzenesulfonyl)-1',2',3',6'-tetrahydro-[3,4']bipyridinyl-2-carboxylic acid 2,2,2-trifluoroethylamide | 0.96 |
| 1'-(4-Trifluoromethoxybenzenesulfonyl)-1',2',3',6'-tetrahydro-[3,4']bipyridinyl-2-carboxylic acid 3,3,3-trifluoropropylamide | 0.94 |
| 1'-(4-Trifluoromethoxybenzenesulfonyl)-1',2',3',6'-tetrahydro-[3,4']bipyridinyl-2-carboxylic acid cyclopropylmethylamide | 0.69 |
| 1'-(3-Trifluoromethylbenzenesulfonyl)-1',2',3',6'-tetrahydro-[2,4']bipyridinyl-6-carboxylic acid cyclopropylmethylamide (27) | 0.01 |
| 1'-(3-Trifluoromethylbenzenesulfonyl)-1',2',3',6'-tetrahydro-[2,4']-bipyridinyl-6-carboxylic acid 2,2,2-trifluoroethylamide | 0.03 |
| 1'-(3-Trifluoromethylbenzenesulfonyl)-1',2',3',6'-tetrahydro-[2,4']-bipyridinyl-6-carboxylic acid 3,3,3-trifluoropropylamide | 0.05 |
| 1'-(4-Trifluoromethoxybenzenesulfonyl)-1',2',3',6'-tetrahydro-[2,4']-bipyridinyl-6-carboxylic acid 2,2,2-trifluoroethylamide | 0.43 |
| 1'-(4-Trifluoromethoxybenzenesulfonyl)-1',2',3',6'-tetrahydro-[2,4']-bipyridinyl-6-carboxylic acid 3,3,3-trifluoropropylamide | 0.25 |
| 1'-(4-Trifluoromethoxybenzenesulfonyl)-1',2',3',6'-tetrahydro-[2,4']-bipyridinyl-6-carboxylic acid 4-fluorophenylamide | 1.92 |
| 1'-(3-Trifluoromethylbenzenesulfonyl)-1',2',3',6'-tetrahydro-[2,4']bipyridinyl-6-carboxylic acid amide (28) | 0.59 |
| 1'-(3-Trifluoromethylbenzenesulfonyl)-1',2',3',6'-tetrahydro-[2,4']bipyridinyl-6-carboxylic acid 2-hydroxyethylamide | 0.07 |
| 1'-(3-Trifluoromethylbenzenesulfonyl)-1',2',3',6'-tetrahydro-[2,4']bipyridinyl-6-carboxylic acid 1,3-dihydroxyprop-2-ylamide | 0.09 |
| 1'-(3-Trifluoromethylbenzenesulfonyl)-1',2',3',6'-tetrahydro-[2,4']bipyridinyl-6-carbonitrile (32) | 1.60 |
| N-Cyclopropylmethyl-1'-(4-trifluoromethoxybenzenesulfonyl)-1',2',3',6'-tetrahydro-[2,4']bipyridinyl-6-carboxamidine (34) | 0.32 |
| 2-[1-(3-Trifluoromethylbenzenesulfonyl)-1,2,3,6-tetrahydropyridin-4-yl]pyrimidine-4-carboxylic acid cyclopropylamide (39) | 0.06 |
| 2-[1-(3-Trifluoromethylbenzenesulfonyl)-1,2,3,6-tetrahydropyridin-4-yl]pyrimidine-4-carboxylic acid cyclopropylmethylamide | 0.13 |
| 2-[1-(4-Trifluoromethoxybenzenesulfonyl)-1,2,3,6-tetrahydropyridin-4-yl]pyrimidine-4-carboxylic acid cyclopropylamide | 0.24 |
| 5-Chloro-1'-(3-trifluoromethylbenzenesulfonyl)-1',2',3',6'-tetrahydro-[2,4']bipyridinyl-6-carboxylic acid cyclopropylamide (44) | 0.06 |
| 5-Chloro-1'-(4-trifluoromethoxybenzenesulfonyl)-1',2',3',6'-tetrahydro-[2,4']bipyridinyl-6-carboxylic acid cyclopropylamide | 0.49 |
| 6'-Oxo-1'-(3-trifluoromethylbenzenesulfonyl)-1',2',3',6'-tetrahydro-[2,4']bipyridinyl-6-carboxylic acid cyclopropylamide (45) | 0.02 |
| 6-[8-(3-Trifluoromethylbenzenesulfonyl)-8-azabicyclo[3.2.1]oct-2-en-3-yl]pyridine-2-carboxylic acid cyclopropylamide (55) | 0.05 |
| 2-[1-(4-Trifluoromethoxybenzenesulfonyl)-1,2,3,6-tetrahydropyridin-4-yl]oxazole-4-carboxylic acid cyclopropylamide (61) | 0.32 |

TABLE 2-continued

Evaluation of the tested compounds as N-type calcium channel (NTCC) blockers after a calcium mobilization in vitro assay

| COMPOUND | NTCC IC$_{50}$ (µM) |
|---|---|
| 1'-[2,2,2-Trifluoro-1-(4-trifluoromethoxyphenyl)-ethyl]-1',2',3',6'-tetrahydro-[2,4']bipyridinyl-6-carboxylic acid cyclopropylamide (64) | 0.32 |
| 1'-[2,2,2-Trifluoro-1-(4-hydroxymethylphenyl)-ethyl]-1',2',3',6'-tetrahydro-[2,4']bipyridinyl-6-carboxylic acid cyclopropylamide (67) | 1.34 |
| N-Cyclopropyl-6-{1-[(3-trifluoromethylisoxazol-5-yl)methyl]-1,2,3,6-tetrahydropyridin-4-yl}picolinamide hydrochloride (76) | 2.76 |
| 1'-(3-Trifluoromethylbenzenesulfonyl)-1',2',3',6'-tetrahydro-[2,4']bipyridinyl-6-carboxylic acid methyl ester (25) | 0.92 |
| 1'-(3-Trifluoromethylbenzenesulfonyl)-1',2',3',6'-tetrahydro-[2,4']bipyridinyl-6-carboxylic acid (26) | >20 |
| 1'-(3-Trifluoromethylbenzenesulfonyl)-1',2',3',6'--tetrahydro-[2,4']bipyridinyl-6-yl]methanol | 4.24 |
| 1'-(3-Trifluoromethylbenzenesulfonyl)-1',2',3',6'-tetrahydro[2,4']bipyridinyl-6-cyclopropanoylamine (82) | 0.30 |
| 1'-[(3-Trifluoromethylbenzene)aminosulfonyl]-1',2',3',6'-tetrahydro-[2,4']bipyridinyl-6-carboxylic acid cyclopropylamide (86) | 1.05 |

Compounds 1'-(4-trifluoromethoxybenzyl)-1',2',3',6'-tetrahydro-[2,4']-bi-pyridinyl-6-carboxylic acid cyclopropylamide (9) and 6'-oxo-1'-(3-trifluoromethyl-benzenesulfonyl)-1',2',3',6'-tetrahydro-[2,4']bipyridinyl-6-carboxylic acid cyclopropyl-amide (45) have also been tested in the calcium mobilization assay for L-type calcium channel blocking activity, which is described in detail above, and have an LTCC IC$_{50}$ value of >20 µM in that assay.

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

---

What is claimed is:

1. A compound having the Formula I:

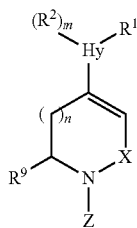

I or a pharmaceutically acceptable salt thereof, wherein:

Hy is a 6-membered heteroaromatic ring, a 5-membered heteroaromatic ring, or a 5-membered heterocyclic ring, wherein said Hy has at least one nitrogen atom, and wherein said Hy is attached to the tetrahydropyridinyl or dihydropyrrolyl ring by a carbon atom;

$R^1$ is attached to a carbon atom of said Hy ring and is selected from the group consisting of
- a) —C(=W)$NR^3R^4$;
- b) —C(=O)$OR^5$;
- c) —$NR^6$—C(=O)$R^7$;
- d) cyano;
- e) hydroxyalkyl; and
- f) a 5-membered, N-containing heteroaryl or a 5-membered, partially unsaturated, N-containing heterocyclo each of which is optionally substituted with one or two substituents each independently selected from the group consisting of alkyl, alkoxy, halogen, haloalkyl, haloalkoxy, hydroxy, hydroxyalkyl, cyano, amino, aminoalkyl, alkylamino, and dialkylamino; wherein W is O or $NR^{14}$, wherein $R^{14}$ is hydrogen or alkyl;

$R^3$, $R^4$, and $R^7$ are each independently selected from the group consisting of hydrogen, alkyl, alkenyl, alkynyl, haloalkyl, hydroxyalkyl, cycloalkyl, (cycloalkyl)alkyl, cycloalkenyl, (cycloalkenyl)alkyl, heterocyclo, heterocycloalkyl, aryl, arylalkyl, heteroaryl, and heteroarylalkyl, wherein the cycloalkyl, cycloalkenyl, heterocyclo, aryl and heteroaryl portions thereof are optionally substituted with one or more substituents each independently selected from the group consisting of alkyl, alkoxy, halogen, haloalkyl, haloalkoxy, hydroxy, hydroxyalkyl, cyano, amino, aminoalkyl, alkylamino, dialkylamino, and hydroxyalkylamino; and $R^5$ and $R^6$ are hydrogen or alkyl;

$R^2$ is selected from the group consisting of alkyl, alkenyl, alkynyl, halogen, hydroxyalkyl, hydroxy, alkoxy, alkoxyalkyl, haloalkyl, haloalkoxy, haloalkoxyalkyl, nitro, cyano, amino, alkylamino, and dialkylamino;

m is 0, 1, 2, or 3;

n is 0 or 1;

X is —$CHR^8$— or —C(=O)—;

$R^8$ and $R^9$ are both hydrogen or together form a bridge —$(CH_2)_p$—, wherein p is 2, 3, or 4;

Z is $Z^1$ or $Z^2$, wherein $Z^1$ is —$SO_2$—$R^{10}$, wherein $R^{10}$ is selected from the group consisting of $C_{3-12}$ alkyl, halo($C_{3-12}$)alkyl, $C_{5-12}$ cycloalkyl, ($C_{3-12}$ cycloalkyl)alkyl, $C_{5-12}$ cycloalkenyl, ($C_{3-12}$ cycloalkenyl)alkyl, heterocyclo, heterocycloalkyl, aryl, arylalkyl, heteroaryl, heteroarylalkyl, arylamino, cycloalkenyl, heterocyclo, aryl and heteroaryl portions thereof are optionally substituted with one or more substituents each independently selected from the group consisting of alkyl, alkoxy, halogen, haloalkyl, haloalkoxy, hydroxy, hydroxyalkyl, cyano, amino, aminoalkyl, alkylamino, dialkylamino, and hydroxyalkylamino; and $Z^2$ is —C($R^{11}R^{12}$)$R^{13}$, wherein $R^{11}$ and $R^{12}$ are each independently selected from the group consisting of hydrogen, alkyl, haloalkyl, hydroxyalkyl, halogen, hydroxy, alkoxy, alkoxyalkyl, haloalkoxy, haloalkoxyalkyl, cyano, amino, aminoalkyl, alkylaminoalkyl, and dialkylaminoalkyl; and $R^{13}$ is selected from the group consisting of aryl, arylalkyl, heteroaryl, and heteroarylalkyl, wherein the aryl and heteroaryl portions thereof are optionally substituted with one or more substituents each independently selected from the group consisting of alkyl, alkoxy, halogen, haloalkyl, haloalkoxy, hydroxy, hydroxyalkyl, cyano, amino, aminoalkyl, alkylamino, dialkylamino, and hydroxyalkylamino;

with the following provisos when X is —$CHR^8$— and $R^8$ is hydrogen:

1) when $R^{11}$ and $R^{12}$ are both hydrogen and $R^{13}$ is aryl or arylalkyl, then the aryl portion of $R^{13}$ is substituted with at least one of haloalkyl or haloalkoxy; or
2) when Hy is a pyridin-2-yl ring, then $R^1$ is other than optionally substituted 2-aminophenylaminocarbonyl or 2-hydroxyphenylaminocarbonyl.

2. The compound of claim 1, wherein n is 1.

3. The compound of claim 2, wherein X is —$CHR^8$— and $R^8$ and $R^9$ are both hydrogen, having the Formula II:

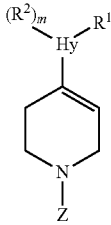

II or a pharmaceutically acceptable salt thereof, provided that when Hy is a pyridin-2-yl ring, then $R^1$ is other than optionally substituted 2-aminophenylaminocarbonyl or 2-hydroxyphenylaminocarbonyl.

4. The compound of claim 2, wherein X is —$CHR^8$—, $R^8$ and $R^9$ together form a bridge —$(CH_2)_p$—, and p is 2, 3, or 4, having the Formula III:

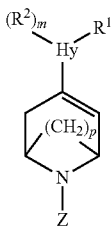

III or a pharmaceutically acceptable salt thereof.

5. The compound of claim 4, wherein p is 2, having the Formula IV:

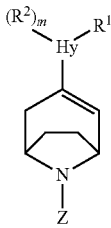

IV or a pharmaceutically acceptable salt thereof.

6. The compound of claim 2, wherein X is —C(═O)— and $R^9$ is hydrogen, having the Formula V:

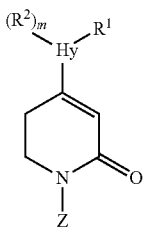

V or a pharmaceutically acceptable salt thereof.

7. The compound of claim 1, wherein n is 0.

8. The compound of claim 7, wherein X is —$CHR^8$— and $R^8$ and $R^9$ are both hydrogen, having the Formula VI:

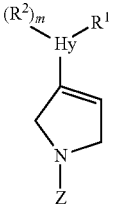

VI or a pharmaceutically acceptable salt thereof, provided that when Hy is a pyridin-2-yl ring, then $R^1$ is other than optionally substituted 2-aminophenylaminocarbonyl or 2-hydroxyphenylaminocarbonyl.

9. The compound of claim 7, wherein X is —$CHR^8$—, $R^8$ and $R^9$ together form a bridge —$(CH_2)_p$—, and p is 2, 3, or 4, having the Formula VII:

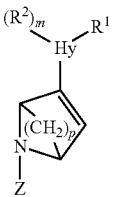

VII or a pharmaceutically acceptable salt thereof.

10. The compound of claim 9, wherein p is 2, having the Formula VIII:

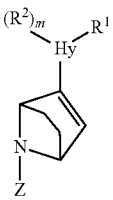

VIII or a pharmaceutically acceptable salt thereof.

11. The compound of claim 7, wherein X is —C(═O)— and $R^9$ is hydrogen, having the Formula IX:

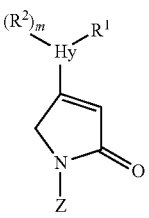

IX or a pharmaceutically acceptable salt thereof.

12. The compound of claim 1, wherein Hy is selected from the group consisting of pyridyl, pyrimidinyl, pyrazinyl, pyrrolyl, imidazolyl, triazolyl, thiazolyl, oxazolyl, isoxazolyl, and 1,2,4-oxadiazolyl.

13. The compound of claim 12, wherein Hy is selected from the group consisting of pyridin-2-yl, pyridin-3-yl, pyrimidin-2-yl, pyrimidin-4-yl, pyrazin-2-yl, imidazol-2-yl, imidazol-4-yl, and oxazol-2-yl.

14. The compound of claim 13, wherein Hy is pyridin-2-yl, pyridin-3-yl, pyrimidin-2-yl, or oxazol-2-yl.

15. The compound of claim 1, wherein $R^1$ is attached to a carbon atom adjacent to a nitrogen atom of said Hy ring.

16. The compound of claim 1, having the Formula X:

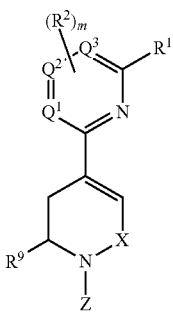

or a pharmaceutically acceptable salt thereof,
wherein one of $Q^1$, $Q^2$, or $Q^3$ is N and the remaining two are each CH; or
$Q^1$, $Q^2$, and $Q^3$ each are CH; and
X, Z, $R^1$, $R^2$, $R^9$ and m are as defined in claim 1.

17. The compound of claim 16, having the Formula XI:

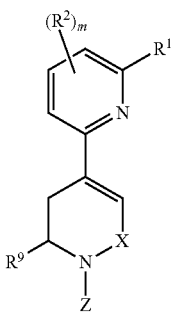

or a pharmaceutically acceptable salt thereof.

18. The compound of claim 1, having the Formula XII:

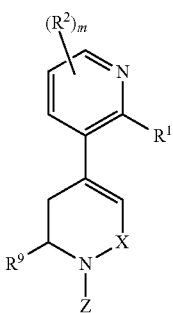

or a pharmaceutically acceptable salt thereof,
wherein X, $R^1$, $R^2$, and $R^9$ and m are as defined in claim 1.

19. The compound of claim 16, wherein X is —$CHR^8$— and $R^8$ and $R^9$ both are hydrogen.

20. The compound of claim 16, wherein X is —$CHR^8$— and $R^8$ and $R^9$ together form a bridge —$(CH_2)_p$— and p is 2, 3, or 4.

21. The compound of claim 20, wherein p is 2.

22. The compound of claim 16, wherein X is —C(=O)— and $R^9$ is hydrogen.

23. The compound of claim 1, wherein $R^1$ is —C(=W)$NR^3R^4$, wherein W is O or $NR^{14}$, $R^{14}$ is hydrogen or alkyl, and $R^3$ and $R^4$ are each independently selected from the group consisting of hydrogen, alkyl, alkenyl, alkynyl, haloalkyl, hydroxyalkyl, cycloalkyl, (cycloalkyl)alkyl, cycloalkenyl, (cycloalkenyl)alkyl, heterocyclo, heterocycloalkyl, aryl, arylalkyl, heteroaryl, and heteroarylalkyl, wherein the cycloalkyl, cycloalkenyl, heterocyclo, aryl and heteroaryl portions thereof are optionally substituted with one or more substituents each independently selected from the group consisting of alkyl, alkoxy, halogen, haloalkyl, haloalkoxy, hydroxy, hydroxyalkyl, cyano, amino, aminoalkyl, alkylamino, dialkylamino, and hydroxyalkylamino.

24. The compound of claim 23, wherein $R^{14}$ is hydrogen, $R^3$ is hydrogen or alkyl and $R^4$ is as defined in claim 23.

25. The compound of claim 24, wherein $R^3$ is hydrogen and $R^4$ is selected from the group consisting of $C_{1-6}$ alkyl, $C_{2-6}$ alkenyl, $C_{2-6}$ alkynyl, halo($C_{1-6}$)alkyl, hydroxy($C_{1-6}$)alkyl, $C_{3-7}$ cycloalkyl, $C_{3-7}$ cycloalkyl($C_{1-4}$)alkyl, $C_{3-7}$ cycloalkenyl, $C_{3-7}$ cycloalkenyl($C_{1-4}$)alkyl, 5- or 6-membered heterocyclo, 5- or 6-membered heterocyclo($C_{1-4}$)alkyl, $C_{6-10}$ aryl, $C_{6-10}$ aryl($C_{1-4}$)alkyl, 5- or 6-membered heteroaryl, and 5- or 6-membered heteroaryl($C_{1-4}$)alkyl, wherein the cycloalkyl, cycloalkenyl, heterocyclo, aryl, and heteroaryl portions thereof are optionally substituted with one or more substituents each independently selected from the group consisting of alkyl, alkoxy, halogen, haloalkyl, haloalkoxy, hydroxy, hydroxyalkyl, cyano, amino, aminoalkyl, alkylamino, dialkylamino, and hydroxyalkylamino.

26. The compound of claim 25, wherein $R^4$ is selected from the group consisting of $C_{1-6}$ alkyl, $C_{2-6}$ alkenyl, halo($C_{1-6}$)alkyl, monohydroxy($C_{1-6}$)alkyl, dihydroxy($C_{1-6}$)alkyl, $C_{3-7}$ cycloalkyl, $C_{3-7}$ cycloalkyl($C_{1-4}$)alkyl, $C_{3-7}$ cycloalkenyl, $C_{3-7}$ cycloalkenyl($C_{1-4}$)alkyl, phenyl, and benzyl, wherein said phenyl or phenyl portion of said benzyl is optionally substituted with 1, 2, or 3 substituents each independently selected from the group consisting of $C_{1-6}$ alkyl, $C_{1-6}$ alkoxy, halogen, halo($C_{1-6}$)alkyl, halo($C_{1-6}$)alkoxy, hydroxy, hydroxy($C_{1-6}$)alkyl, cyano, amino, amino($C_{1-6}$)alkyl, $C_{1-6}$ alkylamino, di($C_{1-6}$)alkylamino, and hydroxy($C_{1-6}$)alkylamino.

27. The compound of claim 23, wherein W is O.

28. The compound of claim 23, wherein $R^1$ is —C(=O)—NH-cyclopropyl, —C(=O)—$NH_2$ or —C(=O)—NH—$CH_2$-cyclopropyl.

29. The compound of claim 23, wherein W is NH.

30. The compound of claim 23, wherein $R^1$ is —C(=NH)—NH—$CH_2$-cyclopropyl.

31. The compound of claim 1, wherein $R^1$ is —C(=O)$OR^5$, wherein $R^5$ is hydrogen or alkyl.

32. The compound of claim 1, wherein $R^1$ is —$NR^6$—C(=O)$R^7$, wherein $R^6$ is hydrogen or alkyl, and $R^7$ is selected from the group consisting of hydrogen, alkyl, alkenyl, alkynyl, haloalkyl, hydroxyalkyl, cycloalkyl, (cycloalkyl)alkyl, cycloalkenyl, (cycloalkenyl)alkyl, heterocyclo, heterocycloalkyl, aryl, arylalkyl, heteroaryl, and heteroarylalkyl, wherein the cycloalkyl, cycloalkenyl, heterocyclo, aryl and heteroaryl portions thereof are optionally substituted with one or more substituents each independently selected from the group consisting of alkyl, alkoxy, halogen, haloalkyl, haloalkoxy, hydroxy, hydroxyalkyl, cyano, amino, aminoalkyl, alkylamino, dialkylamino, and hydroxyalkylamino.

33. The compound of claim 32, wherein $R^7$ is selected from the group consisting of $C_{1-6}$ alkyl, $C_{2-6}$ alkenyl, $C_{2-6}$ alkynyl, halo($C_{1-6}$)alkyl, hydroxy($C_{1-6}$)alkyl, $C_{3-7}$ cycloalkyl, $C_{3-7}$ cycloalkyl($C_{1-4}$)alkyl, $C_{3-7}$ cycloalkenyl, $C_{3-7}$ cycloalkenyl($C_{1-4}$)alkyl, 5- or 6-membered heterocyclo, 5- or 6-membered heterocyclo($C_{1-4}$)alkyl, $C_{6-10}$ aryl, $C_{6-10}$ aryl($C_{1-4}$)alkyl, 5- or 6-membered heteroaryl, and 5- or 6-membered heteroaryl($C_{1-4}$)alkyl, wherein the cycloalkyl, cycloalkenyl, heterocyclo, aryl, and heteroaryl portions thereof are optionally substituted with one or more substituents each independently selected from the group consisting of alkyl, alkoxy, halogen, haloalkyl, haloalkoxy, hydroxy, hydroxyalkyl, cyano, amino, aminoalkyl, alkylamino, dialkylamino, and hydroxyalkylamino.

34. The compound of claim 33, wherein $R^7$ is selected from the group consisting of $C_{1-6}$ alkyl, $C_{2-6}$ alkenyl, halo($C_{1-6}$)alkyl, monohydroxy($C_{1-6}$)alkyl, dihydroxy($C_{1-6}$)alkyl, $C_{3-7}$ cycloalkyl, $C_{3-7}$ cycloalkyl($C_{1-4}$)alkyl, $C_{3-7}$ cycloalkenyl, $C_{3-7}$ cycloalkenyl($C_{1-4}$)alkyl, phenyl, and benzyl, wherein said phenyl or phenyl portion of said benzyl is optionally substituted with 1, 2, or 3 substituents each independently selected from the group consisting of $C_{1-6}$ alkyl, $C_{1-6}$ alkoxy, halogen, halo($C_{1-6}$)alkyl, halo($C_{1-6}$)alkoxy, hydroxy, hydroxy($C_{1-6}$)alkyl, cyano, amino, amino($C_{1-6}$)alkyl, $C_{1-6}$ alkylamino, di($C_{1-6}$)alkylamino, and hydroxy($C_{1-6}$)alkylamino.

35. The compound of claim 32, wherein $R^1$ is —NH—C(=O)-cyclopropyl.

36. The compound of claim 1, wherein $R^1$ is cyano.

37. The compound of claim 1, wherein $R^1$ is hydroxyalkyl.

38. The compound of claim 1, wherein $R^1$ is a 5-membered, N-containing heteroaryl or a 5-membered, partially unsaturated, N-containing heterocyclo each of which is optionally substituted with one or two substituents each independently selected from the group consisting of alkyl, alkoxy, halogen, haloalkyl, haloalkoxy, hydroxy, hydroxyalkyl, cyano, amino, aminoalkyl, alkylamino, and dialkylamino.

39. The compound of claim 38, wherein $R^1$ is selected from the group consisting of oxazolyl, 1,2,4-oxadiazolyl, 1,3,4-oxadiazolyl, and thiazolyl, any of which is optionally substituted with one or two substituents each independently selected from the group consisting of alkyl, alkoxy, halogen, haloalkyl, haloalkoxy, hydroxy, hydroxyalkyl, cyano, amino, aminoalkyl, alkylamino, and dialkylamino.

40. The compound of claim 39, wherein $R^1$ is selected from the group consisting of

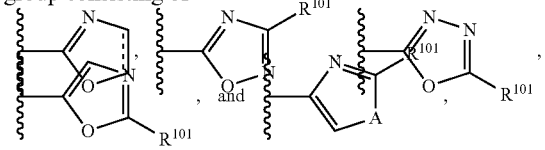

wherein
$R^{101}$ is selected from the group consisting of alkyl, alkoxy, halogen, haloalkyl, haloalkoxy, hydroxy, hydroxyalkyl, cyano, amino, aminoalkyl, alkylamino, and dialkylamino, A is O or S, and ---- is an optional bond forming a double bond.

41. The compound of claim 1, wherein $R^2$ is selected from the group consisting of $C_{1-4}$ alkyl, halo($C_{1-4}$)alkyl, halogen, hydroxy($C_{1-4}$)alkyl, hydroxy, $C_{1-4}$ alkoxy, $C_{1-4}$ alkoxy($C_{1-4}$)alkyl, halo($C_{1-4}$)alkoxy, halo($C_{1-4}$)alkoxy($C_{1-4}$)alkyl, nitro, cyano, amino, $C_{1-4}$ alkylamino, and di($C_{1-4}$)alkylamino.

42. The compound of claim 1, wherein m is 0 or 1.

43. The compound of claim 1, wherein Z is $Z^1$.

44. The compound of claim 43, wherein $R^{10}$ is $C_{4-8}$ alkyl, halo($C_{3-6}$)alkyl, $C_{5-12}$ cycloalkyl, ($C_{3-12}$ cycloalkyl)alkyl, $C_{5-12}$ cycloalkenyl, ($C_{3-12}$ cycloalkenyl)alkyl, heterocyclo, heterocycloalkyl, aryl, arylalkyl, heteroaryl, heteroarylalkyl, arylamino, and aryl(alkyl)amino, wherein the cycloalkyl, cycloalkenyl, heterocyclo, aryl and heteroaryl portions thereof are optionally substituted with one or more substituents each independently selected from the group consisting of alkyl, alkoxy, halogen, haloalkyl, haloalkoxy, hydroxy, hydroxyalkyl, cyano, amino, aminoalkyl, alkylamino, dialkylamino, and hydroxyalkylamino.

45. The compound of claim 44, wherein $R^{10}$ is selected from the group consisting of $C_{4-6}$ alkyl, monohalo($C_{3-6}$)alkyl, dihalo($C_{3-6}$)alkyl, trihalo($C_{3-6}$)alkyl, $C_{5-8}$ cycloalkyl, $C_{3-8}$ cycloalkyl($C_{1-2}$)alkyl, $C_{5-8}$ cycloalkenyl, $C_{3-8}$ cycloalkenyl($C_{1-2}$)alkyl, 5- or 6-membered heterocyclo, 5- or 6-membered heterocyclo($C_{1-2}$)alkyl, $C_{6-14}$ aryl, $C_{6-14}$ aryl($C_{1-2}$)alkyl, 5- or 6-membered heteroaryl, and 5- or 6-membered heteroaryl($C_{1-2}$)alkyl, wherein the cycloalkyl, cycloalkenyl, heterocyclo, aryl and heteroaryl portions thereof are optionally substituted with 1, 2, or 3 substituents each independently selected from the group consisting of $C_{1-4}$ alkyl, $C_{1-4}$ alkoxy, halogen, halo($C_{1-4}$)alkyl, halo($C_{1-4}$)alkoxy, hydroxy, hydroxy($C_{1-4}$)alkyl, cyano, amino, amino($C_{1-4}$)alkyl, $C_{1-4}$ alkylamino, di($C_{1-4}$)alkylamino, and hydroxy($C_{1-4}$)alkylamino.

46. The compound of claim 45, wherein $R^{10}$ is selected from the group consisting of
a) cyclohexyl;
b) cycloheptyl;
c) cyclohexylmethyl;
d) cycloheptylmethyl;
e) phenyl, unsubstituted or substituted with 1, 2 or 3 substituents each independently selected from the group consisting of $C_{1-4}$ alkyl, $C_{1-4}$ alkoxy, halogen, halo($C_{1-4}$)alkyl, halo($C_{1-4}$)alkoxy, hydroxy, hydroxy($C_{1-4}$)alkyl, cyano, amino, amino($C_{1-4}$)alkyl, $C_{1-4}$ alkylamino, di($C_{1-4}$)alkylamino, and hydroxy($C_{1-4}$)alkylamino;
f) benzyl, unsubstituted or substituted with 1, 2 or 3 substituents each independently selected from the group consisting of $C_{1-4}$ alkyl, $C_{1-4}$ alkoxy, halogen, halo($C_{1-4}$)alkyl, halo($C_{1-4}$)alkoxy, hydroxy, hydroxy($C_{1-4}$)alkyl, cyano, amino, amino($C_{1-4}$)alkyl, $C_{1-4}$ alkylamino, di($C_{1-4}$)alkylamino, and hydroxy($C_{1-4}$)alkylamino;
g) phenylethyl, unsubstituted or substituted with 1, 2 or 3 substituents each independently selected from the group consisting of $C_{1-4}$ alkyl, $C_{1-4}$ alkoxy, halogen, halo($C_{1-4}$)alkyl, halo($C_{1-4}$)alkoxy, hydroxy, hydroxy($C_{1-4}$)alkyl, cyano, amino, amino($C_{1-4}$)alkyl, $C_{1-4}$ alkylamino, di($C_{1-4}$)alkylamino, and hydroxy($C_{1-4}$)alkylamino;
h) pyridin-1-yl, pyridin-2-yl, or pyridin-3-yl, unsubstituted or substituted with 1 or 2 substituents each independently selected from the group consisting of halogen, halo($C_{1-4}$)alkyl, halo($C_{1-4}$)alkoxy, and cyano;
i) thiophen-2-yl or thiophen-3-yl, unsubstituted or substituted with 1 or 2 substituents each independently selected from the group consisting of halogen, halo($C_{1-4}$)alkyl, halo($C_{1-4}$alkoxy, and cyano;
j) isoxazol-3-yl, isoxazol-4-yl, or isoxazol-5-yl, unsubstituted or substituted with 1 or 2 substituents each independently selected from the group consisting of halogen, halo($C_{1-4}$)alkyl, halo($C_{1-4}$)alkoxy, and cyano;
k) oxazol-2-yl, oxazol-4-yl, or oxazol-5-yl, unsubstituted or substituted with 1 or 2 substituents each independently selected from the group consisting of halogen, halo($C_{1-4}$)alkyl, halo($C_{1-4}$)alkoxy, and cyano; and
l) isoxazol-3-ylmethyl, isoxazol-4-ylmethyl, or isoxazol-5-ylmethyl, unsubstituted or substituted with 1 or 2 substituents each independently selected from the group consisting of halogen, halo($C_{1-4}$)alkyl, halo($C_{1-4}$)alkoxy, and cyano.

47. The compound of claim 46, wherein $R^{10}$ is e) phenyl, unsubstituted or substituted with 1, 2, or 3 substituents each independently selected from the group consisting of $C_{1-4}$ alkyl, $C_{1-4}$ alkoxy, halogen, halo($C_{1-4}$)alkyl, halo($C_{1-4}$) alkoxy, hydroxy, hydroxy($C_{1-4}$alkyl, cyano, amino, amino($C_{1-4}$)alkyl, $C_{1-4}$ alkylamino, di($C_{1-4}$alkylamino, and hydroxy($C_{1-4}$)alkylamino.

48. The compound of claim 1, wherein Z is $Z^2$.

49. The compound of claim 48, wherein $R^{11}$ and $R^{12}$ are both hydrogen, and $R^{13}$ is selected from the group consisting of aryl, arylalkyl, heteroaryl, and heteroarylalkyl, wherein the aryl and heteroaryl portions thereof are optionally substituted with one or more substituents each independently selected from the group consisting of alkyl, alkoxy, halogen, haloalkyl, haloalkoxy, hydroxy, hydroxyalkyl, cyano, amino, aminoalkyl, alkylamino, dialkylamino, and hydroxyalkylamino, provided that when X is —CHR$^8$— and R$^8$ is hydrogen, and $R^{13}$ is aryl or arylalkyl, then the aryl portions are substituted by at least one of trifluoromethyl or trifluoromethoxy.

50. The compound of claim 49, wherein $R^{13}$ is phenyl, benzyl, phenylethyl, pyrrolyl, pyridyl, pyrimidyl, isoxazolyl, oxazolyl, thienyl, pyrrolyl($C_{1-2}$)alkyl, pyridyl($C_{1-2}$)alkyl, pyrimidyl($C_{1-2}$)alkyl, isoxazolyl($C_{1-2}$)alkyl, oxazolyl($C_{1-2}$)alkyl, or thienyl($C_{1-2}$)alkyl, wherein the aryl and heteroaryl portions thereof are optionally substituted with 1, 2, or 3 substituents each independently selected from the group consisting of $C_{1-4}$ alkyl, $C_{1-4}$ alkoxy, halogen, halo($C_{1-4}$)alkyl, halo($C_{1-4}$)alkoxy, hydroxy, hydroxy($C_{1-4}$alkyl, cyano, amino, amino($C_{1-4}$)alkyl, $C_{1-4}$ alkylamino, di($C_{1-4}$alkylamino, and hydroxy($C_{1-4}$)alkylamino.

51. The compound of claim 48, wherein $R^{11}$ is hydrogen, $R^{12}$ is selected from the group consisting of alkyl, haloalkyl, hydroxyalkyl, halogen, hydroxy, alkoxy, alkoxyalkyl, haloalkoxy, haloalkoxyalkyl, cyano, amino, aminoalkyl, alkylaminoalkyl, and dialkylaminoalkyl, and $R^{13}$ is selected from the group consisting of aryl, arylalkyl, heteroaryl, and heteroarylalkyl, wherein the aryl and heteroaryl portions thereof are optionally substituted with one or more substituents each independently selected from the group consisting of alkyl, alkoxy, halogen, haloalkyl, haloalkoxy, hydroxy, hydroxyalkyl, cyano, amino, aminoalkyl, alkylamino, dialkylamino, and hydroxyalkylamino.

52. The compound of claim 51, wherein $R^{12}$ is selected from the group consisting of $C_{1-4}$ alkyl, halo($C_{1-4}$)alkyl, hydroxy($C_{1-4}$alkyl, halogen, hydroxy, halo($C_{1-4}$)alkoxy, and halo($C_{1-4}$)alkoxy($C_{1-4}$)alkyl, and $R^{13}$ is phenyl, benzyl, phenylethyl, pyrrolyl, pyridyl, pyrimidyl, isoxazolyl, oxazolyl, thienyl, pyrrolyl($C_{1-2}$)alkyl, pyridyl($C_{1-2}$)alkyl, pyrimidyl ($C_{1-2}$)alkyl, isoxazolyl($C_{1-2}$)alkyl, oxazolyl($C_{1-2}$)alkyl, or thienyl($C_{1-2}$)alkyl, wherein the aryl and heteroaryl portions thereof are optionally substituted with 1, 2, or 3 substituents each independently selected from the group consisting of $C_{1-4}$ alkyl, $C_{1-4}$ alkoxy, halogen, halo($C_{1-4}$)alkyl, halo($C_{1-4}$) alkoxy, hydroxy, hydroxy($C_{1-4}$)alkyl, cyano, amino, amino ($C_{1-4}$alkyl, $C_{1-4}$ alkylamino, di($C_{1-4}$)alkylamino, and hydroxy($C_{1-4}$)alkylamino.

53. The compound of claim 48, wherein $R^{11}$ and $R^{12}$ are each independently selected from the group consisting of alkyl, haloalkyl, hydroxyalkyl, halogen, hydroxy, alkoxy, alkoxyalkyl, haloalkoxy, haloalkoxyalkyl, cyano, amino, aminoalkyl, alkylaminoalkyl, and dialkylaminoalkyl, and $R^{13}$ is selected from the group consisting of aryl, arylalkyl, heteroaryl, and heteroarylalkyl, wherein the aryl and heteroaryl portions thereof are optionally substituted with one or more substituents each independently selected from the group consisting of alkyl, alkoxy, halogen, haloalkyl, haloalkoxy, hydroxy, hydroxyalkyl, cyano, amino, aminoalkyl, alkylamino, dialkylamino, and hydroxyalkylamino.

54. The compound of claim 53, wherein $R^{11}$ and $R^{12}$ are each independently selected from the group consisting of $C_{1-4}$ alkyl, halo($C_{1-4}$)alkyl, hydroxy($C_{1-4}$)alkyl, halogen, hydroxy, halo($C_{1-4}$)alkoxy, and halo($C_{1-4}$)alkoxy($C_{1-4}$)alkyl, and $R^{13}$ is phenyl, benzyl, phenylethyl, pyrrolyl, pyridyl, pyrimidyl, isoxazolyl, oxazolyl, thienyl, pyrrolyl($C_{1-2}$)alkyl, pyridyl($C_{1-2}$)alkyl, pyrimidyl($C_{1-2}$)alkyl, isoxazolyl($C_{1-2}$) alkyl, oxazolyl($C_{1-2}$)alkyl, or thienyl($C_{1-2}$)alkyl, wherein the aryl and heteroaryl portions thereof are optionally substituted with 1, 2, or 3 substituents each independently selected from the group consisting of $C_{1-4}$ alkyl, $C_{1-4}$ alkoxy, halogen, halo ($C_{1-4}$)alkyl, halo($C_{1-4}$)alkoxy, hydroxy, hydroxy($C_{1-4}$)alkyl, cyano, amino, amino($C_{1-4}$)alkyl, $C_{1-4}$ alkylamino, di($C_{1-4}$) alkylamino, and hydroxy($C_{1-4}$)alkylamino.

55. The compound of claim 17, wherein
$R^1$ is —C(=W)NR$^3$R$^4$, wherein
W is O;
$R^3$ is hydrogen; and
$R^4$ is $C_{1-6}$ alkyl, $C_{2-6}$ alkenyl, halo($C_{1-6}$)alkyl, monohydroxy($C_{1-6}$)alkyl, dihydroxy($C_{1-6}$)alkyl, $C_{3-7}$ cycloalkyl, $C_{3-7}$ cycloalkyl($C_{1-4}$)alkyl, $C_{3-7}$ cycloalkenyl, $C_{3-7}$ cycloalkenyl($C_{1-4}$alkyl, phenyl, or benzyl, wherein the cycloalkyl, cycloalkenyl, and phenyl portions thereof are optionally substituted with 1, 2, or 3 substituents each independently selected from the group consisting of alkyl, alkoxy, halogen, haloalkyl, haloalkoxy, hydroxy, hydroxyalkyl, cyano, amino, aminoalkyl, alkylamino, dialkylamino, and hydroxyalkylamino;
$R^2$ is fluoro, chloro or bromo;
m is 0 or 1;
X is —CHR$^8$—;
$R^8$ and $R^9$ are both hydrogen or together form a bridge —(CH$_2$)$_p$—, wherein
p is 2, 3, or 4; and
$R^{10}$ is phenyl substituted with 1, 2 or 3 substituents each independently selected from the group consisting of $C_{1-4}$ alkyl, $C_{1-4}$ alkoxy, halogen, halo($C_{1-4}$)alkyl, halo ($C_{1-4}$)alkoxy, hydroxy, hydroxy($C_{1-4}$)alkyl, cyano, amino, amino($C_{1-4}$)alkyl, $C_{1-4}$ alkylamino, di($C_{1-4}$alkylamino, and hydroxy($C_{1-4}$)alkylamino.

56. The compound of claim 55, wherein R$^8$ and R$^9$ are both hydrogen.

57. The compound of claim 55, wherein R$^8$ and R$^9$ together form a bridge —(CH$_2$)$_p$—.

58. The compound of claim 17, wherein
$R^1$ is —C(=W)NR$^3$R$^4$, wherein
W is O;
$R^3$ is hydrogen; and
$R^4$ is $C_{1-6}$ alkyl, $C_{2-6}$ alkenyl, halo($C_{1-6}$)alkyl, monohydroxy($C_{1-6}$)alkyl, dihydroxy($C_{1-6}$)alkyl, $C_{3-7}$ cycloalkyl, $C_{3-7}$ cycloalkyl($C_{1-4}$)alkyl, $C_{3-7}$ cycloalkenyl, $C_{3-7}$ cycloalkenyl($C_{1-4}$alkyl, phenyl, or benzyl, wherein the cycloalkyl, cycloalkenyl, and phenyl portions thereof are optionally substituted with 1, 2, or 3 substituents each independently selected from the group consisting of alkyl, alkoxy, halogen, haloalkyl, haloalkoxy, hydroxy, hydroxyalkyl, cyano, amino, aminoalkyl, alkylamino, dialkylamino, and hydroxyalkylamino;
$R^2$ is fluoro, chloro or bromo;
m is 0 or 1;
X is —C(=O)—;
$R^9$ is hydrogen; and
$R^{10}$ is phenyl substituted with 1, 2 or 3 substituents each independently selected from the group consisting of $C_{1-4}$ alkyl, $C_{1-4}$ alkoxy, halogen, halo($C_{1-4}$)alkyl, halo ($C_{1-4}$alkoxy, hydroxy, hydroxy($C_{1-4}$)alkyl, cyano, amino, amino($C_{1-4}$)alkyl, $C_{1-4}$ alkylamino, di($C_{1-4}$) alkylamino, and hydroxy($C_{1-4}$)alkylamino.

59. The compound of claim 1, wherein said compound is

1'-(3-trifluoromethylbenzenesulfonyl)-1',2',3',6'-tetrahydro-[2,4]bipyridinyl-6-carboxylic acid cyclopropylamide;
1'-(4-trifluoromethoxybenzenesulfonyl)-1',2',3',6'-tetrahydro-[2,4']bipyridinyl-6-carboxylic acid cyclopropylamide;
1'-(3-chlorobenzenesulfonyl)-1',2',3',6'-tetrahydro-[2,4]bipyridinyl-6-carboxylic acid cyclopropylamide;
1'-(2-trifluoromethylbenzenesulfonyl)-1',2',3',6'-tetrahydro-[2,4]bipyridinyl-6-carboxylic acid cyclopropylamide;
1'-(4-trifluoromethylbenzenesulfonyl)-1',2',3',6'-tetrahydro-[2,4]bipyridinyl-6-carboxylic acid cyclopropylamide;
1'-(4-fluorobenzenesulfonyl)-1',2',3',6'-tetrahydro-[2,4]bipyridinyl-6-carboxylic acid cyclopropylamide;
1'-(3-cyanobenzenesulfonyl)-1',2',3',6'-tetrahydro-[2,4]bipyridinyl-6-carboxylic acid cyclopropylamide;
1'-dimethylsulfamoyl-1',2',3',6'-tetrahydro-[2,4]bipyridinyl-6-carboxylic acid cyclopropylamide;
1'-(3,3,3-trifluoropropylsulfonyl)-1',2',3',6'-tetrahydro-[2,4]bipyridinyl-6-carboxylic acid cyclopropylamide;
1'-cyclohexylsulfonyl-1',2',3',6'-tetrahydro-[2,4']bipyridinyl-6-carboxylic acid cyclopropylamide;
1'-(2,4-dichlorobenzenesulfonyl)-1',2',3',6'-tetrahydro-[2,4]bipyridinyl-6-carboxylic acid cyclopropylamide;
1'-(3-trifluoromethoxybenzenesulfonyl)-1',2',3',6'-tetrahydro-[2,4]bipyridinyl-6-carboxylic acid cyclopropylamide;
1'-(3-cyano-4-fluorobenzenesulfonyl)-1',2',3',6'-tetrahydro-[2,4]bipyridinyl-6-carboxylic acid cyclopropylamide;
1'-(pyridin-2-ylsulfonyl)-1',2',3',6'-tetrahydro-[2,4]bipyridinyl-6-carboxylic acid cyclopropylamide;
1'-(pyridin-3-ylsulfonyl)-1',2',3',6'-tetrahydro-[2,4]bipyridinyl-6-carboxylic acid cyclopropylamide;
1'-(3-trifluoromethylbenzylsulfonyl)-1',2',3',6'-tetrahydro-[2,4']bipyridinyl-6-carboxylic acid cyclopropylamide;
1'-(3,5-dichlorobenzenesulfonyl)-1',2',3',6'-tetrahydro-[2,4]bipyridinyl-6-carboxylic acid cyclopropylamide;
1'-(2,4,6-trifluorobenzenesulfonyl)-1',2',3',6'-tetrahydro-[2,4']bipyridinyl-6-carboxylic acid cyclopropylamide;
1'-(2-methylprop-1-ylsulfonyl)-1',2',3',6'-tetrahydro-[2,4]bipyridinyl-6-carboxylic acid cyclopropylamide;
1'-cyclopentylsulfonyl-1',2',3',6'-tetrahydro-[2,4]bipyridinyl-6-carboxylic acid cyclopropylamide;
1'-(thiophen-3-ylsulfonyl)-1',2',3',6'-tetrahydro-[2,4]bipyridinyl-6-carboxylic acid cyclopropylamide;
1'-(4-trifluoromethoxybenzyl)-1',2',3',6'-tetrahydro-[2,4]bipyridinyl-6-carboxylic acid cyclopropylamide;
2-[1-(4-trifluoromethoxybenzenesulfonyl)-1,2,3,6-tetrahydropyridin-4-yl]-pyrimidine-4-carboxylic acid amide;
2-[1-(3-trifluoromethylbenzenesulfonyl)-1,2,3,6-tetrahydropyridin-4-yl]-pyrimidine-4-carboxylic acid amide;
1'-(3-trifluoromethylbenzenesulfonyl)-1',2',3',6'-tetrahydro-[3,4]bipyridinyl-2-carboxylic acid methyl ester;
1'-(3-trifluoromethylbenzenesulfonyl)-1',2',3',6'-tetrahydro-[3,4]bipyridinyl-2-carboxylic acid cyclopropylmethylamide;
1'-(3-trifluoromethylbenzenesulfonyl)-1',2',3',6'-tetrahydro-[3,4]bipyridinyl-2-carboxylic acid 2,2,2-trifluoroethylamide;
1'-(3-trifluoromethylbenzenesulfonyl)-1',2',3',6'-tetrahydro-[3,4]bipyridinyl-2-carboxylic acid 3,3,3-trifluoropropylamide;
1'-(4-trifluoromethoxybenzenesulfonyl)-1',2',3',6'-tetrahydro-[3,4]bipyridinyl-2-carboxylic acid 2,2,2-trifluoroethylamide;
1'-(4-trifluoromethoxybenzenesulfonyl)-1',2',3',6'-tetrahydro-[3,4]bipyridinyl-2-carboxylic acid 3,3,3-trifluoropropylamide;
1'-(4-trifluoromethoxybenzenesulfonyl)-1',2',3',6'-tetrahydro-[3,4]bipyridinyl-2-carboxylic acid cyclopropylmethylamide;
1'-(3-trifluoromethylbenzenesulfonyl)-1',2',3',6'-tetrahydro-[2,4']bipyridinyl-6-carboxylic acid cyclopropylmethylamide;
1'-(3-trifluoromethylbenzenesulfonyl)-1',2',3',6'-tetrahydro-[2,4']-bipyridinyl-6-carboxylic acid 2,2,2-trifluoroethylamide;
1'-(3-trifluoromethylbenzenesulfonyl)-1',2',3',6'-tetrahydro-[2,4']-bipyridinyl-6-carboxylic acid 3,3,3-trifluoropropylamide;
1'-(4-trifluoromethoxybenzenesulfonyl)-1',2',3',6'-tetrahydro-[2,4']-bipyridinyl-6-carboxylic acid 2,2,2-trifluoroethylamide;
1'-(4-trifluoromethoxybenzenesulfonyl)-1',2',3',6'-tetrahydro-[2,4']-bipyridinyl-6-carboxylic acid 3,3,3-trifluoropropylamide;
1'-(4-trifluoromethoxybenzenesulfonyl)-1',2',3',6'-tetrahydro-[2,4']-bipyridinyl-6-carboxylic acid 4-fluorophenylamide;
1'-(3-trifluoromethylbenzenesulfonyl)-1',2',3',6'-tetrahydro-[2,4]bipyridinyl-6-carboxylic acid amide;
1'-(3-trifluoromethylbenzenesulfonyl)-1',2',3',6'-tetrahydro-[2,4]bipyridinyl-6-carboxylic acid 2-hydroxyethylamide;
1'-(3-trifluoromethylbenzenesulfonyl)-1',2',3',6'-tetrahydro-[2,4]bipyridinyl-6-carboxylic acid 1,3-dihydroxyprop-2-ylamide;
1'-(3-trifluoromethylbenzenesulfonyl)-1',2',3',6'-tetrahydro-[2,4]bipyridinyl-6-carbonitrile;
N-cyclopropylmethyl-1'-(4-trifluoromethoxybenzenesulfonyl)-1',2',3',6'-tetrahydro-[2,4']bipyridinyl-6-carboxamidine;
2-[1-(3-trifluoromethylbenzenesulfonyl)-1,2,3,6-tetrahydropyridin-4-yl]pyrimidine-4-carboxylic acid cyclopropylamide;
2-[1-(3-trifluoromethylbenzenesulfonyl)-1,2,3,6-tetrahydropyridin-4-yl]pyrimidine-4-carboxylic acid cyclopropylmethylamide;
2-[1-(4-trifluoromethoxybenzenesulfonyl)-1,2,3,6-tetrahydropyridin-4-yl]pyrimidine-4-carboxylic acid cyclopropylamide;
5-chloro-1'-(3-trifluoromethylbenzenesulfonyl)-1',2',3',6'-tetrahydro-[2,4']bipyridinyl-6-carboxylic acid cyclopropylamide;
5-chloro-1'-(4-trifluoromethoxybenzenesulfonyl)-1',2',3',6'-tetrahydro-[2,4']bipyridinyl-6-carboxylic acid cyclopropylamide;
6'-oxo-1'-(3-trifluoromethylbenzenesulfonyl)-1',2',3',6'-tetrahydro-[2,4']bipyridinyl-6-carboxylic acid cyclopropylamide;
6-[8-(3-trifluoromethylbenzenesulfonyl)-8-aza-bicyclo[3.2.1]oct-2-en-3-yl]pyridine-2-carboxylic acid cyclopropylamide;
2-[1-(4-trifluoromethoxybenzenesulfonyl)-1,2,3,6-tetrahydropyridin-4-yl]oxazole-4-carboxylic acid cyclopropylamide;

1'-[2,2,2-trifluoro-1-(4-trifluoromethoxyphenyl)-ethyl]-1',2',3',6'-tetrahydro-[2,4']bipyridinyl-6-carboxylic acid cyclopropylamide;

1'-[2,2,2-trifluoro-1-(4-hydroxymethylphenyl)-ethyl]-1',2',3',6'-tetrahydro-[2,4']bipyridinyl-6-carboxylic acid cyclopropylamide;

N-cyclopropyl-6-{1-[(3-trifluoromethylisoxazol-5-yl)methyl]-1,2,3,6-tetrahydropyridin-4-yl}picolinamide;

1'-(3-trifluoromethylbenzenesulfonyl)-1',2',3',6'-tetrahydro-[2,4']bipyridinyl-6-carboxylic acid methyl ester;

1'-(3-trifluoromethylbenzenesulfonyl)-1',2',3',6'-tetrahydro-[2,4']bipyridinyl-6-carboxylic acid;

1'-(3-trifluoromethylbenzenesulfonyl)-1',2',3',6'-tetrahydro-[2,4]bipyridinyl-6-yl]methanol;

1'-(3-trifluoromethylbenzenesulfonyl)-1',2',3',6'-tetrahydro[2,4']bipyridinyl-6-cyclopropanoylamine;

1'-[(3-trifluoromethylbenzene)aminosulfonyl]-1',2',3',6'-tetrahydro-[2,4']bipyridinyl-6-carboxylic acid cyclopropylamide;

or a pharmaceutically acceptable salt thereof.

60. A pharmaceutical composition, comprising the compound of claim 1, or a pharmaceutically acceptable salt thereof, and a pharmaceutically acceptable carrier.

61. A method for treating pain comprising administering an effective amount of a compound as claimed in claim 1 or a pharmaceutically acceptable salt thereof, to a mammal in need of such treatment.

62. A compound having the Formula I as claimed in claim 1, wherein the compound is $^3$H, $^{11}$C, or $^{14}$C radiolabeled, or a pharmaceutically acceptable salt thereof.

63. A method of screening a candidate compound for the ability to bind to a binding site on a protein using a radiolabeled compound of claim 62, comprising a) introducing a fixed concentration of the radiolabeled compound to a soluble or membrane-associated protein or fragment thereof to form a mixture; b) titrating the mixture with a candidate compound; and c) determining the binding of the candidate compound to said binding site.

64. A method of preparing a pharmaceutical composition, comprising admixing a therapeutically effective amount of a compound of claim 1, or a pharmaceutically acceptable salt thereof, with a pharmaceutically acceptable carrier.

\* \* \* \* \*

SEQUENCE LISTING

```
<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: Synthetic Primer

<400> SEQUENCE: 1
caccatggtc cgcttcgggg ac                                                  22

<210> SEQ ID NO 2
<211> LENGTH: 19
<212> TYPE: DNA
<213> ORGANISM: Artificial Sequence
<220> FEATURE:
<223> OTHER INFORMATION: Synthetic Primer

<400> SEQUENCE: 2
ccgttcagtg gcctcctcc                                                      19

<210> SEQ ID NO 3
<211> LENGTH: 23
<212> TYPE: DNA
<213> ORGANISM: Artificial Sequence
<220> FEATURE:
<223> OTHER INFORMATION: Synthetic Primer

<400> SEQUENCE: 3
ctagcaccag tgatcctggt ctg                                                 23

<210> SEQ ID NO 4
<211> LENGTH: 20
<212> TYPE: DNA
<213> ORGANISM: Artificial Sequence
```

```
<220> FEATURE:
<223> OTHER INFORMATION: Synthetic Primer

<400> SEQUENCE: 4
agtgcgttgt gagcgcagta                                              20

<210> SEQ ID NO 5
<211> LENGTH: 21
<212> TYPE: DNA
<213> ORGANISM: Artificial Sequence
<220> FEATURE:
<223> OTHER INFORMATION: Synthetic Primer

<400> SEQUENCE: 5
caccatggtc cagaagagcg g                                            21

<210> SEQ ID NO 6
<211> LENGTH: 21
<212> TYPE: DNA
<213> ORGANISM: Artificial Sequence
<220> FEATURE:
<223> OTHER INFORMATION: Synthetic Primer

<400> SEQUENCE: 6
tctcagcgga tgtagacgcc t                                            21

<210> SEQ ID NO 7
<211> LENGTH: 22
<212> TYPE: DNA
<213> ORGANISM: Artificial Sequence
<220> FEATURE:
<223> OTHER INFORMATION: Synthetic Primer

<400> SEQUENCE: 7
caccatgtat gacgactcct ac                                           22

<210> SEQ ID NO 8
<211> LENGTH: 23
<212> TYPE: DNA
<213> ORGANISM: Artificial Sequence
<220> FEATURE:
<223> OTHER INFORMATION: Synthetic Primer

<400> SEQUENCE: 8
ggtggtcagt agctgtcctt agg                                          23

<210> SEQ ID NO 9
<211> LENGTH: 21
<212> TYPE: DNA
<213> ORGANISM: Artificial Sequence
<220> FEATURE:
<223> OTHER INFORMATION: Synthetic Primer

<400> SEQUENCE: 9
caccatggct gctggctgcc t                                            21

<210> SEQ ID NO 10
<211> LENGTH: 25
<212> TYPE: DNA
<213> ORGANISM: Artificial Sequence
<220> FEATURE:
<223> OTHER INFORMATION: Synthetic Primer

<400> SEQUENCE: 10
agagggtcac catagatagt gtctg                                        25
```

```
<210> SEQ ID NO 11
<211> LENGTH: 22
<212> TYPE: DNA
<213> ORGANISM: Artificial Sequence
<220> FEATURE:
<223> OTHER INFORMATION: Synthetic Primer

<400> SEQUENCE: 11
caccatgatt cgggccttcg ct                                    22

<210> SEQ ID NO 12
<211> LENGTH: 25
<212> TYPE: DNA
<213> ORGANISM: Artificial Sequence
<220> FEATURE:
<223> OTHER INFORMATION: Synthetic Primer

<400> SEQUENCE: 12
agcctgcgga ctacaggttg ctgac                                 25
```